(12) United States Patent
Hanuka et al.

(10) Patent No.: US 9,517,157 B2
(45) Date of Patent: Dec. 13, 2016

(54) OSTOMY APPLIANCE

(71) Applicant: B. Braun Medical SAS, Boulogne-Billancourt (FR)

(72) Inventors: David Hanuka, Ramat-Yishai (IL); Meir Or, Kfar Eshchar (IL); Hadas Ziso, Kiryat-Tivon (IL)

(73) Assignee: B. Braun Medical SAS, Boulogne-Billancourt (FR)

( * ) Notice: Subject to any disclaimer, the term of this patent is extended or adjusted under 35 U.S.C. 154(b) by 0 days.

(21) Appl. No.: 14/789,684

(22) Filed: Jul. 1, 2015

(65) Prior Publication Data

US 2015/0305916 A1    Oct. 29, 2015

Related U.S. Application Data

(63) Continuation of application No. 14/400,005, filed as application No. PCT/IL2013/050401 on May 9, 2013.

(60) Provisional application No. 61/645,118, filed on May 10, 2012.

(51) Int. Cl.
| | |
|---|---|
| *A61F 5/44* | (2006.01) |
| *A61F 5/441* | (2006.01) |
| *A61F 5/445* | (2006.01) |
| *A61F 5/442* | (2006.01) |
| *A61F 5/448* | (2006.01) |
| *B31B 1/26* | (2006.01) |

(52) U.S. Cl.
CPC .......... *A61F 5/4407* (2013.01); *A61F 5/4401* (2013.01); *A61F 5/441* (2013.01); *A61F 5/442* (2013.01); *A61F 5/4404* (2013.01); *A61F 5/445* (2013.01); *A61F 5/4405* (2013.01); *A61F 5/448* (2013.01); *B31B 1/26* (2013.01); *A61F 2005/4402* (2013.01); *A61F 2005/4415* (2013.01)

(58) Field of Classification Search
CPC combination set(s) only.
See application file for complete search history.

(56) References Cited

U.S. PATENT DOCUMENTS

| | | | |
|---|---|---|---|
| 2,243,529 A | 5/1941 | Grossman et al. | |
| 2,341,984 A | 2/1944 | Graves | |
| 2,510,766 A | 6/1950 | Surface | |
| 2,544,579 A | 3/1951 | Ardner | |

(Continued)

FOREIGN PATENT DOCUMENTS

| | | |
|---|---|---|
| CN | 1694661 A | 11/2005 |
| DE | 19921555 A1 | 2/2000 |

(Continued)

OTHER PUBLICATIONS

International Search Report and Written Opinion for International Application No. PCT/IL2013/050401, mailed Dec. 20, 2013 (17 pages).

(Continued)

*Primary Examiner* — Adam Marcetich
*Assistant Examiner* — Guy K Townsend
(74) *Attorney, Agent, or Firm* — Kristina Bieker-Brady; Clark & Elbing LLP

(57) ABSTRACT

An ostomy appliance comprising an adaptor having a distal end adapted to be coupled to an ostomy wafer and a proximal end adapted to be coupled to a cap, said distal end having an opening in fluid communication with an opening in said proximal end.

26 Claims, 44 Drawing Sheets

(56) References Cited

U.S. PATENT DOCUMENTS

| | | | |
|---|---|---|---|
| 2,639,710 A | 5/1953 | Fazio | |
| 2,667,167 A | 1/1954 | Raiche | |
| 2,971,510 A | 2/1961 | Berger | |
| 3,398,744 A | 8/1968 | Hooper | |
| 3,447,533 A | 6/1969 | Spicer | |
| 3,718,141 A | 2/1973 | Goetz | |
| 3,976,076 A | 8/1976 | Beach | |
| 4,030,500 A | 6/1977 | Ronnquist | |
| 4,121,589 A | 10/1978 | McDonnell | |
| 4,170,231 A | 10/1979 | Collins | |
| 4,183,357 A | 1/1980 | Bentley et al. | |
| 4,209,010 A | 6/1980 | Ward et al. | |
| 4,210,131 A | 7/1980 | Perlin | |
| 4,217,664 A | 8/1980 | Faso | |
| 4,232,672 A | 11/1980 | Steer et al. | |
| 4,265,244 A | 5/1981 | Hill | |
| 4,338,937 A | 7/1982 | Lerman | |
| 4,344,434 A | 8/1982 | Robertson | |
| 4,351,322 A | 9/1982 | Prager | |
| 4,381,765 A | 5/1983 | Burton | |
| 4,399,809 A | 8/1983 | Baro et al. | |
| 4,421,124 A | 12/1983 | Marshall | |
| 4,460,363 A | 7/1984 | Steer et al. | |
| 4,462,510 A | 7/1984 | Steer et al. | |
| 4,534,761 A | 8/1985 | Raible | |
| 4,634,421 A | 1/1987 | Hegemann | |
| 4,642,107 A | 2/1987 | Arnone et al. | |
| 4,662,890 A | 5/1987 | Burton | |
| 4,721,508 A | 1/1988 | Burton | |
| 4,786,283 A | 11/1988 | Andersson | |
| 4,804,375 A | 2/1989 | Robertson | |
| 4,810,250 A | 3/1989 | Ellenberg et al. | |
| 4,834,731 A * | 5/1989 | Nowak | A61F 5/448 604/339 |
| 4,854,316 A | 8/1989 | Davis | |
| 4,863,447 A | 9/1989 | Smith | |
| 4,941,869 A | 7/1990 | D'Amico | |
| 4,950,223 A | 8/1990 | Silvanov | |
| 4,981,465 A | 1/1991 | Ballan et al. | |
| 5,004,464 A | 4/1991 | Leise, Jr. | |
| 5,026,360 A | 6/1991 | Johnsen et al. | |
| 5,045,052 A | 9/1991 | Sans | |
| 5,108,430 A | 4/1992 | Ravo | |
| 5,125,916 A | 6/1992 | Panebianco et al. | |
| 5,135,519 A | 8/1992 | Helmer | |
| 5,163,897 A | 11/1992 | Persky | |
| 5,163,930 A | 11/1992 | Blum | |
| 5,261,898 A | 11/1993 | Polin et al. | |
| 5,269,774 A | 12/1993 | Gray | |
| 5,372,594 A | 12/1994 | Colacello et al. | |
| 5,401,264 A | 3/1995 | Leise, Jr. | |
| 5,501,678 A | 3/1996 | Olsen | |
| 5,549,588 A | 8/1996 | Johnsen | |
| 5,569,216 A | 10/1996 | Kim | |
| 5,658,266 A | 8/1997 | Colacello et al. | |
| 5,683,372 A | 11/1997 | Colacello et al. | |
| 5,771,590 A | 6/1998 | Colacello et al. | |
| 5,785,677 A | 7/1998 | Auweiler | |
| 5,785,695 A | 7/1998 | Sato et al. | |
| 5,947,942 A | 9/1999 | Galjour | |
| 6,033,390 A | 3/2000 | von Dyck | |
| 6,050,982 A | 4/2000 | Wheeler | |
| 6,071,268 A * | 6/2000 | Wagner | A61F 5/445 604/332 |
| 6,329,465 B1 | 12/2001 | Takahashi et al. | |
| 6,350,255 B1 | 2/2002 | von Dyck | |
| 6,357,445 B1 | 3/2002 | Shaw | |
| 6,481,589 B2 | 11/2002 | Blomdahl et al. | |
| 6,485,476 B1 | 11/2002 | von Dyck et al. | |
| 6,589,222 B1 * | 7/2003 | Olsen | A61F 5/443 604/336 |
| 6,595,971 B1 | 7/2003 | von Dyck et al. | |
| 6,659,988 B1 | 12/2003 | Steer et al. | |
| 6,689,111 B2 | 2/2004 | Mulhauser et al. | |
| 6,695,825 B2 | 2/2004 | Castles | |
| 6,723,079 B2 | 4/2004 | Cline | |
| 6,963,772 B2 | 11/2005 | Bloom et al. | |
| 7,001,367 B2 | 2/2006 | Arkinstall | |
| 7,083,569 B2 | 8/2006 | Boulanger et al. | |
| 7,087,041 B2 | 8/2006 | von Dyck et al. | |
| 7,250,040 B2 | 7/2007 | Andersen | |
| 7,314,443 B2 | 1/2008 | Jordan et al. | |
| 7,582,072 B2 | 9/2009 | McMichael | |
| 7,628,767 B1 | 12/2009 | Simmons et al. | |
| 7,670,289 B1 | 3/2010 | McCall | |
| 7,722,586 B2 | 5/2010 | Mullejans et al. | |
| 7,857,796 B2 | 12/2010 | Cline et al. | |
| 8,070,737 B2 | 12/2011 | Cline et al. | |
| 8,092,437 B2 | 1/2012 | Cline | |
| 8,100,875 B2 | 1/2012 | Cline et al. | |
| 8,142,406 B2 | 3/2012 | Blum | |
| 8,388,586 B2 | 3/2013 | Weig | |
| 8,460,259 B2 | 6/2013 | Tsai | |
| 8,690,848 B2 | 4/2014 | Cason | |
| 8,821,464 B2 | 9/2014 | Hanuka et al. | |
| 8,821,465 B2 | 9/2014 | Hanuka et al. | |
| 8,845,607 B2 | 9/2014 | Hanuka et al. | |
| 8,858,519 B2 | 10/2014 | Hanuka et al. | |
| 8,864,729 B2 | 10/2014 | Hanuka et al. | |
| 8,900,116 B2 | 12/2014 | Hanuka et al. | |
| 8,998,862 B2 | 4/2015 | Hanuka et al. | |
| 2003/0004477 A1 * | 1/2003 | Nielsen | A61F 5/448 604/336 |
| 2003/0150050 A1 | 8/2003 | Tanaka et al. | |
| 2003/0199783 A1 | 10/2003 | Bloom et al. | |
| 2003/0220621 A1 | 11/2003 | Arkinstall | |
| 2004/0029467 A1 | 2/2004 | Lacroix | |
| 2004/0073179 A1 | 4/2004 | Andersen | |
| 2004/0122527 A1 | 6/2004 | Imran | |
| 2004/0167376 A1 | 8/2004 | Peters et al. | |
| 2004/0171999 A1 | 9/2004 | Andersen et al. | |
| 2004/0181197 A1 | 9/2004 | Cline | |
| 2004/0193122 A1 | 9/2004 | Cline et al. | |
| 2005/0027159 A1 | 2/2005 | Feng et al. | |
| 2005/0054996 A1 | 3/2005 | Gregory | |
| 2005/0065488 A1 | 3/2005 | Elliott | |
| 2005/0104457 A1 | 5/2005 | Jordan et al. | |
| 2005/0115857 A1 | 6/2005 | Homann | |
| 2006/0048283 A1 | 3/2006 | Sorensen | |
| 2006/0206069 A1 | 9/2006 | Cline | |
| 2006/0229596 A1 | 10/2006 | Weiser et al. | |
| 2007/0049878 A1 | 3/2007 | Kim et al. | |
| 2007/0088300 A1 | 4/2007 | Cline et al. | |
| 2007/0129695 A1 | 6/2007 | Blum | |
| 2007/0142780 A1 | 6/2007 | Van Lue | |
| 2007/0191794 A1 | 8/2007 | Cline et al. | |
| 2007/0219532 A1 | 9/2007 | Karpowicz et al. | |
| 2007/0260206 A1 | 11/2007 | Mullejans et al. | |
| 2007/0276346 A1 | 11/2007 | Poulsen et al. | |
| 2008/0004580 A1 | 1/2008 | Mullejans et al. | |
| 2008/0033380 A1 | 2/2008 | Andersen | |
| 2008/0091154 A1 | 4/2008 | Botten | |
| 2008/0108862 A1 | 5/2008 | Jordan et al. | |
| 2008/0135044 A1 | 6/2008 | Freitag et al. | |
| 2008/0269698 A1 | 10/2008 | Alexander et al. | |
| 2008/0275410 A1 | 11/2008 | Burt | |
| 2009/0043151 A1 | 2/2009 | Gobel | |
| 2009/0216206 A1 | 8/2009 | Nishtala et al. | |
| 2009/0247969 A1 | 10/2009 | Nishtala et al. | |
| 2010/0069859 A1 | 3/2010 | Weig | |
| 2010/0174253 A1 | 7/2010 | Cline et al. | |
| 2011/0040231 A1 | 2/2011 | Gregory | |
| 2011/0106032 A1 | 5/2011 | Kratky | |
| 2012/0109086 A1 | 5/2012 | Tsai | |
| 2012/0179124 A1 | 7/2012 | Nguyen-Demary et al. | |
| 2012/0245535 A1 * | 9/2012 | Jacobsson | A61F 5/445 604/264 |
| 2013/0053803 A1 | 2/2013 | Willoughby et al. | |
| 2013/0060212 A1 * | 3/2013 | Hanuka | A61F 5/445 604/333 |
| 2013/0060213 A1 * | 3/2013 | Hanuka | A61F 5/445 604/333 |
| 2013/0060214 A1 | 3/2013 | Willoughby et al. | |

(56) References Cited

U.S. PATENT DOCUMENTS

| | | | |
|---|---|---|---|
| 2013/0079736 A1* | 3/2013 | Hanuka | A61F 5/445 604/318 |
| 2013/0079737 A1* | 3/2013 | Hanuka | A61F 5/445 604/318 |
| 2013/0116642 A1 | 5/2013 | Hanuka et al. | |
| 2013/0304008 A1 | 11/2013 | Hanuka et al. | |
| 2015/0025488 A1 | 1/2015 | Hanuka et al. | |
| 2015/0057626 A1 | 2/2015 | Hanuka et al. | |
| 2015/0141944 A1 | 5/2015 | Hanuka et al. | |
| 2015/0305916 A1* | 10/2015 | Hanuka | A61F 5/4401 604/333 |

FOREIGN PATENT DOCUMENTS

| | | |
|---|---|---|
| DE | 102004001631 A1 | 8/2004 |
| DE | 102007062133 B3 | 7/2009 |
| EP | 1795157 A2 | 6/2007 |
| EP | 2027835 A1 | 2/2009 |
| FR | 2870112 A1 | 11/2005 |
| GB | 2094153 A | 9/1982 |
| JP | 2006-314479 A | 11/2006 |
| JP | 2008-507308 A | 3/2008 |
| WO | WO-87/03192 A1 | 6/1987 |
| WO | WO-90/07311 A1 | 7/1990 |
| WO | WO-96/32904 A1 | 10/1996 |
| WO | WO-99/43277 A1 | 9/1999 |
| WO | WO-01/49224 A1 | 7/2001 |
| WO | WO-02/058603 A1 | 8/2002 |
| WO | WO-03/065945 A1 | 8/2003 |
| WO | WO-03/071997 A1 | 9/2003 |
| WO | WO-2006/010556 A1 | 2/2006 |
| WO | WO-2007/030703 A2 | 3/2007 |
| WO | WO-2008/048856 A2 | 4/2008 |
| WO | WO-2008/103789 A2 | 8/2008 |
| WO | WO-2008/141180 A1 | 11/2008 |
| WO | WO-2009/083183 A2 | 7/2009 |
| WO | WO-2009/155537 A1 | 12/2009 |
| WO | WO-2011/013872 A1 | 2/2011 |
| WO | WO-2011/039517 A1 | 4/2011 |
| WO | WO-2011/057635 A1 | 5/2011 |
| WO | WO-2013/022487 A1 | 2/2013 |
| WO | WO-2014/081889 A1 | 5/2014 |
| WO | WO-2014/181338 A2 | 11/2014 |
| WO | WO-2014/181339 A2 | 11/2014 |

OTHER PUBLICATIONS

Invitation to Pay Additional Fees and, Where Applicable, Protest Fee for International Application No. PCT/IL2013/050401, mailed Sep. 16, 2013 (6 pages).

Zhang et al., "Occlusion effect comparison of artificial silicone rubber closure devices with different diameters," Chinese Journal of Tissue Engineering Research 16(8):1496-1500 (2012). Abstract in English.

* cited by examiner

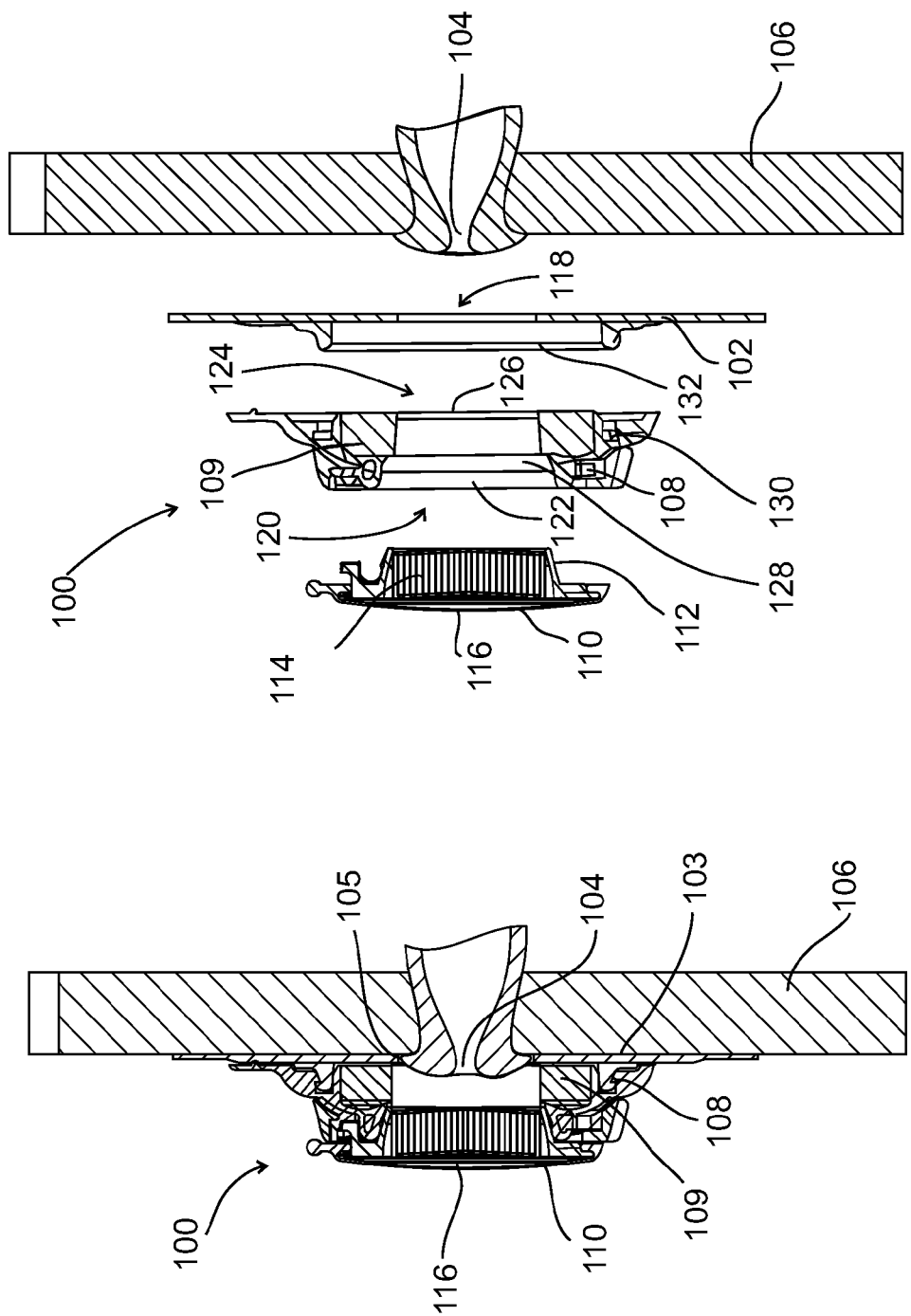

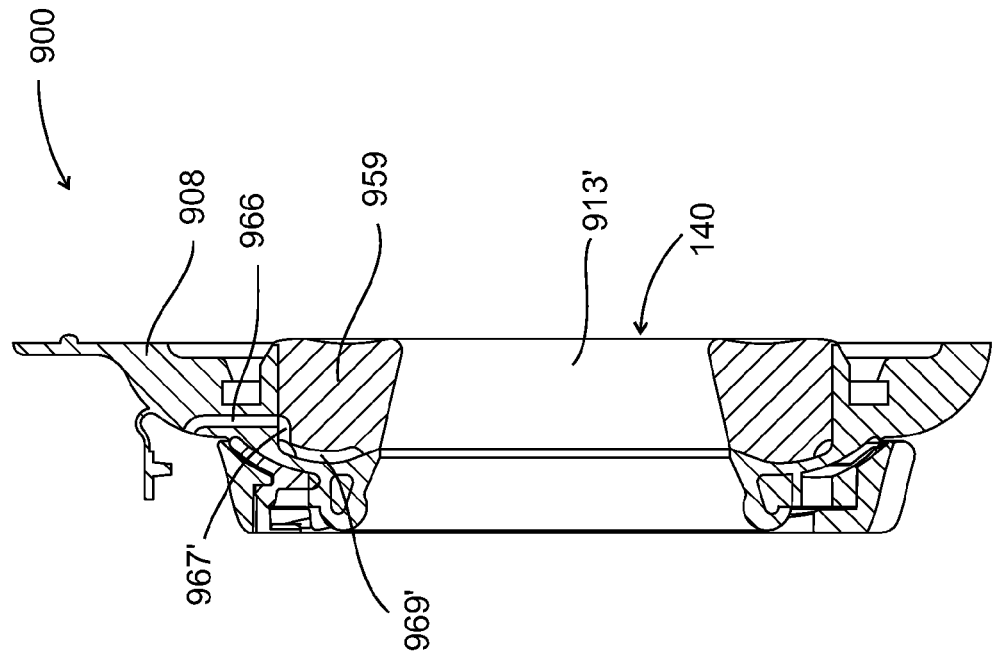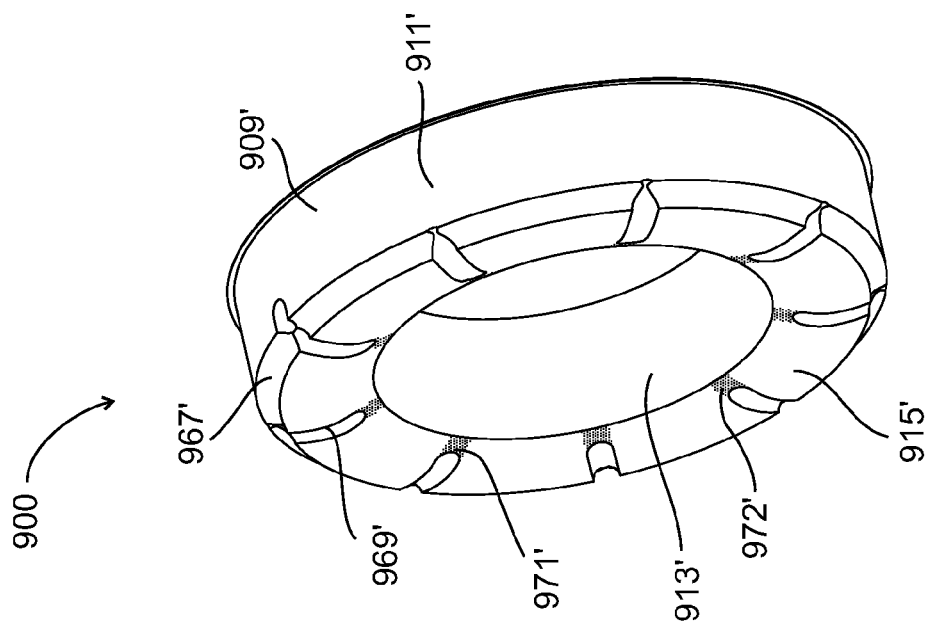

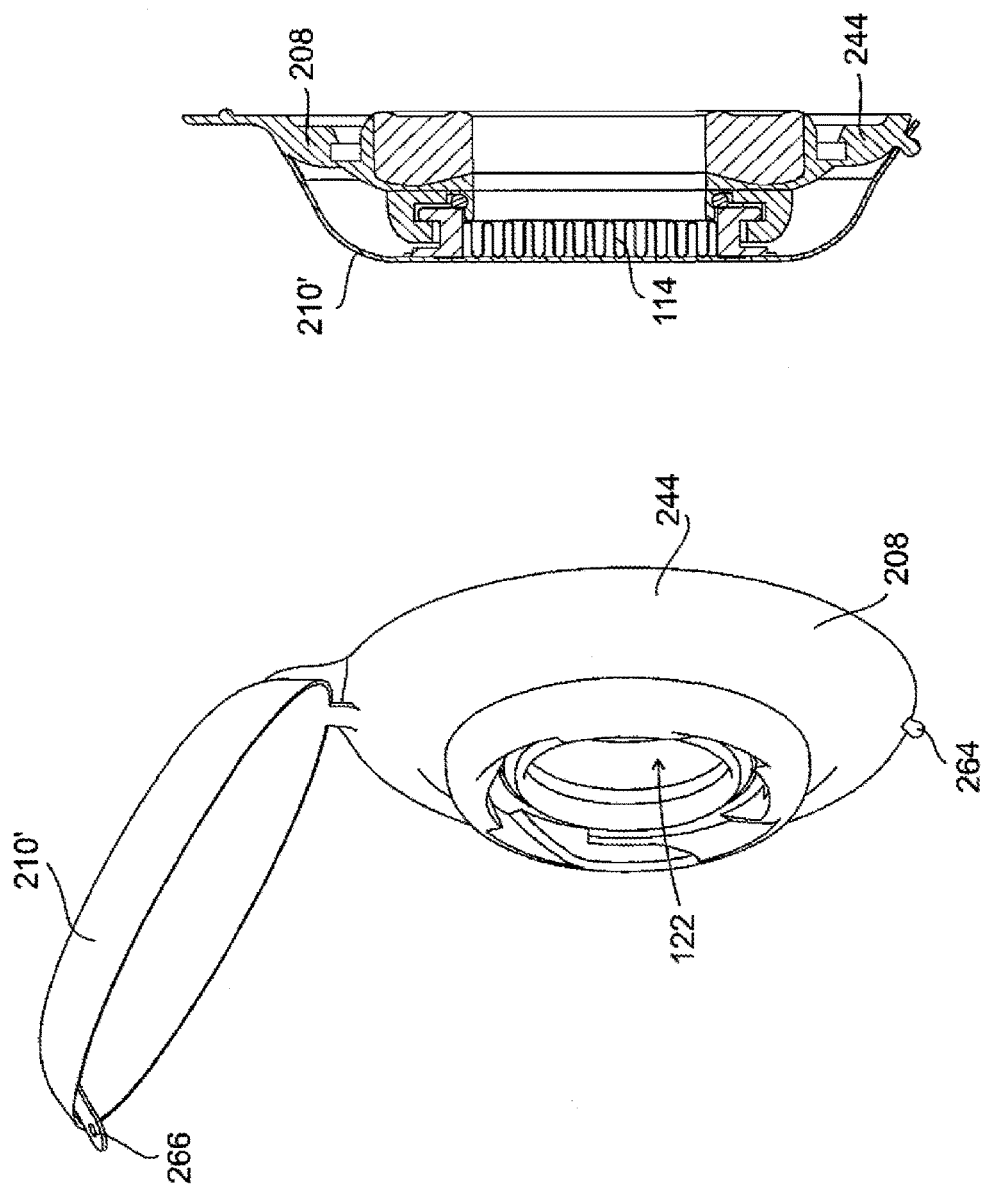

OSTOMY APPLIANCE

RELATED APPLICATIONS

This application claims the benefit of priority under 35 USC §119(e) of U.S. Provisional Patent Application No. 61/645,118 filed May 10, 2012, the contents of which are incorporated herein by reference in their entirety. This application is related to International Patent Application No. IB2011/051938 filed May 2, 2011.

FIELD AND BACKGROUND OF THE INVENTION

The present invention, in some embodiments thereof, relates to the field of surgically created openings for waste removal (stoma) in living subjects, and more particularly, to devices and methods for covering a stoma as may be used in the case of a colostomy, ileostomy or urostomy.

In performing an ostomy, the physician will generally form the stoma in the abdominal wall and attach an end or a side of a healthy portion of the intestine (large or small intestine, depending on the type of ostomy) to the stoma from the visceral side of the abdominal wall or, alternatively, pass the intestinal portion through the stoma and attach it to the outside of the abdominal wall. The stoma may be permanently left in a patient suffering from a condition for when it is no longer possible for the intestinal content to pass out via the anus, for example, due to colon cancer, diverticulitis, trauma, or inflammatory bowel disease, or may be temporary, as may be the case following an operation on a section of the bowel (small intestine and/or large intestine) requiring a healing period.

During or following the surgical procedure, an invasive ostomy port may be temporarily or permanently inserted through the stoma for conducting the body wastes from the intestine through the stoma. The invasive ostomy port may also serve to prevent the body wastes from coming in contact with the external abdominal wall as they are expelled through the stoma. Such an invasive ostomy port, in various embodiments thereof, is described by the Applicant in WO 2011/13872 A2, incorporated herein by reference in its entirety.

A waste collection bag (also known as "pouch") is frequently attached to the invasive ostomy port on the side of the external abdominal wall for collecting the waste content flowing through the port. The pouch may be of a disposable type or may be reusable following emptying of its contents.

In some ports, either invasive or non-invasive, a cap is removably attached to the port for maintaining the port sealed and the waste content inside. When required, the user removes the cap and attaches the pouch, replacing the cap following the port having been substantially emptied from the accumulated waste content.

Alternatively to the use of the invasive ostomy port and possibly more popular due to its simplicity and comparatively low cost is the non-invasive ostomy port such as ostomy wafer (also known as "skin barrier" or "faceplate") or ostomy belt. Such a wafer is typically a patch which is placed over the stoma on the external abdominal wall and protects the skin around the stoma from coming into contact with the waste content. The wafer typically includes an adhesive on one side for removably adhering it to the abdominal wall. It generally includes a flange or other pouch attachment element to which a pouch may be either removably or permanently attached. The combination of a wafer with a removable pouch is generally referred to in the art as an ostomy "two-piece" system whereas that of a wafer with a fixed, non-removable pouch is generally referred to as an ostomy "one-piece" system. The wafer also includes a wafer port peripherally surrounded by the flange and in fluid communication with the stoma for allowing waste content flow from the stoma into the pouch. One requirement of the wafer port is that it be sized to accommodate a portion of the stoma which may protrude from the abdominal wall. Some wafers may be available in different sizes and/or may have different sized ports so that a user may select a wafer with a suitably sized port. Other wafers may include a wafer port template so that the user may cut an opening in the template suitable for accommodating the stoma. Still other wafers may include wafer ports which may be manually shaped by the user to accommodate the stoma.

In addition to the one-piece and the two-piece system described above, other non-invasive ostomy ports are known in the art. Some example are described in U.S. Pat. No. 7,250,040 to Andersen; U.S. Patent Application Publication Number 2004/0181197, 2007/0088300, and 2007/0191794, to Clive et al.; and U.S. Pat. No. 6,689,111 to Mulhauser et al.

U.S. Pat. No. 7,250,040 relates to "an arrangement at a stoma bag of the type used by persons or animals with a colostoma, including a flexible bag (flexibag) and a ring fastener/magazine ring, where the ring fastener/magazine ring is designed to be connected to a stoma plate, and where, in its initial position, the entire flexibag is located in or in close proximity to the ring fastener/magazine ring."

U.S. Patent Application Publication Number 2004/0181197 relates to "a flexible membrane is situated within a rigid or semi-rigid cap. The edge of the cap wall is adhesively fixed to the tissue surrounding the stoma. The interior of the cap is pressurized to press the membrane to seal the stoma against the discharge of solid and semi-solid waste. Gas escapes through a vent with a filter element. The cap can be pressurized by an external pump or an integral pump member situated on top of the cap. A relief valve prevents over pressurization. A collection pouch can be provided as part of a device. The device can be removably mounted on a standard two-piece faceplate."

U.S. Patent Application Publication Number 2007/0088300 relates to "a single-use ostomy appliance is described including an ostomy coupling for releasable coupling first and second portions at a stomal orifice. The two portions may be separable body-side and non-body-side parts, or the two portions may be portions of a unitary ostomy device such as a controlled evacuation device. The coupling includes a mechanical fastener configured such that the coupling is rendered substantially not resecurable after the fastener is released."

U.S. Patent Application Publication Number 2007/0191794 relates to "a controlled evacuation ostomy appliance comprises a membrane that is urged into sealing engagement with a stoma, by the generation of radial tension in the membrane. A tensioning device applies tension, with respect to the stoma, at one or more positions that are (i) outboard of the periphery of the projecting portion of the stoma, and/or (ii) between the level of the peristomal skin and the level of the most projecting part of the stoma. Tension limiting means are disclosed. The membrane may be gas-permeable to allow flatus to be vented."

U.S. Pat. No. 6,689,111 relates to "a balloon-like member is received in the bowel and inflated to seal the stoma. The member includes a thin, flexible wall defining an opening. A rigid or semi-rigid cap retains the member and closes the opening in the member wall. Skin comfortable adhesive adheres the edge of the cap to the tissue surrounding the stoma. A flexible dilation tube facilitates insertion of the member and cooperates with a pump to inflate the member. The cap is preferably removeably attached to a standard two-piece ostomy faceplate and is provided with a filter element to vent flatus."

SUMMARY OF THE INVENTION

According to an aspect of some embodiments of the present invention there is provided an ostomy appliance comprising an adaptor having a distal end adapted to be coupled to an ostomy wafer and a proximal end adapted to be coupled to a cap, said distal end having an opening in fluid communication with an opening in said proximal end.

According to some embodiments of the invention a cap is provided, adapted to be removably coupled to said adaptor.

According to some embodiments of the invention, said ostomy wafer is removably coupled to said adaptor.

According to some embodiments of the invention, said adaptor includes a sealing mechanism for sealing a wafer/adaptor interface.

According to some embodiments of the invention, said adaptor includes an attachment mechanism configured to mate with an attachment element on said wafer, and said sealing mechanism is integral to said attachment mechanism.

According to some embodiments of the invention, said adaptor includes an attachment mechanism for mating with an attachment element on said wafer.

According to some embodiments of the invention, said attachment mechanism includes a snap-fit mechanism.

According to some embodiments of the invention, said attachment mechanism includes a twist-and-lock mechanism.

According to some embodiments of the invention, said attachment mechanism comprises a chemical bonding mechanism.

According to some embodiments of the invention, there is provided a cap locking mechanism for affixing said cap to said adaptor.

According to some embodiments of the invention, the cap is affixed by threading onto the adaptor.

According to some embodiments of the invention, said cap locking mechanism is adapted to sealingly couple between the cap and the adaptor.

According to some embodiments of the invention, said sealing is configured to withstand a pressure differential of 15 mmHg.

According to some embodiments of the invention, said sealing is configured to withstand a pressure differential of 50 mmHg.

According to some embodiments of the invention, said sealing is configured to withstand a pressure differential of 150 mmHg.

According to some embodiments of the invention, said adaptor includes an opening for releasing gas flowing from the stoma.

According to some embodiments of the invention, said opening is selectively controlled by a user of the ostomy appliance.

According to some embodiments of the invention, said adaptor includes a rotatable ring for releasing gases flowing from the stoma.

According to some embodiments of the invention, manipulating said rotatable ring adjusts a release rate of said gas.

According to some embodiments of the invention, said adaptor includes a gas filtering mechanism for filtering gases flowing from the stoma.

According to some embodiments of the invention, there is provided a sealing element adapted to be accommodated within an interior cavity of said adaptor.

According to some embodiments of the invention, said sealing element includes a soft elastomer.

According to some embodiments of the invention, said sealing element includes an inflatable balloon.

According to some embodiments of the invention, said sealing element includes a compressed foam element.

According to some embodiments of the invention, said compressed foam element is adapted to filter gases flowing from the stoma.

According to some embodiments of the invention, less than 15 cc of the internal lumen is available to be occupied by stomal waste when worn.

According to some embodiments of the invention, less than 5 cc of the internal lumen is available to be occupied by stomal waste when worn.

According to some embodiments of the invention, less than 1 cc of the internal lumen is available to be occupied by stomal waste when worn.

According to some embodiments of the invention, said ostomy appliance does not press on the stoma when worn.

According to some embodiments of the invention, the axial length of the closed ostomy appliance is 12 mm or less.

According to some embodiments of the invention, the axial length of the closed ostomy appliance is 6 mm or less.

According to an aspect of some embodiments of the present invention there is provided an ostomy component sealing system for sealing to an ostomy wafer comprising: a housing adapted to be attached to said wafer; and a sealing mechanism, formed of at least one element, that resists the flow of pressurized gasses through the housing-wafer interface.

According to some embodiments of the invention, the at least one sealing mechanism element comprises an element integrally formed in the housing which presses against a surface of the wafer to form a seal that resists the outflow of gasses under pressure from the stoma.

According to some embodiments of the invention, the at least one sealing mechanism element comprises an element integrally formed in the wafer which presses against a surface of the housing to form a seal that resists the outflow of gasses under pressure from the stoma.

According to some embodiments of the invention, the at least one sealing mechanism element comprises a separate element contained within a cavity of the wafer which presses against a surface of at least one of the housing and the stoma to form a seal that resists the outflow of gasses under pressure from the stoma.

According to some embodiments of the invention, the housing comprises the housing of an ostomy cap.

According to some embodiments of the invention, the housing comprises a lumen having a proximal end, and is attached to a collapsed collection bag which closes the proximal end.

According to some embodiments of the invention, the housing is attached to a pouch deployment prevention element which at least partially covers the collapsed collection bag and the closed proximal end.

According to some embodiments of the invention, the housing comprises a cavity sized to hold a filter, and within the cavity there is a filter for filtering gasses flowing from the stoma.

According to some embodiments of the invention, the housing comprises the housing of an ostomy adaptor appliance.

According to some embodiments of the invention, the housing and the at least one element of the sealing mechanism element do not press on the stoma.

According to an aspect of some embodiments of the present invention there is provided a method of sealing a stoma in a subject's body comprising: attaching an ostomy wafer over the stoma; attaching an adaptor to said wafer; and fitting a cap onto said adaptor.

According to some embodiments of the invention, said cap is fitted prior to attachment of said adaptor to said wafer.

According to some embodiments of the invention, a collapsed pouch is attached onto said adaptor.

According to some embodiments of the invention, said adaptor is fitted to said wafer prior to attaching said wafer over the stoma.

According to some embodiments of the invention, sealing the stoma is done without applying direct force to the stoma.

According to an aspect of some embodiments of the present invention there is provided a method of sealing a stoma in a subject's body comprising: attaching an ostomy wafer over the stoma; and fitting onto said adaptor a cap comprising a collapsed pouch, a deployment prevention element and a gas filter, without applying direct force to the stoma.

According to some embodiments of the invention, the adaptor and the cap are integrally coupled.

According to some embodiments of the invention, the adaptor and the wafer are integrally coupled.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A schematically illustrates a sectional view of the ostomy appliance attached to the wafer covering the stoma, in accordance with an exemplary embodiment of the present invention;

FIG. 2B schematically illustrates an exploded view of FIG. 2A, in accordance with an exemplary embodiment of the present invention;

FIG. 17A schematically illustrates a perspective view of a flushing-type sealing element, in accordance with some exemplary embodiments of the present invention;

FIG. 17B schematically illustrates a sectional view of adaptor with the sealing element inside a cavity, in accordance with some exemplary embodiments of the present invention;

FIG. 22A schematically illustrates a perspective view of the adaptor shown in FIGS. 5A and 5B including an integral cap, in accordance with some exemplary embodiments of the present invention;

FIG. 22B schematically illustrates a sectional view of the adaptor and the integral cap shown in FIG. 22A, in accordance with some exemplary embodiments of the present invention;

DESCRIPTION OF SPECIFIC EMBODIMENTS OF THE INVENTION

Figure 1:
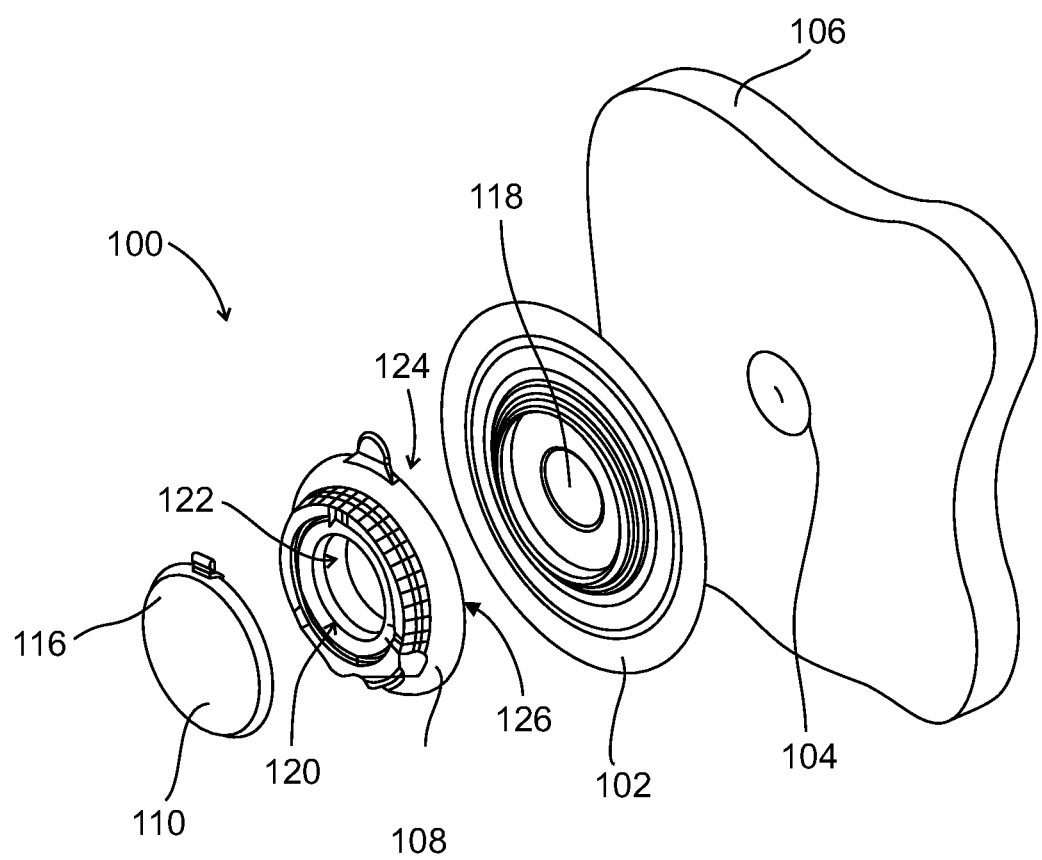
FIG. 1 schematically illustrates an exploded perspective view of an ostomy appliance that couples a cap to an ostomy wafer through an adaptor, in accordance with an exemplary embodiment of the present invention.

The present invention, in some embodiments thereof, relates to the field of surgically created openings for waste removal (stoma) in living subjects, and more particularly, to devices and methods for covering a stoma as may be used in the case of a colostomy, ileostomy or urostomy.

An aspect of some embodiments of the present invention relates to coupling a cap to an ostomy wafer. Optionally, the coupling is temporary and/or reversible. In some embodiments, the coupling is permanent and/or integral.

An aspect of some embodiments of the present invention relates to an ostomy appliance component for coupling a cap to an ostomy wafer. Optionally, the coupling is through an adaptor having a proximal end for connecting a cap and an opposing distal end for connecting an ostomy wafer. Optionally, the proximal and the distal end are fluid communication with one another. "Proximal end" refers to an end of the adaptor furthest away from the stoma in a direction away from the abdomen while "distal end" refers to an end of the adaptor closest to the stoma in a direction into the abdomen.

In some embodiments, the adaptor is adapted to couple the cap to the wafer by pressing the cap against the wafer. In some embodiments, the cap and/or the wafer is detachable. Optionally, an adaptor may be configured to accommodate a cap by an attachment mechanism configuration selected according to the cap design. Optionally, an adaptor may be configured to accommodate a wafer by an attachment mechanism configuration selected according to the wafer design. The cap-accommodating attachment mechanism configuration on the adaptor may be different than the attachment mechanism configuration used by the wafer. Potentially, this permits wafers and caps to be used in combination within a single stack of elements comprising an ostomy appliance (an "ostomy stack"), even in certain cases where their combination was not contemplated as a requirement of their original design. Alternatively, a cap attachment element may be fitted onto the cap and/or the adaptor for enabling coupling of the prior art cap to the wafer. Optionally, the cap attachment element may be exchangeable, allowing coupling of different types of caps to the wafer. In some embodiments, the cap is a non-invasive cap optionally housing a collapsed waste collection pouch. Optionally, the pouch may be automatically or manually deployed. Optionally, the adaptor attaches to a pouch attachment element on the wafer, for example a flange used for attaching waste collection pouches.

An aspect of some embodiments of the present invention relates to primary sealing of the ostomy appliance. Primary sealing resists the flow of gasses at pressures normally generated from within a stoma, for example 10-20 mmHg, 30-70 mmHg, 100-200 mmHg, or a range with intermediate values. Primary sealing also prevents the leakage of solid and liquid stomal discharge.

In some exemplary embodiments, the ostomy appliance may include a sealing system which provides for primary sealing at one or more component-component interfaces and/or component-tissue interfaces. For example, sealed component-component interfaces may be between a cap and an adaptor, an adaptor and a wafer, or a cap and a wafer. Also for example, a sealed component-tissue interface may be between a cap and a stoma, an adaptor and a stoma, a wafer and a stoma, or between one of those ostomy components and the peristomal skin. In some exemplary embodiments, sealing at component-component interfaces is designed such that passage of gas at the interface is substantially prevented when a pressure differential in the range of, for example, 10-20 mmHg, 30-70 mmHg, 100-200 mmHg, or a range with intermediate values exists across the interface.

An aspect of some embodiments of the present invention relates to the introduction of fluids to the stoma, surrounding tissue and/or organ surfaces internal to the stoma. The ostomy appliance may further include a flushing mechanism for washing an inside of the appliance, and/or for washing the peristomal skin and/or the stoma.

Additionally or alternatively, the flushing mechanism may be used for intestinal irrigation.

An aspect of some embodiments of the present invention relates to ostomy components which couple to one another in potentially different combinations of structural roles and/or attachment mechanisms. In some exemplary embodiments, the adaptor, the cap, and the wafer are three separate attachable components. Optionally, the ostomy appliance is a non-disposable item, and all the components are washable. Alternatively, one or more components of the ostomy appliance is a disposable item, that is, one or more of the cap, the adaptor, and the wafer are separately disposable after a predetermined number of uses or a predetermined amount of time which may vary according to the component. For example, the cap may be disposed of after a single use, while the wafer after three days of use, and the adaptor after one year of use during which time it may be washed on a regular basis.

In some embodiments, the cap and the ostomy appliance are a single component attachable to the wafer. Alternatively, the ostomy appliance and the wafer are a single component to which the cap may be attached. Alternatively, the cap, the ostomy appliance and the wafer are a single component.

A potential advantage of having an ostomy appliance which may be used with caps and/or wafers of potentially uncoordinated design is a reduced production cost compared to that of producing it together with the cap and/or wafer, making the item more accessible to users at a lower cost. Another potential advantage is to allow users who have established a preference for one ostomy component, such as a wafer, to enjoy access to a wider range of alternatives for other ostomy components, such as caps.

In contrast, a potential advantage of combining into merged ostomy components the functions of, for example, a cap, a wafer, and/or an adaptor is the simplification of a potentially tedious procedure requiring that the user attach each component separately. This may be particularly of benefit to users having poor motor skills.

An aspect of some embodiments of the present invention relates to protection of the stoma from potentially damaging sustained contact with components of a surrounding ostomy appliance. In some embodiments, the ostomy appliance is adapted to be physically isolated from the stoma, optionally from the peristomal skin, potentially preventing possible tissue damage to the stoma and/or surrounding area due to contact, friction, mechanical stress and/or use of non-biocompatible materials in part of the appliance.

In some exemplary embodiments, the distal end of an adaptor is cross-sectionally shaped to conform to a shape of the stoma. For example, the cross-sectional shape may be circular for use with circular stomas, or may have non-circular shapes, for example, elliptical for use with elliptically shaped stomas. Additionally or alternatively, the distal end is cross-sectionally shaped to conform to the shape of a wafer port in the wafer and/or the proximal end is cross-sectionally shaped to conform to the shape of a cap.

In some exemplary embodiments, the adaptor is configured for being sealingly attached at the distal end to a pouch attachment element on a wafer, so that the seal peripherally surrounds the wafer port. Optionally, the distal end attaches to another attachment element on the wafer, for example, a rim for fitting a cap, or a dedicated attachment element configured for attaching the adaptor. At this wafer/adaptor interface, the connection may include use of an O-ring or other type of sealing element for preventing waste content leakage. Attaching the adaptor to the wafer allows for waste content flow from the stoma, optionally through the wafer port, into the adaptor, without the adaptor being in physical contact with the stoma. This physical isolation is potentially advantageous for protecting the tissue against damage from mechanical stress and/or use of non-biocompatible materials. In some embodiments, the adaptor is sealingly attached to the wafer as a single component, for example, during a manufacturing process wherein the adaptor is formed integrally with the wafer, or is attached using known processes, including welding or bonding. Bonding comprises one or both of chemical bonding and adhesive bonding. Adhesive bonding, according to the specific embodiment, includes adhesive materials used and processes performed during original manufacture and/or adhesive materials used and processes performed by the end user.

In some exemplary embodiments, the adaptor may be used, according to specifics of its design, with one or more of an assortment of alternative wafer designs, potentially including designs for which use with an adaptor was not originally contemplated. For example, different embodiments of the adaptor may have different types and/or sizes of attachment mechanisms for mating with the pouch attachment elements of different wafer designs. Optionally, the adaptor is configured for use with wafers having adjustable size wafer ports for accommodating different stoma sizes. In some embodiments, the adaptor has a one-size/type attachment mechanism which mates with a one-size/type pouch attachment element in a "dedicated" wafer.

In some embodiments, the adaptor is configured for being used with stoma of different heights, for example, by having a single height which is suitable for varying stoma heights. For example, the single height adaptor may be capable of accommodating stomal protrusion in a proximal direction away from the abdomen by up to 2 cm, 1.5 cm, 1 cm, 0.5 cm, or less. Alternatively, the adaptor can be of a particular height according to the requirements of a particular user. For example, a first size adaptor may accommodate a stomal protrusion ranging from 0-0.5 cm, a second size adaptor may accommodate a stomal protrusion ranging from 0.5 cm-1.5 cm, and a third size adaptor may accommodate a stomal protrusion ranging from 1.5 cm-2 cm. In some embodiments, the adaptor provides these and/or other adaptations, a wafer of a type suitable to be cut to size for use with a standard size adaptor.

An aspect of some embodiments of the present invention relates to the flexibility of an ostomy appliance. In some exemplary embodiments, major structural elements of the adaptor and/or the cap, for example, their body or housing, may be wholly made of a flexible and/or elastic material, for example, silicone rubber or thermoplastic elastomer (TPE). Optionally, the material may be of a durometer ranging from 20-80 Shore A, 25-75 Shore A, 35-75 Shore A, 45-75 Shore A, 50-75 Shore A. In some embodiments, attachment mechanisms are of a sufficiently rigid material for substantially limiting a possibility of mechanical failure of attachment mating between components. For example, the material may be a silicone rubber of high durometer in a range of between 50-90 Shore A, 55-85 Shore A, 60-80 Shore A, or may be a semi-rigid thermoplastic such as polyethylene or a rigid thermoplastic such as polyamide. In some embodiments, the attachment mechanism is formed from the same material as the adaptor and/or cap. Alternatively, the attachment mechanism may be formed from different material than the adaptor and/or cap. Separate materials offer a potential advantage in that the adaptor and/or cap may be formed from the flexible and/or elastic material while the attachment mechanism is formed from the more rigid material.

An aspect of some embodiments of the present invention relates to the use of combinations of ostomy components having different ostomy component features. In some exemplary embodiments, the adaptor is used with the cap attached to the proximal end by the user at the time of use. Optionally, the cap is a non-invasive cap. In some embodiments, the cap is disposable. Alternatively, the proximal end is attached to the cap as a single component, for example, during a manufacturing process wherein the adaptor is formed integrally with the cap, or is attached using known processes, including welding or bonding.

In some embodiments, the cap houses the collapsed pouch and includes a removable lid for allowing pouch deployment. In some embodiments, the collapsed pouch is accommodated inside a housing which is attached to the adaptor. Optionally, the housing and pouch are replaceable as a single unit. In some embodiments, the cap is integrally attached to the adaptor and the housing accommodating the pouch is removably attached to the adaptor, for example, by inserting through an opening in the cap following removing of a lid. In some embodiments, the collapsed pouch is deployable when a user needs to eliminate waste through the stoma. In some embodiments, deployment of the pouch is automatic, for example, responsive to a pressure buildup inside the ostomy appliance from waste content. Additionally or alternatively, the user deploys the pouch, for example, in response to a signal from a warning mechanism in the ostomy appliance, or periodically according to predetermined criteria, or randomly as desired, or any combination thereof.

In some embodiments, the ostomy appliance includes a gas release system for allowing the user to release gases from within the stoma without deploying the pouch or removing the cap. International Patent Publication Nos. WO 2011/13872 A2, WO 2011/138731 A2, and WO 2011/138727 A1 by the applicant and all incorporated herein by reference in their entirety, describe various embodiments of smart caps, automatic and manual pouch deployment mechanisms, pressure warning mechanisms, gas release mechanisms, and irrigation mechanisms, which may be incorporated individually or in combination in some embodiments of the present invention.

In some exemplary embodiments, use of the ostomy appliance may include attaching the adaptor to the wafer prior to placing the wafer over the stoma.

Alternatively, the user may first place the wafer over the stoma and then attach the adaptor. The cap may be attached to the adaptor either before attachment to the wafer, or after attachment. In some embodiments, the user replaces the cap following deployment of the pouch.

An aspect of some embodiments of the present invention relates to secondary sealing of the ostomy appliance. Secondary sealing controls the access of stomal waste, particularly liquid waste but potentially also gaseous and/or solid waste, to tissue and/or appliance surfaces inside the ostomy appliance. In some embodiments, secondary sealing may seal and/or contribute to sealing against leakage from the ostomy appliance of liquids, solids, and/or stomal gases. An aspect of some embodiments of the present invention relates to a sealing element for use with an ostomy appliance for providing sealing at a wafer/stoma interface. Use of the sealing element provides a second level of sealing in the ostomy appliance in addition to that at the wafer/adaptor interface. The sealing element is sized and shaped to be fittedly accommodated inside the adaptor, and optionally includes a hole for allowing waste content flow through the element. Optionally, the sealing element is adapted to peripherally surround the wafer port and to press against the wafer for providing sealing at the wafer/stoma interface. Additionally or alternatively, the sealing element presses against the stoma for providing the sealing.

In some exemplary embodiments, the sealing element is adapted to direct at least a portion of the waste content flow from the stoma through the opening in an axial direction towards the proximal end. Optionally, a remaining portion of waste content reaching the sides of the adaptor is an amount which may be readily handled by the sealing arrangement at the wafer/adaptor interface for preventing possible waste content leakage. In some embodiments, user cleaning of the adaptor is facilitated by the reduced amount of waste content reaching the walls of the adaptor.

In some exemplary embodiments, the sealing element may include an inflatable element, for example, an annular shaped balloon, which is inflated inside the adaptor. Alternatively, the sealing element may include a compressible material adapted to exert a force against the inner walls of the adaptor. In some embodiments, the sealing element allows gas flow (flatus) through the compressible material. In some embodiments, the sealing element is annular in shape. In some embodiments, the sealing element is dimensioned to accommodate the stoma according to its dimensions. Alternatively, the sealing element includes a non-circular shape for accommodating stoma of non-circular shape.

In some exemplary embodiments, the sealing element may be used to plug the wafer port and/or the stoma for preventing waste content leaking into the adaptor from the stoma. Optionally, the plug is disposable and is unplugged from the wafer port and/or the stoma when the waste collection pouch is deployed or when the cap is removed from the adaptor. In some embodiments, the sealing element includes an absorbent material for absorbing liquid waste content flowing into the adaptor from the stoma. Additionally or alternatively, a liquid absorbing element may be included in the adaptor together with the sealing element for absorbing the liquid waste content.

In some exemplary elements, the ostomy appliance may provide for multiple types of sealing relative to the stoma. For example, one sealing type may be at the wafer/adaptor interface. Another sealing type may be at the wafer/stoma interface. Yet another sealing type may be at a cap/adaptor interface at the proximal end where the cap is attached to the adaptor. And yet another sealing type may include at an abdomen/wafer interface where the wafer is pressed against the abdomen. Optionally, sealing at the abdomen/wafer may not be a complete sealing.

In some exemplary embodiments, the sealing element may be compressible and may be made of a highly elastic material, for example, silicone rubber of durometer in a range from 1-30 Shore A, 2-20 Shore A, 2-15 Shore A, 3-10 Shore A, 3-8 Shore A. Alternatively, the sealing element may include a material that distends when in contact with a wet environment such as, for example, cotton or rayon.

An aspect of some embodiments of the present invention relates to structurally combining features such as secondary sealing and the introduction of fluids to the stomal environment. In some exemplary embodiments, the sealing element may form part of a flushing mechanism in the ostomy appliance for cleaning an interior of the adaptor and/or the peristomal skin and/or the stoma. Optionally, the flushing mechanism may be used for intestinal irrigation. In some embodiments, the sealing element fluidly connects to a valve exteriorly connected on the adaptor and through which a flushing fluid is introducible into the adaptor. Additionally, the sealing element includes a fluid distribution system having one or more inlets and one or more outlets through which the fluid flows through the sealing element into the interior of the adaptor.

Alternatively, said flushing mechanism may be formed as part of the adaptor itself instead of being included in the sealing element. Optionally or alternatively, the flushing mechanism may be formed partially as part of the adaptor and partially as part of the sealing element.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Ostomy Appliances

Exemplary Ostomy Appliance with Adaptor

Reference is now made to FIG. 1 which schematically illustrates an exploded perspective view of an ostomy appliance 100 for coupling a cap 110 to an ostomy wafer 102, according to an exemplary embodiment of the present invention. In some embodiments, appliance 100 performs the function of an adaptor permitting coupling of the wafer 102 and the cap 110 into a single ostomy stack. Additionally or alternatively, the appliance 100 may perform other functions, as detailed in subsequent sections.

Figure 2C:
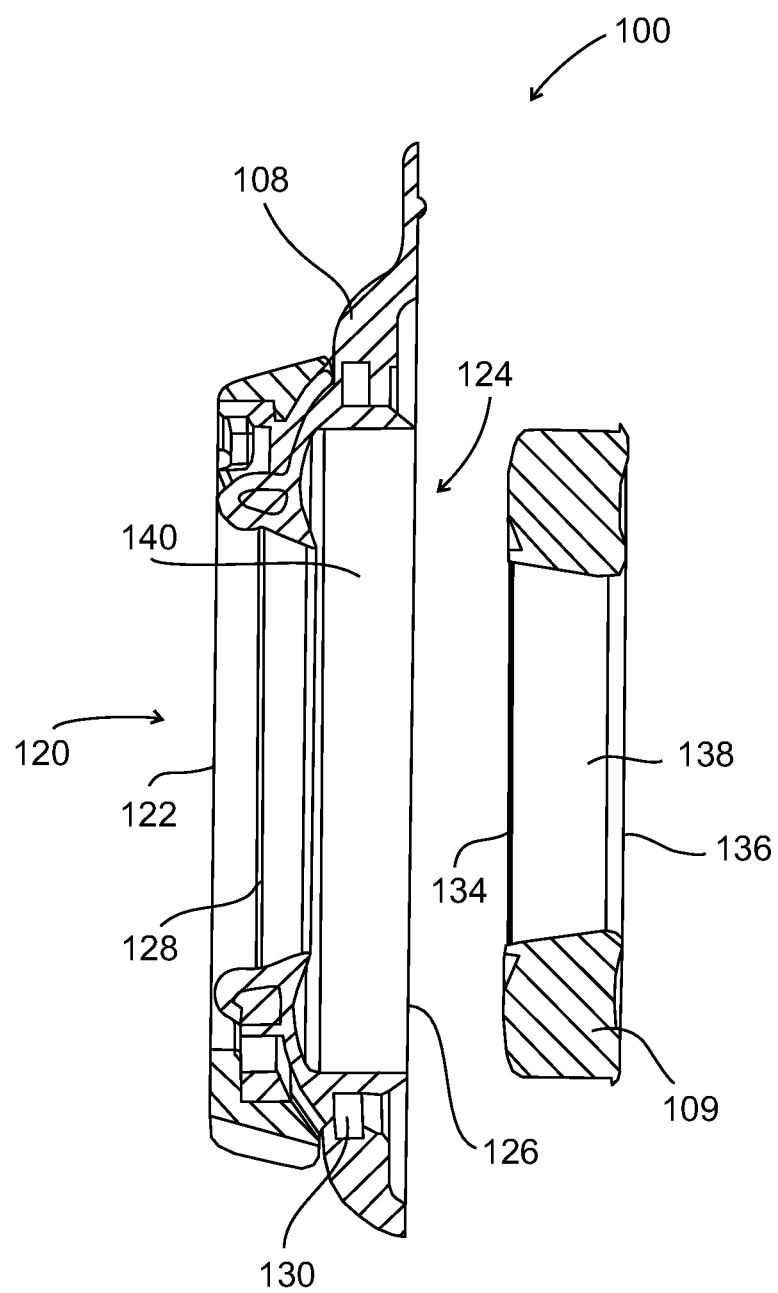
FIG. 2C schematically illustrates an adaptor and a sealing element forming part of the ostomy appliance, in accordance with an exemplary embodiment of the present invention.

Reference is also made to FIG. 2A which schematically illustrates a sectional view of ostomy appliance 100 covering a stoma 104 on a body 106, to FIG. 2B which schematically illustrates an exploded view of FIG. 2A, and to FIG. 2C which schematically illustrates an adaptor 108 and a sealing element 109 forming part of the ostomy appliance, according to an exemplary embodiment of the present invention. Optionally, wafer 102 is an ostomy wafer of a design not originally contemplated for use with an adaptor 108.

In some exemplary embodiments, adaptor 108 includes a proximal end 120 having a proximal opening 122 and a distal end 124 having a distal opening 126, the openings in fluid communication with one another. Proximal opening 122 leads into a chamber 128 adapted to accommodate a housing 112 optionally including a collapsed pouch 114. Optionally, housing 112 is part of a cap 110 which may be attached to proximal end 120. Alternatively, chamber 128 is shaped to accommodate pouch 114 without housing 112. Optionally, distal end 124 is shaped to accommodate housing 112 and/or pouch 114 in a sealing manner. Distal end 124 is adapted to abut with wafer 102 such that distal opening 126 optionally concentrically aligns with wafer port 118. In this configuration, wafer port 118 is in fluid communication with both distal opening 124 and proximal opening 122.

In some embodiments of the invention, the adaptor 108 is constructed with a minimum of internal free space when attached to wafer 102. The free space available is, for example, 1 cc, 5 cc, 10 cc, 20 cc, 30 cc, 50 cc, or any volume in between. A potential advantage of limited internal free space is limitation of the accumulation of stomal discharge, such as fecal matter, mucus, or other liquid. In some embodiments, space is minimized, for example, by the inclusion of additional material in the construction of the adaptor, beyond what is required for structural support. It should be noted that in some embodiments, space internal to adaptor 108 is occupied by another ostomy appliance component, such as a sealing element 109, an absorbing pad (related to, for example, as absorbing pad 176 of FIG. 14, hereinbelow) or another space-filling element.

In some embodiments of the invention, sealing is maintained without the application on the tissue of the stoma of direct force and/or pressure; or with low pressure, for example pressure below the 50 mmHg, below 50 mmHg, below 25 mmHg, below 10 mmHg, or below 5 mmHg. A sealing element 109 is, for example, shaped so that a minimum distance from the tissue of the stoma is ensured. This may provide an advantage by reducing the potential for tissue damage and/or for extending the appliance's usage duration.

Exemplary Adaptor Attachment Mechanism

In some exemplary embodiments, adaptor 108 further includes an attachment mechanism 130 peripherally surrounding distal opening 126 and adapted to mate with an attachment element 132, for example a flange, in wafer 102 at a wafer/adaptor interface 103.

Functions of an adaptor attachment mechanism 130 potentially include one or more of: secure coupling of an adaptor to a wafer 102, reversible coupling of an adaptor to a wafer 102, and/or sealed coupling of an adaptor to a wafer 102.

In some embodiments, attachment element 132 is a pouch attachment element of a type generally found in existing wafers and onto which a rim to an opening in an existing waste content collection pouch is generally attached. A mating arrangement between attachment mechanism 130 and flange 132 is configured for preventing waste content leakage therethrough, and potentially includes use of an elastomeric seal and/or other sealing element yielding at least primary-type sealing, for example against the outflow of stomal gasses. In some embodiments, the mating arrangement between attachment mechanism 130 and flange 132 potentially prevents undesired detachment of adaptor 108 from wafer 102, and includes use of a snap-fit mechanism, a twist-and-lock mechanism, or other suitable locking mechanism. Optionally, the mating arrangement allows detachment when desired.

Exemplary Sealing Element

In some exemplary embodiments, ostomy appliance 100 includes a sealing element 109 which is directed toward secondary sealing that reduces interior access of wastes to tissue and ostomy appliance surfaces, and in some embodiments also participates in primary sealing against leakage from the ostomy appliance. Sealing element 109 has a first opening 134, an opposing second opening 136, and a passage 138 fluidly communicating both openings. Functions of a sealing element 109 include, for example, one or more of: providing a second seal to supplement sealing against waste leakage provided by the wafer 102 itself and/or by attachment mechanism 130; occupying a space between the stoma and the adaptor's body, limiting the accumulation of fecal matter in the adaptor; and providing absorbency to contain waste leakage so that it does not contaminate other elements or surfaces of the ostomy stack, and/or other functions as herein described.

Sealing element 109 is optionally configured for being inserted into a cavity 140 between chamber 128 and distal opening 126 such that second opening 136 aligns with wafer port 118. Optionally, sealing element 109 is reversible and fittable inside cavity 140 with first opening 134 aligned with wafer port 118. Optionally, insertion of sealing element 109 into cavity 140 is done by a user of ostomy appliance 100. Alternatively, said insertion is done during the device assembly and adaptor 108 is provided to the user with sealing element 109 already inserted into cavity 140. Optionally, the user can remove sealing element 109, for example for cleaning it or for replacing it with a new sealing element. Alternatively, sealing element 109 is permanently attached adaptor 108 within cavity 140. In some embodiments, sealing element 109 is annular shaped as shown. In some embodiments, its geometrical shape is non-annular for corresponding with a geometrical shape of cavity 140. Optionally, its geometrical shape corresponds with that of stoma 104 and/or wafer port 118 without putting pressure on stomal tissue.

In some embodiments, sealing element 109 is made of a highly compressible material such as for example, silicone rubber or thermoplastic elastomer, of durometer in a range from 1-30 Shore A, 2-20 Shore A, 2-15 Shore A, 3-10 Shore A, 3-8 Shore A. Optionally, the elasticity and structure of sealing element 109 are chosen such that sealing element 109 is compressible against wafer 102 at a wafer/stoma interface 105 when adaptor 100 is attached to flange 132. Optionally, the compression force between sealing element 109 and wafer 102 at wafer/stoma interface 105 is high enough to ensure a reliable sealing and prevent waste content and/or flushing fluid leakage therethrough. In some embodiments, the compression force ranges from 100 grams to 5 kg, for example, 200 grams, 500 grams, 1 kg, 2 kg, 3kg, 4.5 kg. In some embodiments, sealing element 109 is compressibly fitted inside cavity 140. Optionally, a pressure required for maintaining sealing element 109 inside the adaptor without resorting to use of an adhesive material ranges from 0.1 psi to 2 psi, for example, 0.15 psi, 0.3 psi, 0.5 psi, 0.8 psi, 1 psi, 1.5 psi, 1.8 psi. Alternatively, sealing element 109 is made of a distending material for absorbing liquid waste content flowing from stoma 104, optionally through wafer port 118, and expanding within cavity 140. In some embodiments, sealing element 109 provides for a second sealing mechanism in ostomy appliance 100 additional to that provided at wafer/adaptor interface 103. Optionally, sealing at wafer/stoma interface 105 enhances the sealing provided by wafer/adaptor interface 103 by reducing a possible amount of waste leakage and/or flushing liquid reaching the wafer/adaptor interface. Optionally, the sealing mechanisms at wafer/stoma interface 105 and wafer/adaptor interface 103 act as redundant system. In some embodiments, an amount of liquid waste content absorbable by sealing element 109 is up to 100 ml, for example, 1 ml, 5 ml, 10 ml, 20 ml, 35 ml, 45 ml, 50 ml, 60 ml, 75 ml, 85 ml, 90 ml, 95 ml. Optionally, sealing element 109 is able to absorb amounts of liquid waste content in excess of 100 ml, for example, 120 ml, 150 ml, 180 ml, 200 ml, or more. More details on some embodiments of sealing element 109 are discussed in greater detail further on in this disclosure.

Exemplary Ostomy Cap

In some embodiments, cap 110 includes housing 112 accommodating collapsed pouch 114. Potential functions of a cap include, for example, preventing the constant flow of waste from the stoma, indicating the build-up of pressure from waste, allowing waste to flow upon sensing a sufficient pressure or upon action by the user, acting as a container for a pouch 114 which deploys to collects the waste and/or other functions as herein described.

Alternatively, pouch 114 is accommodated in cap 110 externally to housing 112. Collapsed pouch 114 is optionally deployable by removing a lid 116 on cap 110 and manually extracting the pouch by the user. Alternatively, pouch 114 is deployed following removal of lid 116 by the pressure of waste content flowing from stoma 104 into adaptor 108 and pushing on the pouch. In some embodiments, lid 116 is manually removable by the user. Alternatively, lid 116 is automatically removed by the pressure pushing on the lid. In some embodiments, lid 116 is a pressure sensing lid which flexibly bulges outwards or stiffens or a combination thereof responsive to a pressure from waste content. Optionally, lid 116 bulges outwards responsive to a gas pressure inside adaptor 108.

Exemplary Ostomy Appliance with Direct Cap Attachment

Figure 2D:
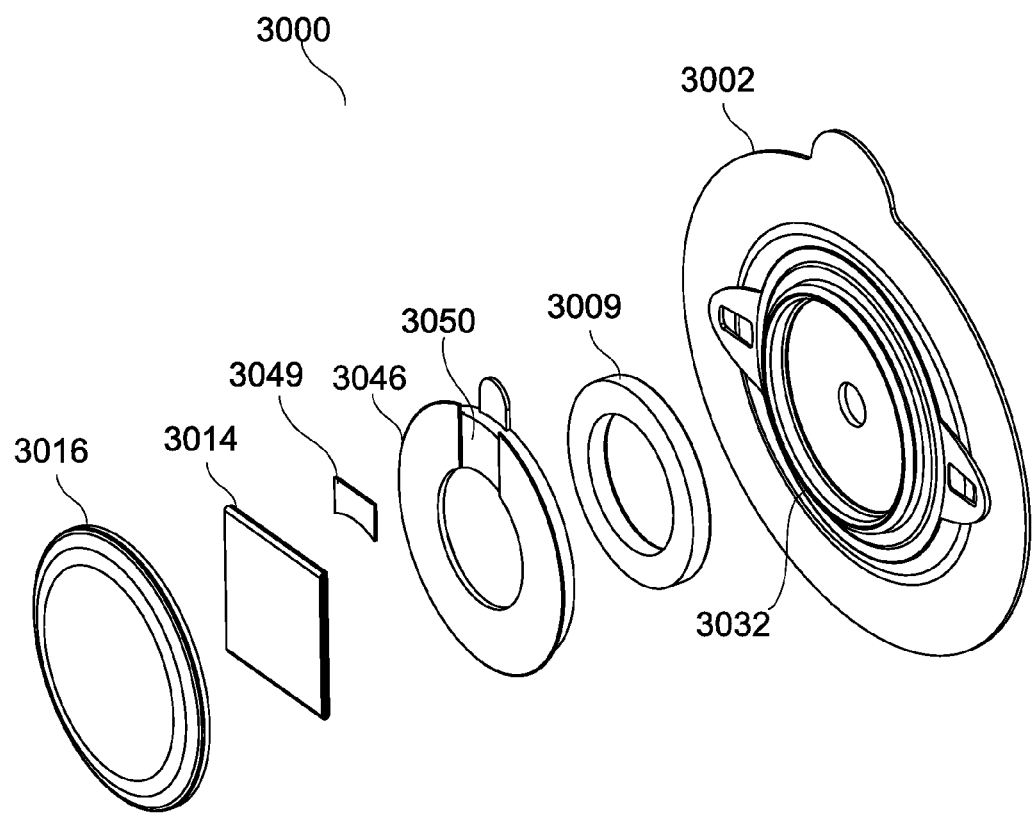
FIG. 2D schematically illustrates an exploded perspective view of an ostomy appliance for coupling a cap to an ostomy wafer, in accordance with an exemplary embodiment of the present invention.
Figure 2E:
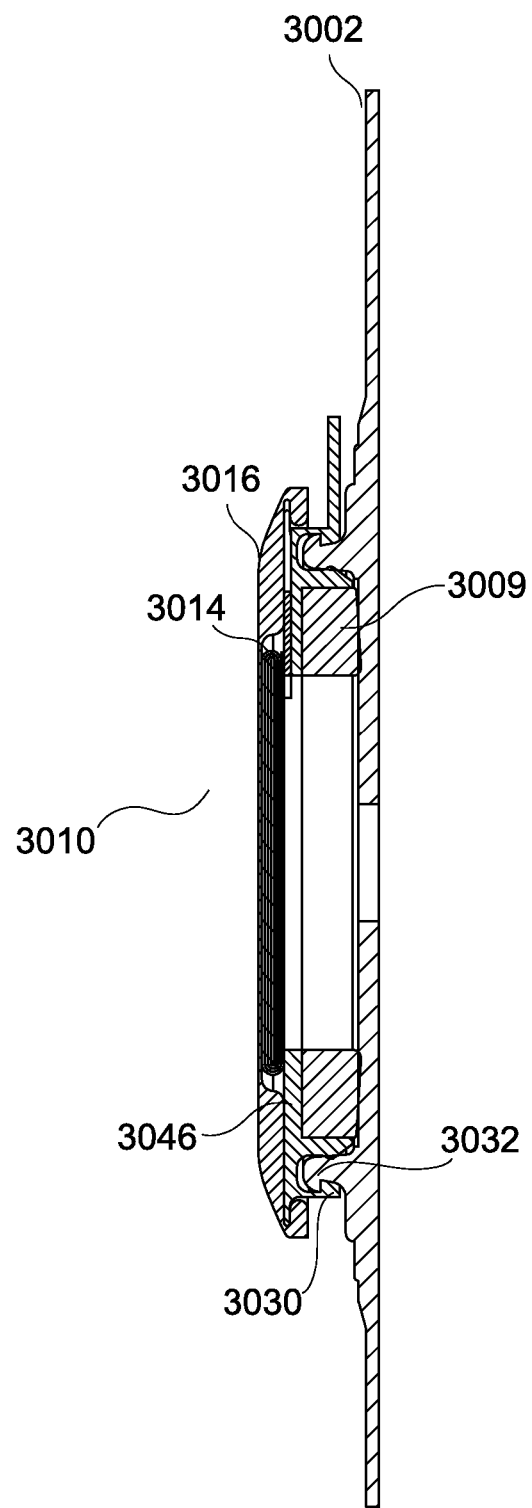
FIG. 2E schematically illustrates an cross sectional view of the ostomy appliance of FIG. 2D, in accordance with an exemplary embodiment of the present invention.

Reference is now made to FIGS. 2D and 2E which schematically illustrate an exploded perspective view and a cross sectional view, respectively, of an ostomy stack 3000 representing some embodiments of the invention, in which a cap 3010 is coupled to an ostomy wafer 3002, according to an exemplary embodiment of the present invention. Considered in overview, potential advantages of the embodiments represented here include, for example, a low ostomy stack profile, a simplified stack assembly procedure for the user, a low production cost, and/or elastic flexibility of the ostomy stack. Other possible advantages will be described in connection with additional specific features of exemplary ostomy stack 3000.

The cap 3010 includes an attachment mechanism 3030 which attaches to an attachment element 3032 of the wafer. Optionally, the attachment element 3032 is a flange. Optionally, the attachment mechanism 3030 is integrally formed with the cap housing 3046 so as to form a ring which is held in place by the flange 3032.

Figure 2F:
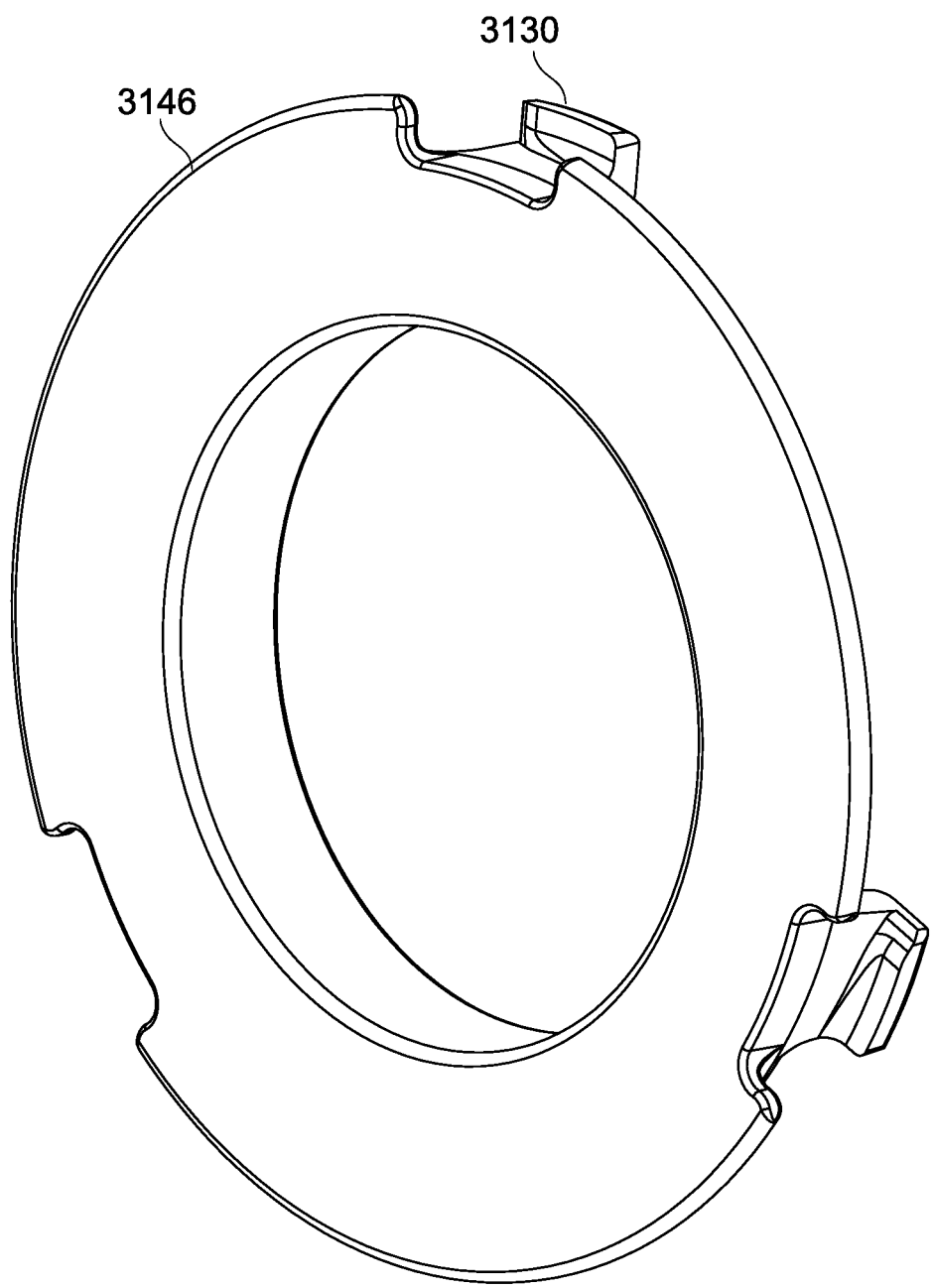
FIG. 2F schematically illustrates a perspective view of the housing and attachment mechanism of an ostomy appliance cap, in accordance with exemplary embodiments of the present invention.
Figure 2G:
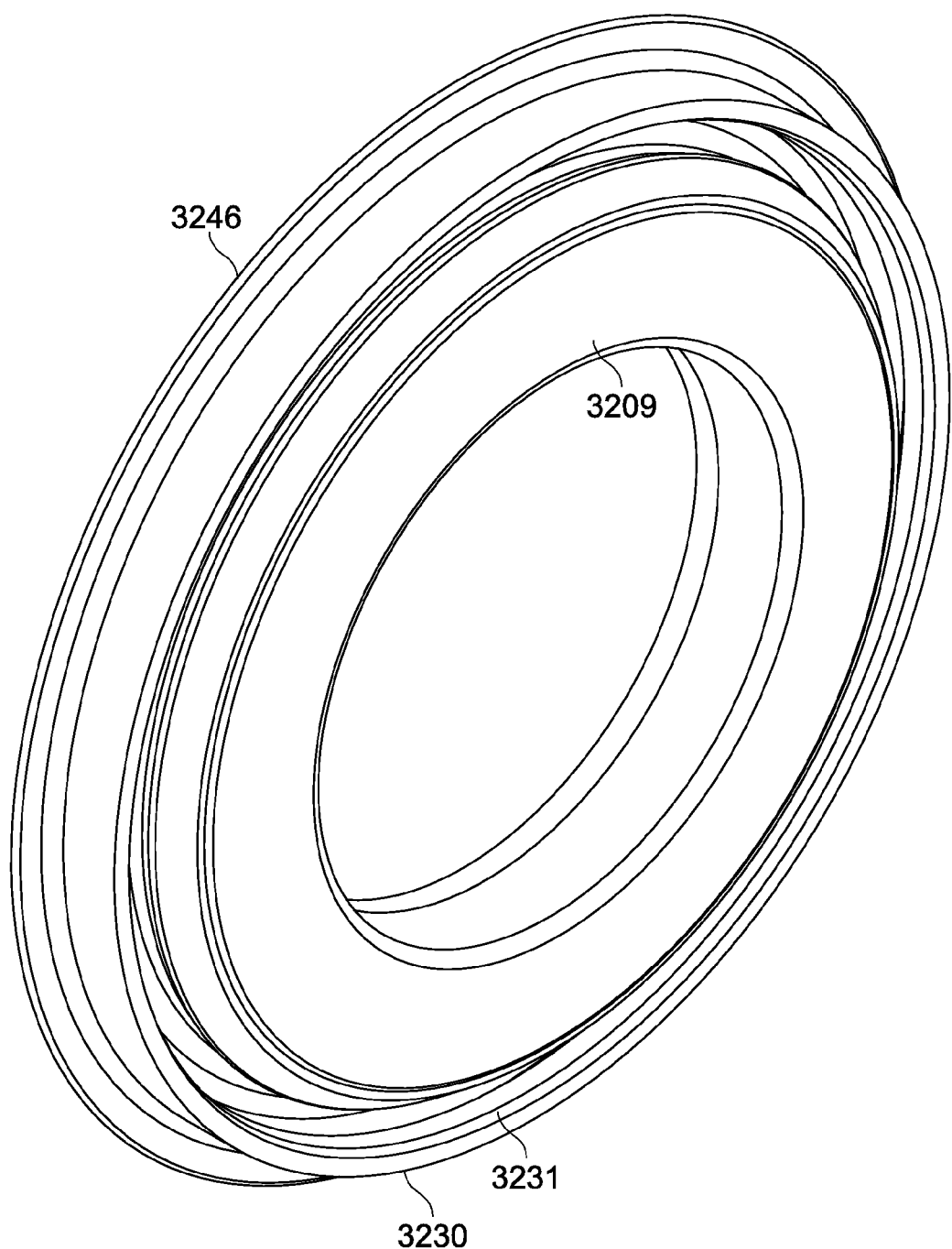
FIG. 2G schematically illustrates a perspective view of the housing, sealing element, and attachment mechanism of an ostomy appliance cap, in accordance with exemplary embodiments of the present invention.
Figure 2H:
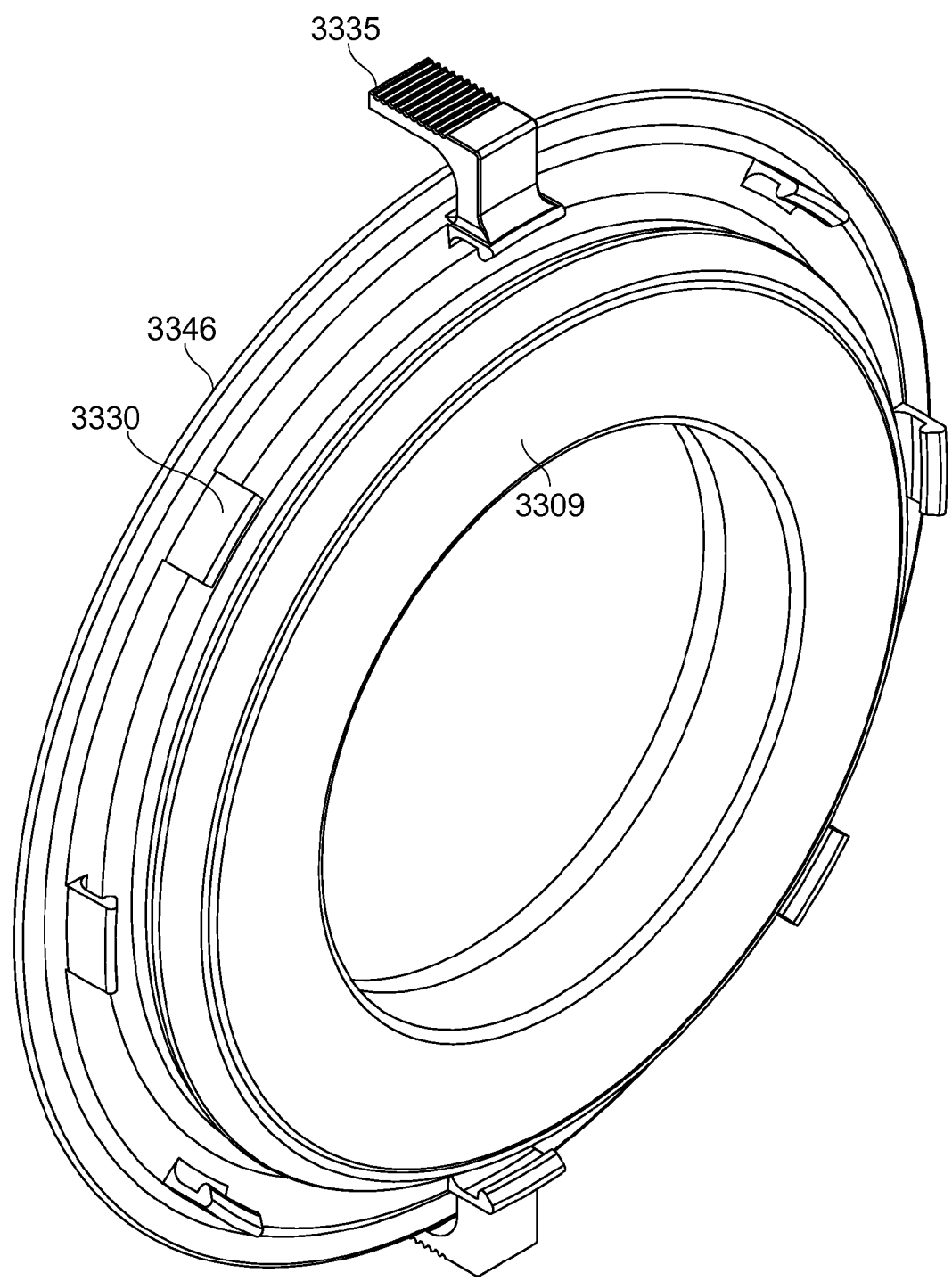
FIG. 2H schematically illustrates a perspective view of the housing, sealing element, and attachment mechanism of an ostomy appliance cap, in accordance with exemplary embodiments of the present invention.

In FIGS. 2F, 2G, and 2H, alternative exemplary attachment mechanisms are shown in schematic perspective view, demonstrating an exemplary variety of the attachment designs which are contemplated, as will now be described.

In FIG. 2F, attachment mechanism 3130 comprises a plurality of flanged tabs. In the example shown, the flanges are positioned to protrude outward from the center of the cap housing 3146. The tabs are optionally constructed of a rigid or semi-rigid plastic, with elasticity sufficient to bend in order to engage or disengage with attachment elements on the ostomy wafer (not shown). Additionally or alternatively, said attachment elements on the ostomy wafer bend or otherwise distort in order to engage or disengage with the tabs. Optionally, the flanged tabs are integrally formed with the cap housing 3146.

In FIG. 2G, an exemplary attachment mechanism 3230 comprises a circumferential rim, overhanging a circumferential recess 3231 and designed to engage with an ostomy wafer's flange (not shown) by a snap-fit mechanism operating around the circumference of cap housing 3246. The material used to form this attachment mechanism 3230 is optionally flexible, such as silicone rubber or TPE, and optionally has durometer in the range of 30-80 Shore A. A sealing element 3209 may thereby be held against an ostomy wafer with sufficient force to resist the leakage of material issuing from the stoma. Sealing element 3209 is directed toward secondary sealing, and in some embodiments also participates in primary sealing. Additionally or alternatively, circumferential recess 3231 might, for example, be replaced with a flange, and a mating recess put on the ostomy wafer. Potentially, the use of attachment designs compatible with flexible housings for ostomy components enables the construction of wholly flexible ostomy appliances with features including, for example, manual and/or automatic gas release control, and collapsed waste collection pouches with pressure sensing release. A flexible ostomy appliance potentially provides advantages for user comfort and/or resistance to detachment during body movements.

In FIG. 2H, an exemplary attachment mechanism comprises a plurality of flanged tabs 3330. The tabs 3330 are optionally constructed of a rigid or semi-rigid plastic, with elasticity sufficient to bend in order to engage or disengage with attachment elements on the ostomy wafer (not shown). Additionally or alternatively, said attachment elements on the ostomy wafer bend or otherwise distort in order to engage or disengage with the tabs. In the example shown, the flanges are positioned to protrude inward toward the center of the cap housing 3346. The flanges are optionally wedge-shaped on one side, and flat on the other.

By means of their shape and elasticity, the tabs 3330 are optionally constructed so as to rise out of the way when pressed down over a projecting flange on an ostomy wafer, and yet engage firmly behind it once in place, providing sufficient force to hold sealing element 3309 (a secondary sealing-directed element with a potential role in primary sealing) sealingly against the ostomy wafer. Optionally, the ostomy wafer is provided with suitably arranged apertures into which the flanges of the ostomy cap insert. Optionally, the apertures or holding flange are on the cap housing, in order to mate with flanged tabs on the ostomy wafer. Optionally, and with suitable complementary changes as required to cap and ostomy wafer, the inward- and outward-pointing direction of flanges are reversed. Optionally, a projection protrudes from at least one flanged tab 3335, for example, extending proximally so that it is accessible from the proximal side of the device, such that deflecting the projection causes the flange to bend outward. This provides a potential advantage for easier release of cap from the wafer.

In some embodiments of the invention, attachment of components is by adhesive bonding. In an exemplary embodiment of the invention, adhesive is applied by a user to at least one of two ostomy components to be attached, for example a proximal surface of wafer 3002, and the second component, for example, ostomy cap housing 3046, is placed over it. A potential advantage arises from using an adhesive that can be applied so as to provide a volume for one of the components to sink into, such as a foamed adhesive. A voluminous adhesive potentially allows adhesive attachment over a larger surface area. A voluminous adhesive potentially encases a portion of one or both components, providing adhesion resistant to multiple directions of force. In an alternative embodiment, the at least one of two ostomy components is supplied to the user with an adhesive already applied and covered by a release liner. In this case the user first removes the liner and then attaches the surfaces to one another to create an airtight sealing therebetween. Optionally, both components are provided with a self-adhesive material. A potential advantage is obtained by the use of an adhesive with a short time to setting well enough to maintain the components in place under at least their own weight, for example, a setting time of less than five seconds, less than ten seconds, or less than twenty seconds.

In some embodiments of the invention, the above principles and elements of attachment mechanism are used alone or in combination, and with suitable modifications in the specifics of shape or material apparent to those skilled in the art, to achieve attachment of the ostomy cap to the ostomy wafer. With suitable modifications of attachment elements, according to the embodiment of the invention, attachment of an ostomy cap to an ostomy adaptor, or of an ostomy adaptor to an ostomy wafer, is achievable. With suitable modifications of attachment elements, according to the embodiment of the invention, attachment of a lid or a pouch restraint to a more distal component of the ostomy stack is achievable. In some embodiments, a greater, lesser, or intermediate number of tabs is used than the 3-8 tabs shown, for example 2, 4, 6, 10 or more. In some embodiments, a greater, lesser, or intermediate spacing or width of the tabs is used than shown; for example, tabs occupying the entire attachment circumference apart from the gaps which separate them, or 50%, or 10%. In some embodiments, greater, lesser, or intermediate tab length or flange depth is used than shown, in correspondence with the design of complementary structures which hold or receive them.

Returning again to FIGS. 2D and 2E, the attachment interface is sealed by sealing element 3009, which is optionally held within a cavity of the cap housing 3046.

Further exemplary features of the ostomy stack potentially useful for controlling and directing the release of waste, or for improving user comfort or convenience are potentially implemented as now described.

Optionally, a collapsed pouch 3014 is attached to the cap, and sealed to it, for example, by bonding (adhesive or chemical) or welding. A lid 3016 restrains the bag in its collapsed state.

The collapsed pouch 3014 is optionally configured into a low profile package, for example by folding. Optionally, the collapsed pouch is stored at or near the proximal end of the cap housing 3046.

A low profile pouch package provides a potential advantage by requiring less thickness to be added to the protruding profile of the ostomy appliance, either proximal or distal to the pouch. The ostomy appliance is potentially less obtrusive thereby. The ostomy appliance is potentially easier to carry and/or store thereby.

A proximal storage configuration of the pouch potentially provides an advantage by allowing more of cavity of the cap housing 3046 to be available, for example, to accommodate protrusion of the stoma (not shown).

Optionally, cap housing 3046, lid 3016, and/or ostomy wafer 3002 are made in whole or in part of flexible materials (for example, material as previously described herein in connection to flexible adaptors and caps). Construction from flexible material potentially provides advantages such as, for example, allowing the ostomy stack to conform more easily and/or with minimal discomfort to the shape and/or motion of the body of the user.

Optionally, a filter 3049 is integrated into the cap 3010. Optionally, the cap housing 3046 is designed with an aperture 3050 sized to hold the filter.

A filter potentially provides an advantage by allowing stomal gasses to passively escape during wearing of the ostomy appliance, instead of building up behind the seals of the ostomy appliance. On the other hand, a filter potentially provides an advantage by reducing the likelihood of this escape from happening in a sudden or uncontrolled fashion. The filter potentially provides the advantage of allowing such gasses to escape while controlling the leakage of fluid and solid material. The filter potentially provides the advantage of allowing stench-forming components of gasses to be filtered from the emission.

Embedding the filter within an aperture of the cap housing potentially provides an advantage by requiring less thickness to be added to the protruding profile of the ostomy appliance in order to accommodate it. An advantage is potentially provided by having the proximal face of the filter flush with a proximal face of the cap housing, thus easing the assembly of a pouch onto both faces in a sealing manner.

Exemplary Embodiment Of Adaptor With Threaded Cap

Figure 2I:
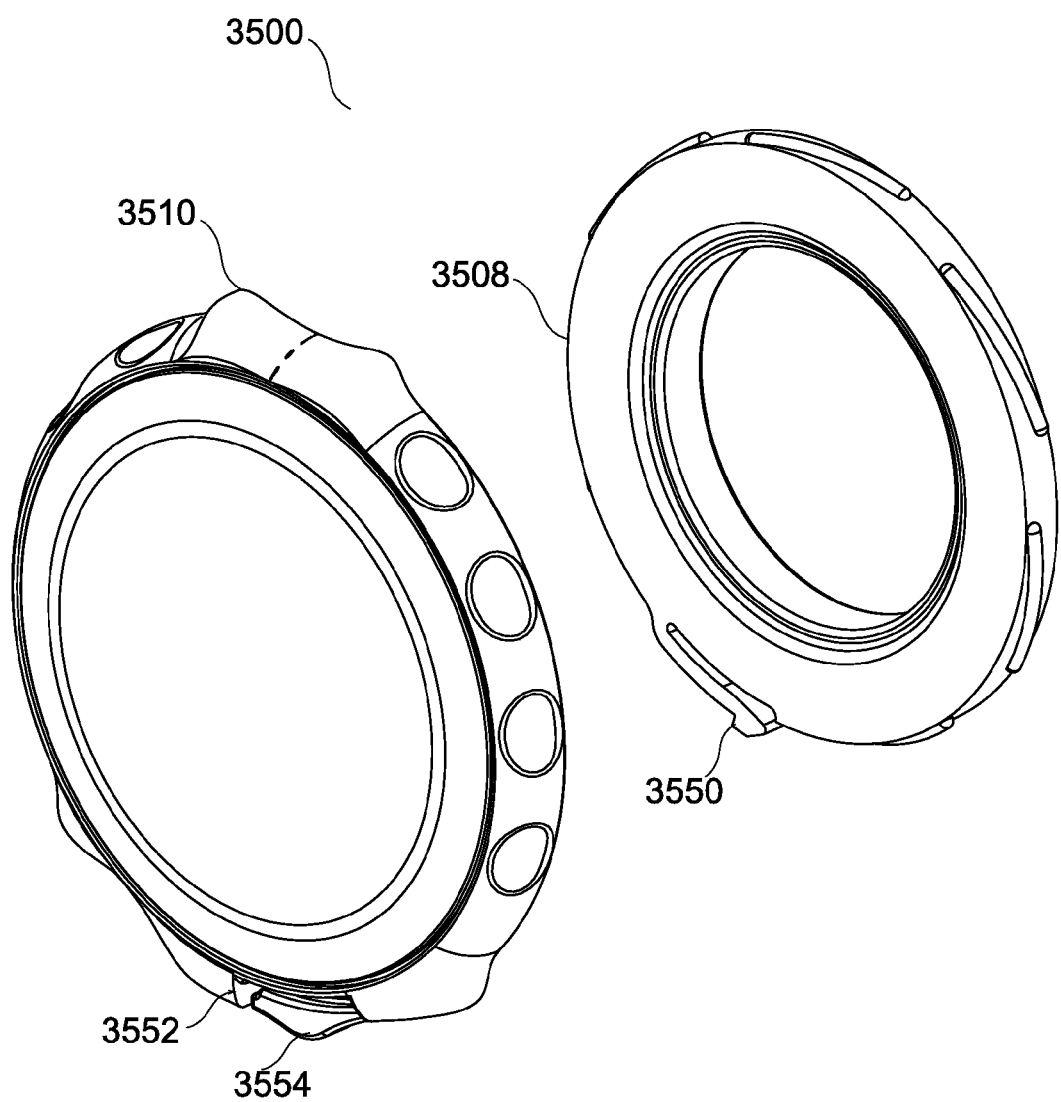
FIG. 2I schematically illustrates an exploded perspective view of an ostomy assembly coupled by threaded attachment, in accordance with exemplary embodiments of the present invention.
Figure 2J:
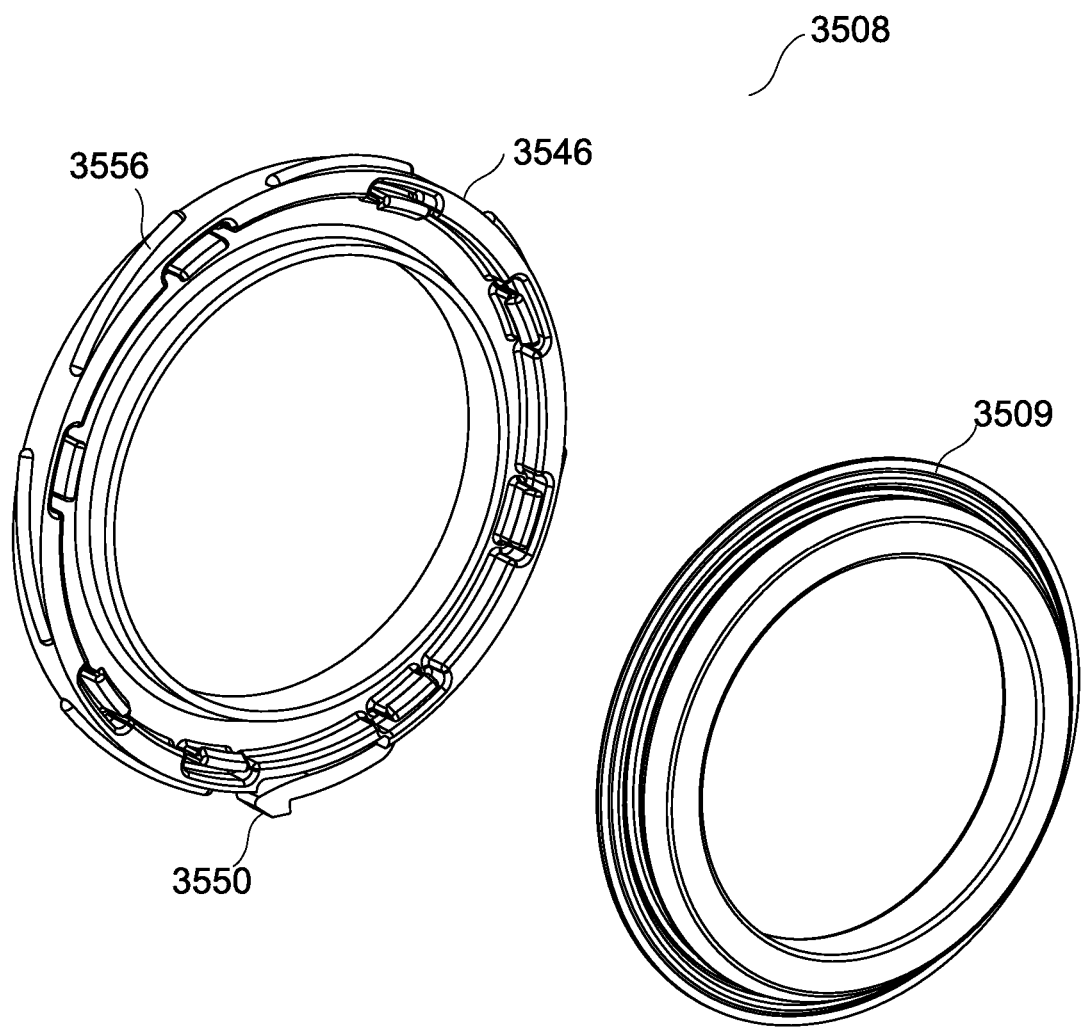
FIG. 2J schematically illustrates a perspective view of the adaptor component of the ostomy assembly of FIG. 2I, in accordance with exemplary embodiments of the present invention.
Figure 2K:
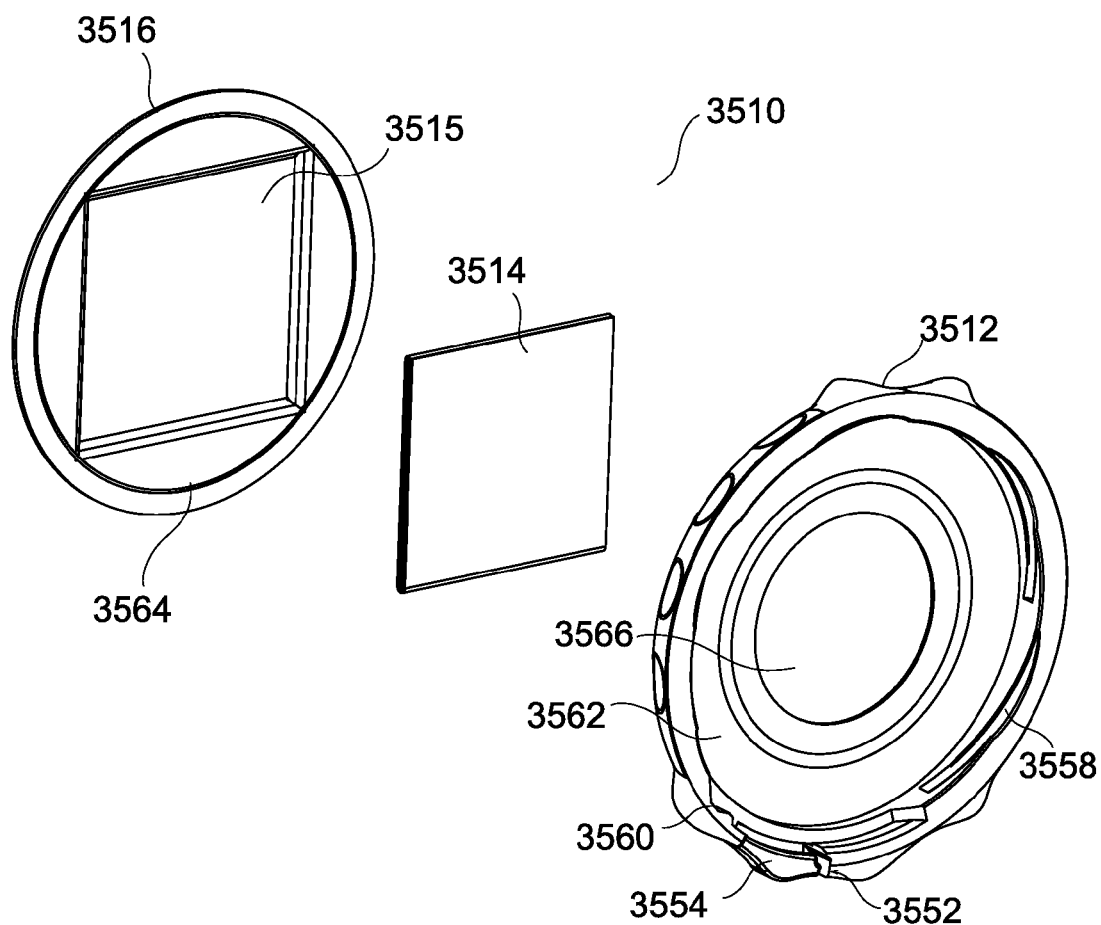
FIG. 2K schematically illustrates a perspective view of the cap component of the ostomy assembly of FIG. 2I, in accordance with exemplary embodiments of the present invention.

Reference is now made to FIGS. 2I, 2J, and 2K, which schematically illustrate exploded perspective views of an adaptor 3508 and cap 3510 which together comprise an ostomy assembly 3500 coupled by threaded attachment. Considered in overview, potential advantages of the embodiments represented here include, for example, one or more of reduced force, particularly reduced pressing force, required to assemble the ostomy stack on the body; an ostomy stack profile which is minimally elevated above the height required to accommodate a protruding stoma; and/or reduced cost of manufacturing ostomy stack components.

In some embodiments of the invention, adaptor 3508 is provided with threading, 3556, configured to interlock its housing 3546 with complementary threading 3558 on the housing 3512 of cap 3510. Optionally, adaptor 3508 is further provided with a lever 3550 that prevents unwanted detachment of cap 3510 by interfering with a surface 3552 of the cap housing 3512, configured into the housing. Optionally, the housing 3512 is provided with a recess, 3560, configured to receive a portion of the lever when the adaptor 3508 and cap 3510 are fully coupled. Optionally, a catch 3554 is provided which, when depressed, bends the lever 3550 so that it no longer interferes with surface 3552, allowing the cap 3510 to rotate and be removed from the adaptor 3508.

The locking and unlocking mechanism comprised of lever 3550 and interfering surface 3552 may provide the advantage of preventing the cap 3510 from detaching unexpectedly from the adaptor 3508. Embodiments including recess 3560 potentially provide the advantage of giving tactile and/or auditory feedback to the user as the lever springs into it, indicating that the cap 3510 has been securely fastened. Embodiments where the mechanism is further comprised of catch 3554 allow mechanical advantage and/or a broader surface area to be applied to the bending of lever 3550, overcoming the lock more easily than by direct pressure on lever 3550 itself.

The use of a rotating motion to securely couple cap 3510 to adaptor 3508 may provide an advantage for patients sensitive to abdominal pain—for example, as may occur during recovery after a surgery—by reducing the need to push inward on the abdomen. The mechanical advantage obtained by using a rotating motion to secure a threaded attachment mechanism 3556 and 3558 may serve to assist patients lacking the strength to press-fit ostomy stack components together. The wide gripping surface provided by the rotating cap housing 3512 may provide an advantage by reducing the number of fine motor movements required to assemble ostomy stack components on the body. Said wide gripping surface may also provide an advantage by reducing the torque required for fastening the cap onto the adaptor.

In some embodiments of the invention, a waste pouch 3514 is provided which attaches to cap housing 3512, and has an opening disposed to receive waste flowing through aperture 3566 in the cap. Optionally, the pouch is collapsed. Optionally, the pouch is collapsed by being folded into a low-profile package. Optionally, the collapsed pouch is restrained from deploying by a lid 3516. The lid 3516 may be secured to cap housing 3512, for example by means of a connecting element 3564, which may be a flange. The connecting element 3564 may mate to a complementary connecting element (not shown) of the cap housing 3512.

In some embodiments of the invention, the connecting element 3564 is designed so as to self-release upon a certain pressure being exerted on lid 3516. This self-release may be, for example, by means of a deformation of the material of the lid under the force of internal pressure. In embodiments where the lid restrains a collapsed pouch, self-release also allows the pouch 3514 to deploy, so that it can receive waste.

A self-releasing lid 3516 may provide an advantage by preventing excessive buildup of internal pressure and/or material behind the ostomy appliance. Such buildup, if unrelieved, might lead, for example, to leakage of one of the ostomy appliance seals and/or to formation of intestinal blockage.

In some embodiments of the invention, lid 3516 is constructed with a cavity 3515, sized to hold the collapsed pouch 3514.

A lid 3516 with a cavity 3515 may, by reducing one thickness requirement of the ostomy appliance, provide the advantage of lowering the protruding profile of the overall ostomy appliance. Alternatively, it may provide the advantage of allowing additional internal space, for example to accommodate tissue protruding from a stoma, or to accommodate other ostomy appliance elements.

In some embodiments of the invention, the lumen of adaptor 3508 contains a sealing element 3509, a secondary sealing-directed element with a potential role in primary sealing. Optionally, sealing element 3509 is attached to adaptor housing 3546 by welding or bonding (adhesive or chemical). Optionally, sealing element 3509 is molded onto adaptor housing 3546 by over-molding or two-shot molding. Optionally, sealing element 3509 may be made of a soft elastomer, for example silicon rubber, or a thermoplastic elastomer, for example SEBS. The durometer of sealing element 3509 is, for example, between 5-20 Shore A.

In some embodiments of the invention, a cap surface 3562 is forced up against a sealing element 3509 of the adaptor when cap 3510 and adaptor 3508 are fully coupled. Optionally, the parts of the locking mechanism may be disposed so as to allow a degree of rotation sufficient to adjust the resistance of the seal to the flow of gas, without the rotational lock being overcome. Optionally, sealing element 3509 may also provide secondary sealing by a pressing of its distal surface against surface of an ostomy wafer (not shown) or the body of the user (not shown), and resisting the flow and/or leakage of waste.

The seal between cap surface 3562 and sealing element 3509 may provide the advantage of ensuring that waste entering the lumen of the adaptor continues through the aperture 3566 of the cap housing 3512 to pouch 3514, instead of leaking to the exterior of the ostomy appliance. A selective lowering in the resistance of the seal allows internal gasses to escape more quickly, which may provide an advantage, for example, to reduce user discomfort due to built-up pressure, or to prevent self-release of the lid 3516. Because the gas flow resistance is selectable, flow of liquid and solid waste may be relatively restricted, or prevented. The use of a single sealing element 3509 to provide sealing at both its distal and proximal ends may provide the advantage of a reduced cost by using an integral element for both functions. The integration of sealing element 3509 with the housing 3546 of the adaptor 3508, for example by over-molding or two-shot molding during manufacture may provide a further advantage of reduced cost.

Exemplary Embodiment of Adaptor with Rotary Slider

Figure 3:
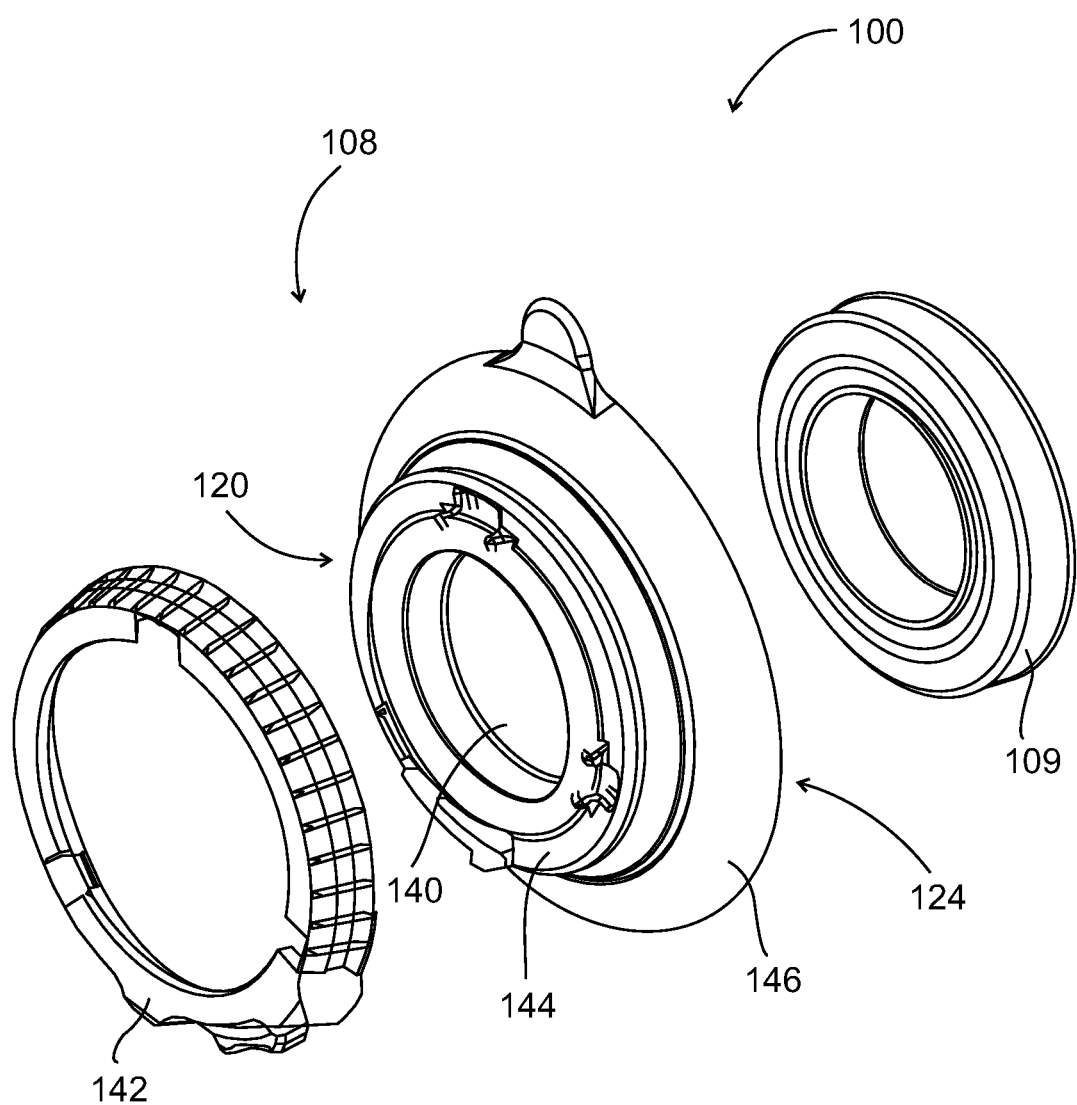
FIG. 3 schematically illustrates an exploded perspective view of adaptor and sealing element, in accordance with an exemplary embodiment of the present invention.

Reference is now also made to FIG. 3 which schematically illustrates an exploded perspective view of adaptor 108 and sealing element 109, according to an exemplary embodiment of the present invention. In overview, the rotary slider attachment mechanism shown illustrates, for example, that use of a rotating motion to couple ostomy components may be achieved by placing the rotating part on the more distal component of those being coupled. It also illustrates how tab restraint may be augmented with a rotary motion.

Adaptor 108 includes a rotary slider 142, a fixation ring 144, and an adaptor body 146. Fixation ring 144 is shaped, for example with recesses, to receive attachment elements of an overlying cap, for example tab 3130. Rotary slider 142 is shaped, for example, with notches to allow passage of tabs 3130 into fixation ring 144. Rotary slider 142 serves as a cover which rotatably fits onto fixation ring 144 which is fixedly attached to adaptor body 146 on proximal end 120. In some embodiments, rotary slider 142, fixation element 144, and adaptor body 146 mechanically resemble cover 108, fixation ring 110, and stomal cover 102 disclosed in the aforementioned WO 2011/138727 by the applicant. Optionally, rotary slider 142, fixation element 144, and adaptor body 146 functionally resemble the aforementioned cover 108, fixation ring 110, and stomal cover 102 in WO 2011/138727. Sealing element 109 fits into cavity 140 through distal end 124. In some embodiments, fixation ring 144 is an integral component of adaptor body 146.

Exemplary Ostomy Appliance and Gas Release Mechanisms

Exemplary Adaptor With Rotary Slider And Gas Release

Figure 4A:
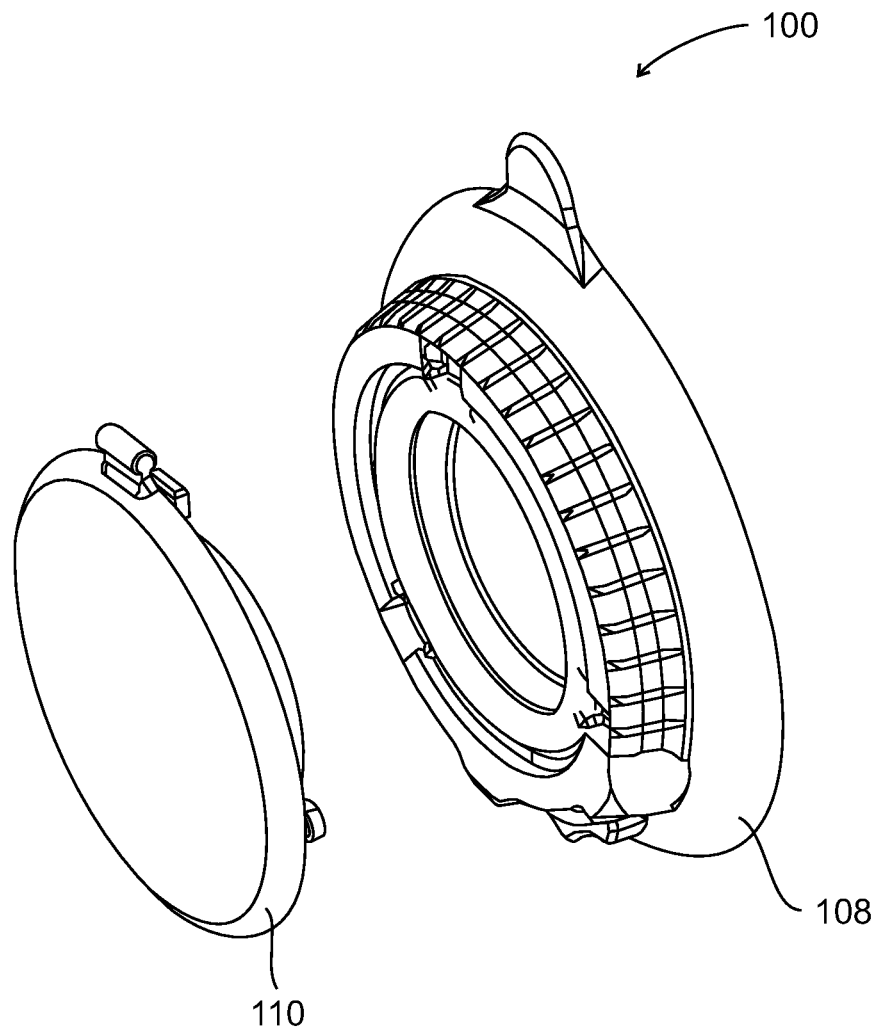
FIG. 4A schematically illustrates a partial-exploded perspective view of the cap and the adaptor in the ostomy appliance having an optional gas release mechanism, in accordance with an exemplary embodiment of the present invention.
Figure 4B:
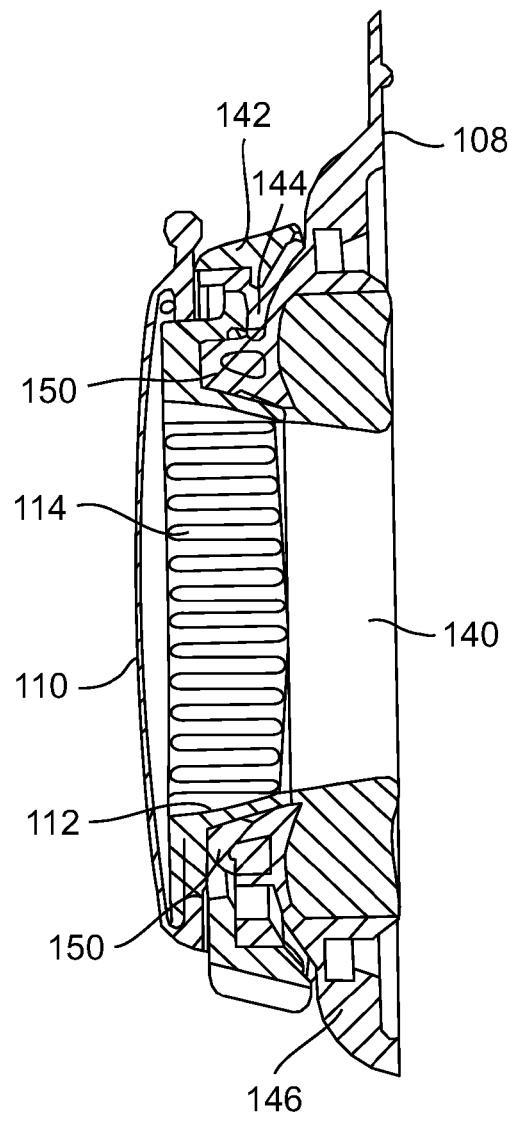
FIGS. 4B and 4C schematically illustrate sectional views of the cap fitted onto the adaptor, the latter showing a gas flow path between the cap and the adaptor as part of the gas release mechanism, in accordance with some exemplary embodiments of the present invention.
Figure 4C:
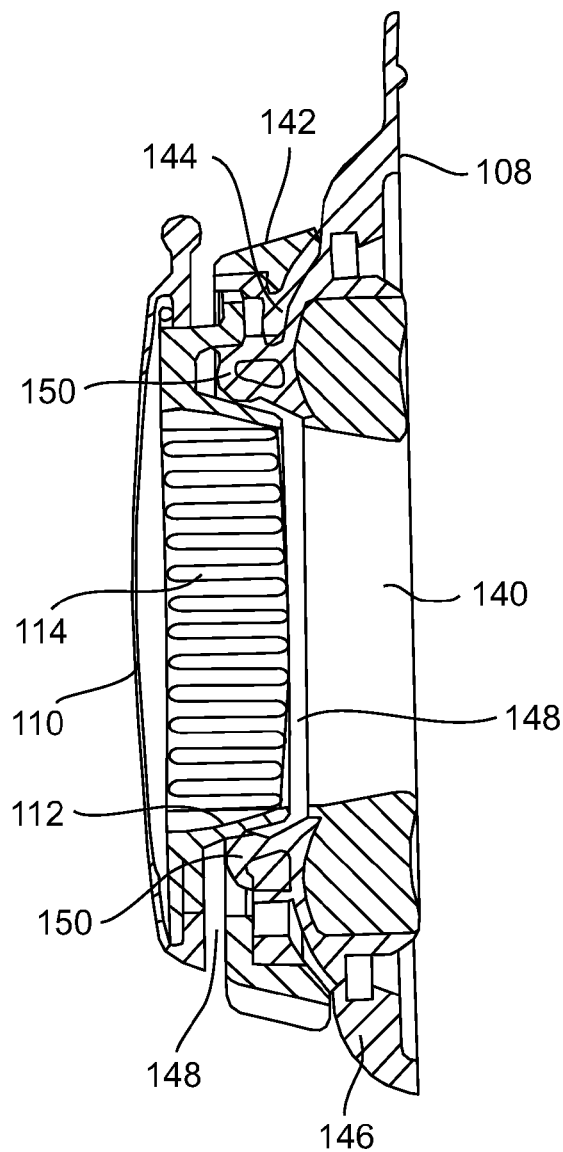

Reference is now also made to FIG. 4A which schematically illustrates a partial-exploded perspective view of cap 110 and adaptor 108 in ostomy appliance 100 having an optional gas release mechanism, according to some exemplary embodiments of the present invention. Reference is also made to FIGS. 4B and 4C which schematically illustrate sectional views of cap 110 fitted onto adaptor 108, the latter showing a gas flow path 148 between the cap and the adaptor as part of a gas release mechanism, according to some exemplary embodiments of the present invention. In FIG. 4B, cap 110 seals cavity 140 for preventing waste contents and gas from escaping from stoma 104 (not shown in the figure) through adaptor 108. In FIG. 4C, cap 110 is displaced away from cavity 140 for releasing gas while preventing waste content from leaking out from adaptor 108. In some embodiments, adaptor body 146 in adaptor 108 includes a seal 150 similar to seal 138 in the aforementioned document by the applicant.

In some exemplary embodiments, gas release through gas flow path 148 is performed in a similar fashion as described in the aforementioned WO 2011/138727 by the applicant. Optionally, a mechanical interaction of cap 110, rotary slider 142, fixation ring 144, and adaptor body 146 including seal 150 for opening gas flow path 148 is similar to that of cap 106, cover 108, fixation ring 110, and stomal cover 102 including seal 138 in the aforementioned document by the applicant.

Exemplary Low Profile Adaptor with Rotary Slider and Gas Release

Figure 4D:
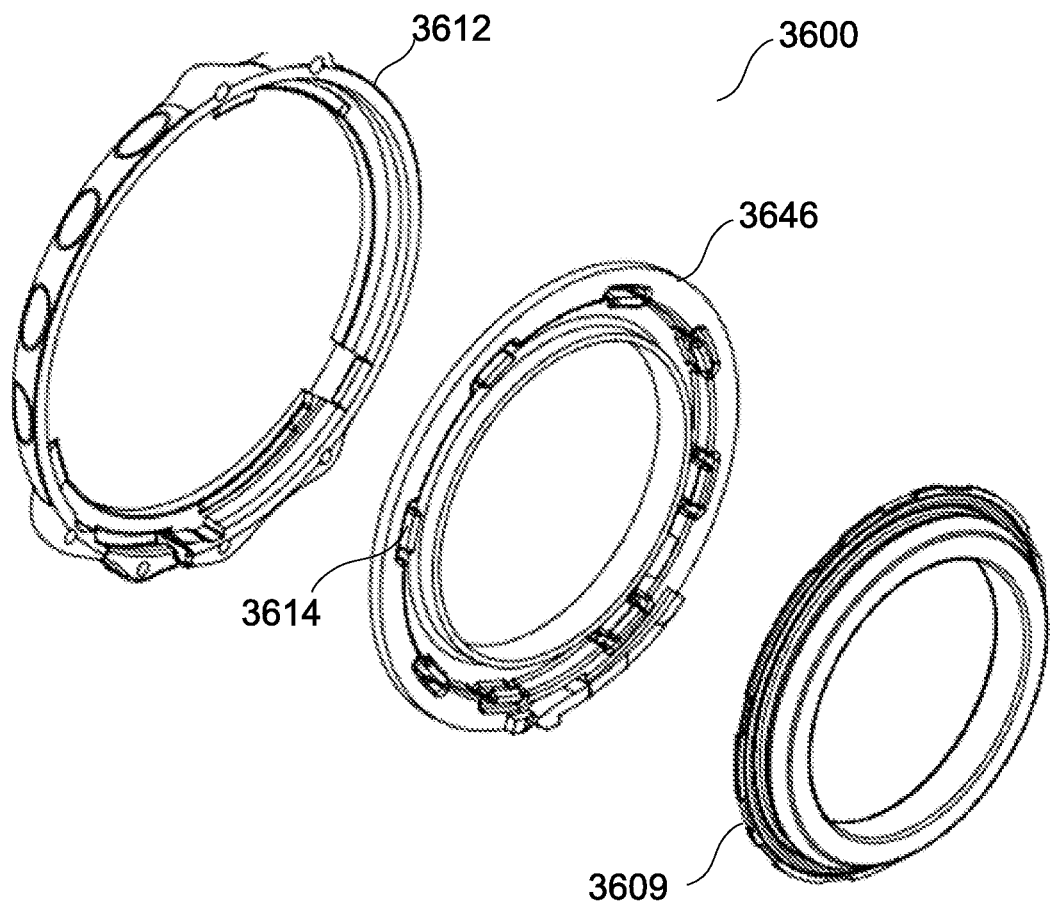
FIG. 4D schematically illustrates an exploded perspective view of a low-profile ostomy adaptor with rotary slider, in accordance with exemplary embodiments of the present invention.
Figures 4E, 4F:
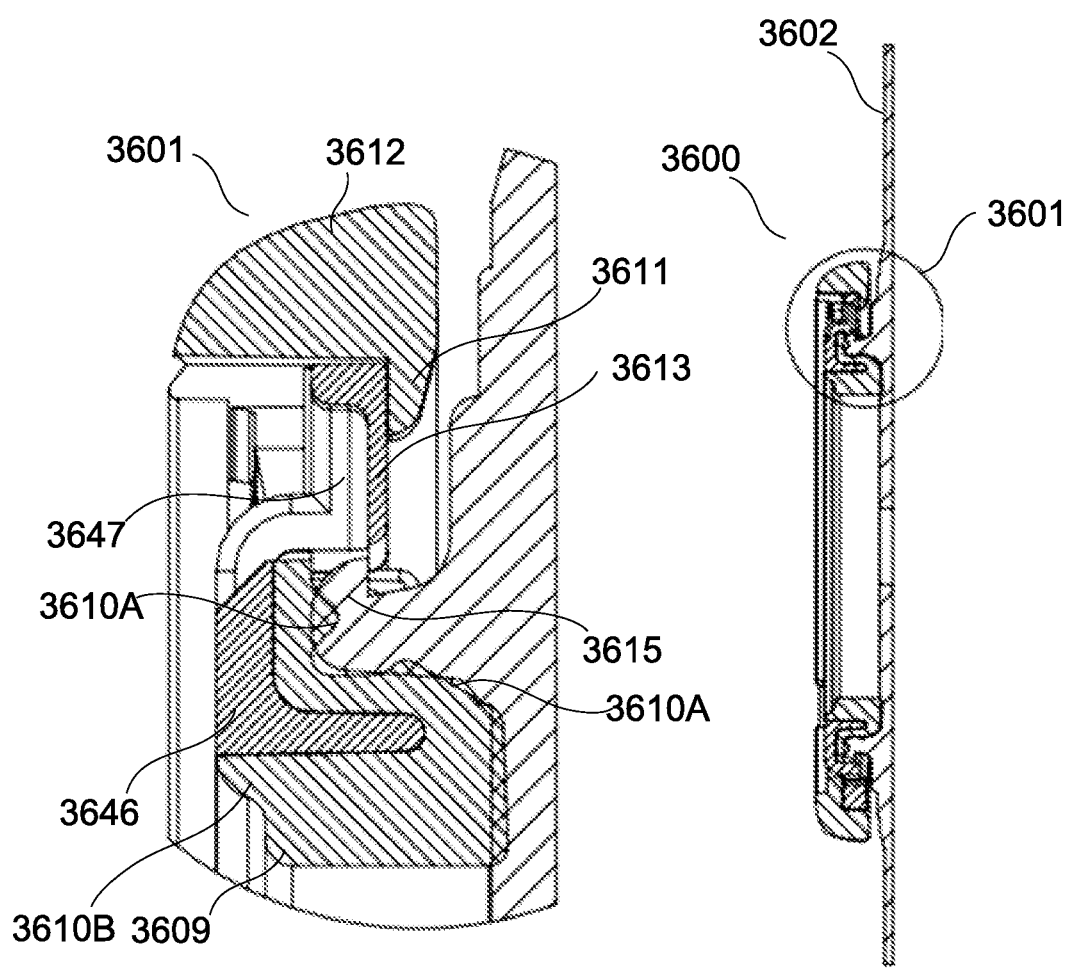
FIG. 4E schematically illustrates a cross sectional view of the assembled ostomy adaptor of FIG. 4D, in accordance with exemplary embodiments of the present invention.
FIG. 4F schematically illustrates a detailed cross sectional view of the assembled ostomy adaptor of FIG. 4D, in accordance with exemplary embodiments of the present invention.

Reference is made now to FIGS. 4D, 4E, and 4F, which schematically illustrate a low profile ostomy appliance adaptor in exploded perspective view (FIG. 4D), in cross section attached to an ostomy wafer (FIG. 4E), and in detailed cross section attached to a ostomy wafer (FIG. 4F), according to some embodiments of the invention.

In overview, these drawings illustrate, for example, how a rotary slider located on the distal member of two coupled ostomy stack components may be designed so that it contributes minimal additional height to the assembled ostomy stack. As will now be detailed for this embodiment, the lowered height is optionally achieved by putting the elements which receive the connecting elements of the ostomy cap (not shown) outside the perimeter of the connecting mechanism of the ostomy wafer. This allows them to be located closer to the body, without, for example, interfering with a protruding stoma, and/or with secondary sealing.

A potential advantage of this design relates to manufacturing cost, which may be lowered, compared, for example, to embodiments corresponding to FIG. 3. The parts are compatible with a two-shot injection manufacturing process, which reduces the need for more expensive manufacturing steps.

For the user, a potential advantage may arise from lowered cost itself. A lowered user cost may also open for a user possibility of more frequent changing of device components. This can reduce the need for cleaning. Potentially, the user will also enjoy a higher sense of hygiene.

In some embodiments of the invention, adaptor 3600 comprises an adaptor housing 3646 coupled to a rotary slider 3612. Sealing element 3609 is fitted to adaptor housing 3646. Optionally, sealing element 3609 is attached to adaptor housing 3646, for example by chemical bonding or welding. Optionally, sealing element 3609 is molded onto adaptor housing 3646 by over-molding or two-shot molding. In some embodiments sealing element 3609 is a secondary sealing-directed element with a potential role in primary sealing.

In some embodiments of the invention, rotary slider 3612 is attached to adaptor housing 3646 by means of tabs 3611 configured to interfere with rim 3613 of adaptor housing 3646, such that rotary slider 3612 can rotate around its axis but not move in the axial direction. In some embodiments, the height of all ostomy components together is no more than 12 mm above the level of the wafer. In some embodiments, the height of all ostomy components together is no more than 6 mm above the level of the wafer. For many ostomates, this may be near to the minimal height available, since a typical stoma rises between 5 mm and 10 mm above the skin.

In some embodiments of the invention, a cap (not shown) is attached to adaptor 3600, for example, in accordance with attachment elements, design, and principles described in connection to cap 110 and adaptor 108, with suitable modifications.

Optionally, gas release may be achieved by means similar to that described in connection to cap 110 and adaptor 108 in FIGS. 4A and 4B.

In some embodiments of the invention, adaptor housing 3646 is made of rigid plastic, for example polyamide or polypropylene. In some embodiments of the invention, sealing element 3609 is made of soft elastomer, for example silicone rubber.

Optionally, sealing element 3609 is made of thermoplastic elastomer, for example SEBS. The durometer of the sealing element is may be, for example, between 5-20 Shore A.

In some embodiments of the invention, adaptor housing 3646 attaches to the wafer's flange 3615, for example by means of attachment tabs 3614 that snap onto the flange's circumferential rim 3615.

In some embodiments of the invention, adaptor housing 3646 includes recesses 3647 configured to accommodate fixation tabs, for example the attachment mechanism 3130 of cap housing 3146 (FIG. 2F). The recesses 3647 are external to the wafer's attachment flange 3615, to remove potential interfering with tissue or secondary sealing within the ostomy stack cavity.

In some embodiments of the invention, adaptor rim 3613 and recesses 3647 are positioned externally to the wafer's flange 3615 lowering the protruding profile of the adaptor 3600. Optionally, the number of tabs provided is suited to stabilizing the corresponding increase in the diameter of the adaptor, for example 6 or 8 tabs, or more.

In some embodiments of the invention, sealing element 3609 includes one or more bumps 3610A configured to press against wafer flange 3615 when the adaptor 3600 is attached to wafer 3602.

In some embodiments of the invention, sealing element 3609 includes one or more bumps 3610B configured to press against a surface of an installed cap, for example, cap housing 3146.

In some embodiments of the invention, pressing bumps 3610A and 3610B on the sealing adaptor 3609 provides the advantage of improved sealing force.

Another Exemplary Ostomy Appliance with Gas Release Mechanism

Figure 5A:
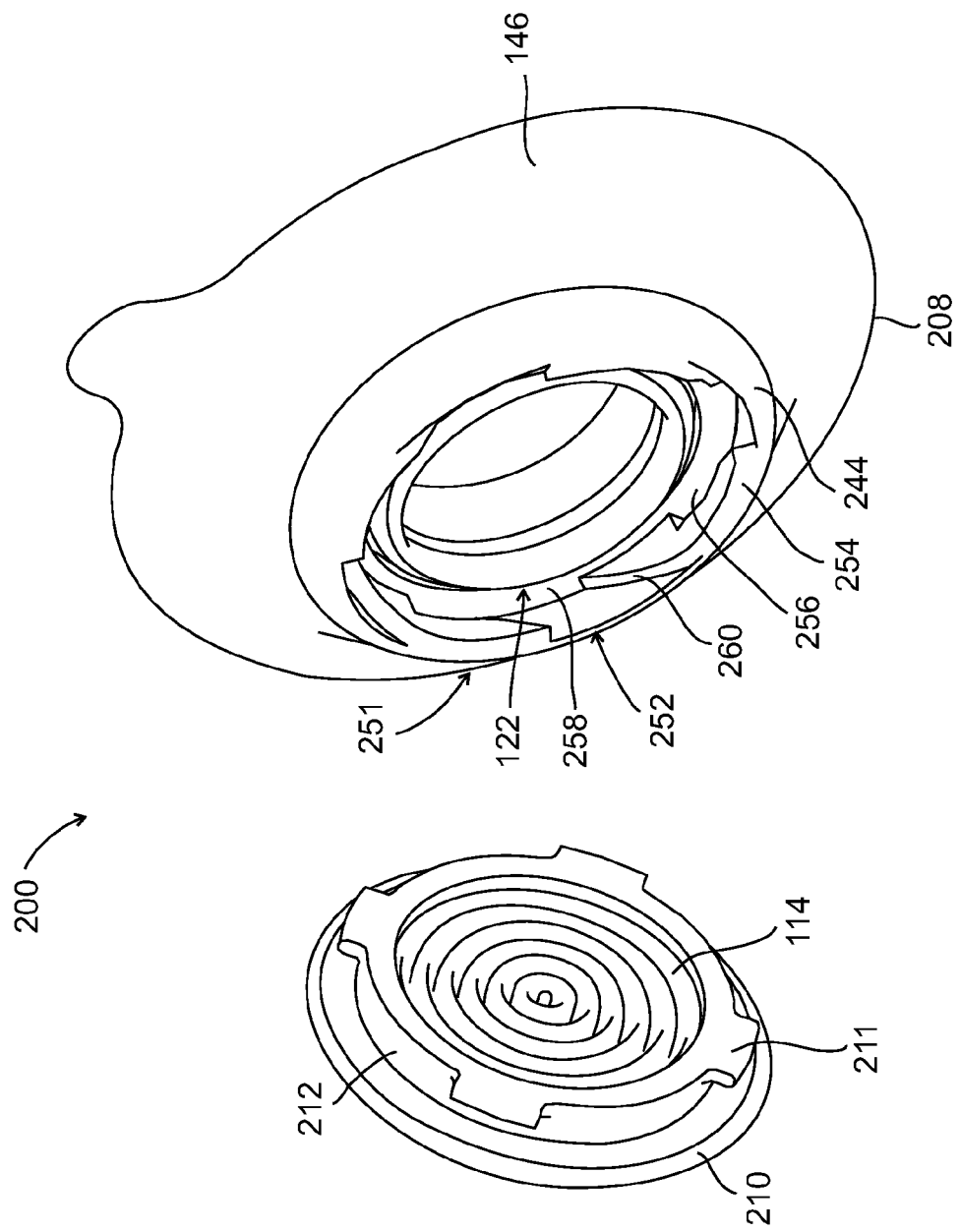
FIG. 5A schematically illustrates a perspective view of an adaptor and a removable cap included in a ostomy appliance having an optional gas release mechanism, in accordance with some exemplary embodiments of the present invention.
Figure 5B:
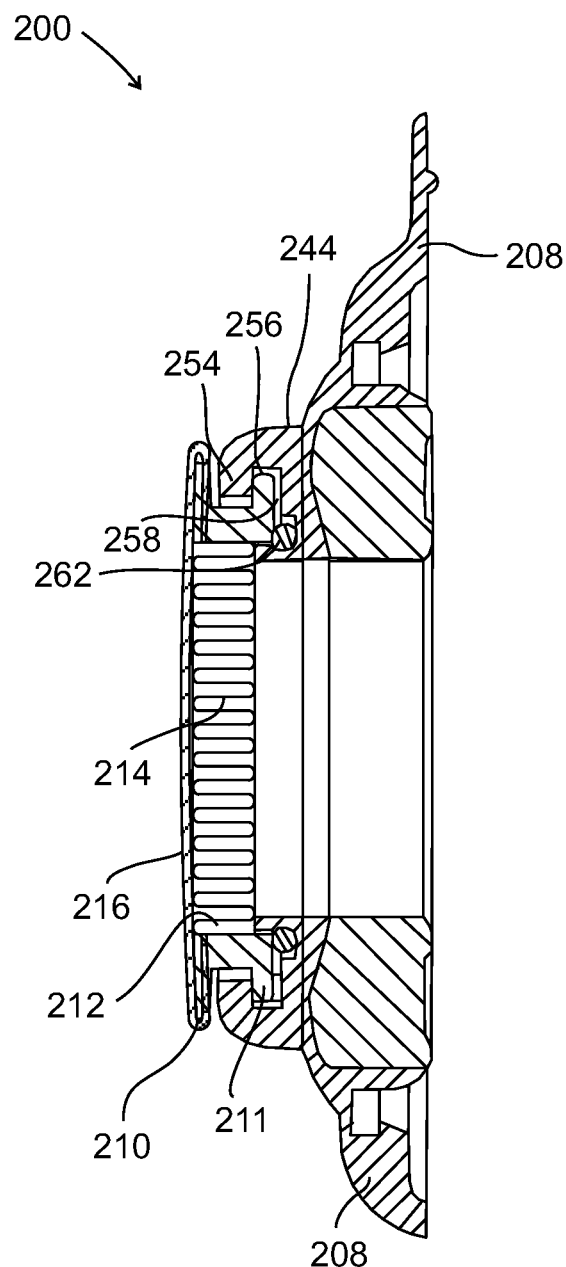
FIG. 5B schematically illustrates a sectional view of an ostomy appliance having an optional gas release mechanism, in accordance with some exemplary embodiments of the present invention.

Reference is now made to FIG. 5A which schematically illustrates a perspective view of an adaptor 208 and a removable cap 210 included in an ostomy appliance 200 having an optional gas release mechanism, and to FIG. 5B which schematically illustrates a sectional view of the ostomy appliance, according to some exemplary embodiments of the present invention.

In some exemplary embodiments, cap 210 includes a housing 212 with a collapsed pouch 214 and a removable lid 216. Optionally, lid 216 is similar to lid 116.

In some embodiments, cap 210 is a smart cap. In some embodiments, cap 210 additionally includes one or more tabs 211, for example 4 tabs as shown, radially extending from a distal end of housing 212. Tabs 211 are configured for locking cap 210 onto a fixation ring 244 attached to adaptor body 146. Optionally, fixation ring 244 is an integral component of adaptor body 146.

In some exemplary embodiments, fixation ring 244 includes one or more cap locking mechanisms 251 into which tabs 211 are inserted for locking cap 210. Cap locking mechanism 251 includes a lock opening 252, a rim 254, and a lock slot 256. Cap 210 is locked in fixation element 244 by inserting tab 211 through lock opening 252 until the tab abuts a ledge 258 peripherally surrounding opening 122. Optionally, ledge 258 is an integral component of fixation element 244. Alternatively, ledge 258 is a surface portion of adaptor body 146 peripherally surrounding opening 122. Following abutment, cap 210 is rotated for sliding tab 211 under a lock rim 254 until the tab engages lock slot 256. In some embodiments, lock rim 254 includes an inclined rim portion 260 for guiding tab 211 through lock opening 252. In some embodiments, fixation ring 244 includes a lock seal 262 peripherally surrounding ledge 258. Lock seal 262, which may be an elastomeric seal, for example in the shape of a gasket adapted to be compressed by cap 210 when tab 211 is inserted in lock slot 256, for providing sealing against waste content leakage and gas leakage. In some embodiments, partial rotation of cap 210 partially retrieves tab 211 from lock slot 256, reducing the compressive force exerted on lock seal 262, and allowing a small gap to be opened suitable for release of gas while preventing waste content leakage.

Figure 6A:
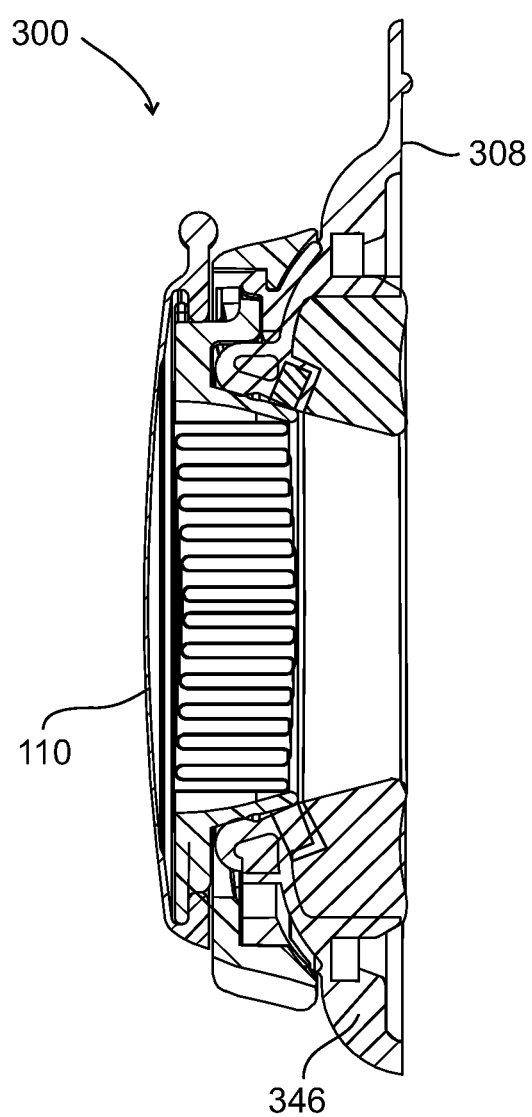
FIGS. 6A and 6B schematically illustrate sectional views of a cap fitted onto an adaptor, the latter showing a gas flow path through a gas filter between the cap and the adaptor as part of a gas release mechanism, in accordance with some exemplary embodiments of the present invention.
Figure 6B:
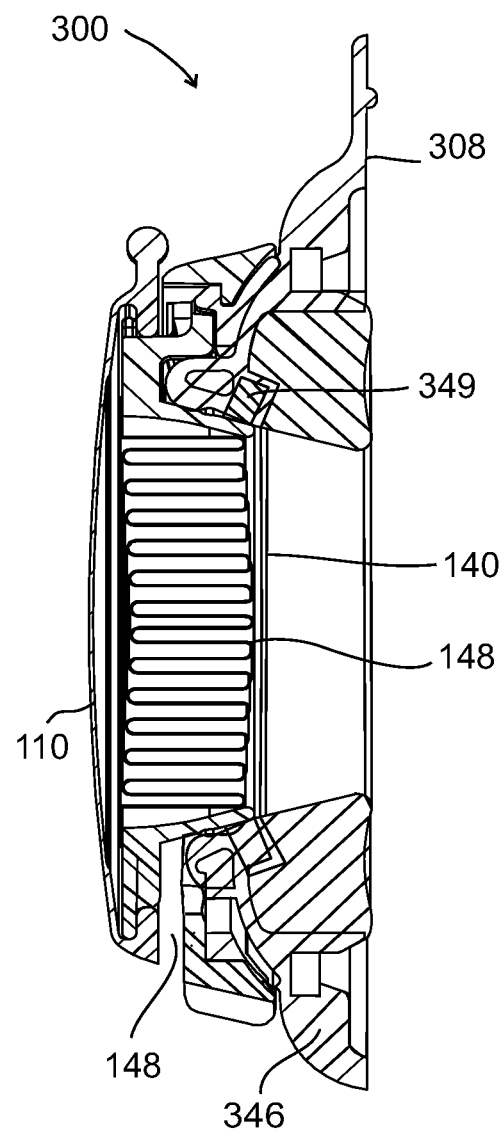

Reference is made to FIGS. 6A and 6B which schematically illustrate sectional views of cap 110 fitted onto an adaptor 308, the latter showing a gas flow path 148 through a gas filter 349 between the cap and the adaptor as part of a gas release mechanism, according to some exemplary embodiments of the present invention.

In FIG. 6A, cap 110 seals cavity 140 for preventing waste contents and gas from escaping from stoma 104 (not shown in the figure) through adaptor 108. In FIG. 6B, cap 110 is displaced away from cavity 140 for releasing gas while preventing waste content from leaking out from adaptor 108. In some embodiments, adaptor body 346 in adaptor 308 includes a gas filter 349 for filtering gas flow through gas flow path 148.

In some exemplary embodiments, a gas release mechanism described in WO 2011/138727 by the applicant is used with gas flow path 148.

Another Exemplary Ostomy Appliance with Gas Release

Figure 7B:
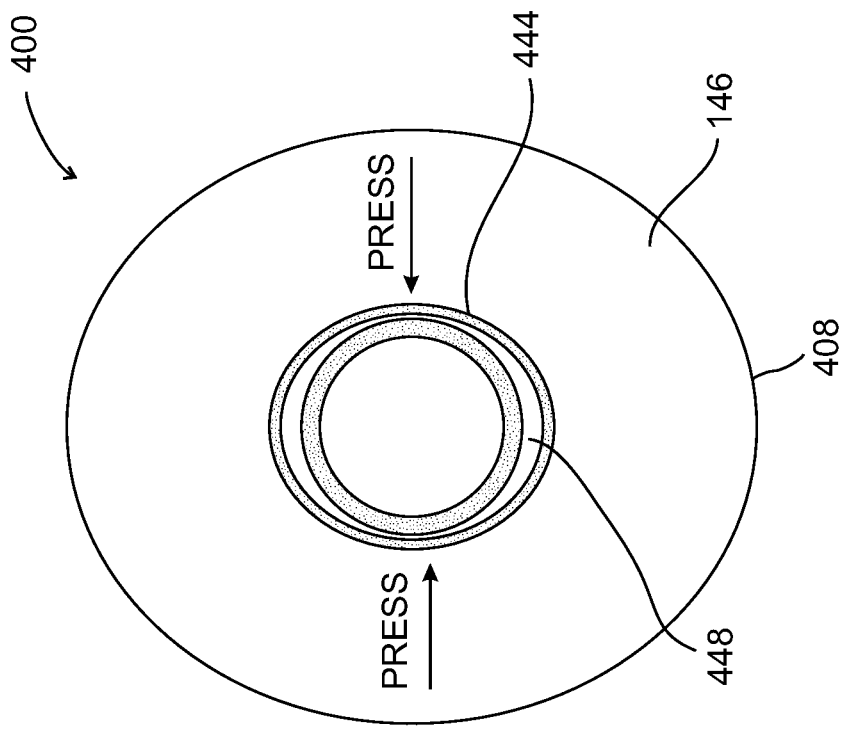
FIG. 7B shows a front view of the adaptor with the flexible fixation ring in a gas release mode, in accordance with some exemplary embodiments of the invention.
Figure 7A:
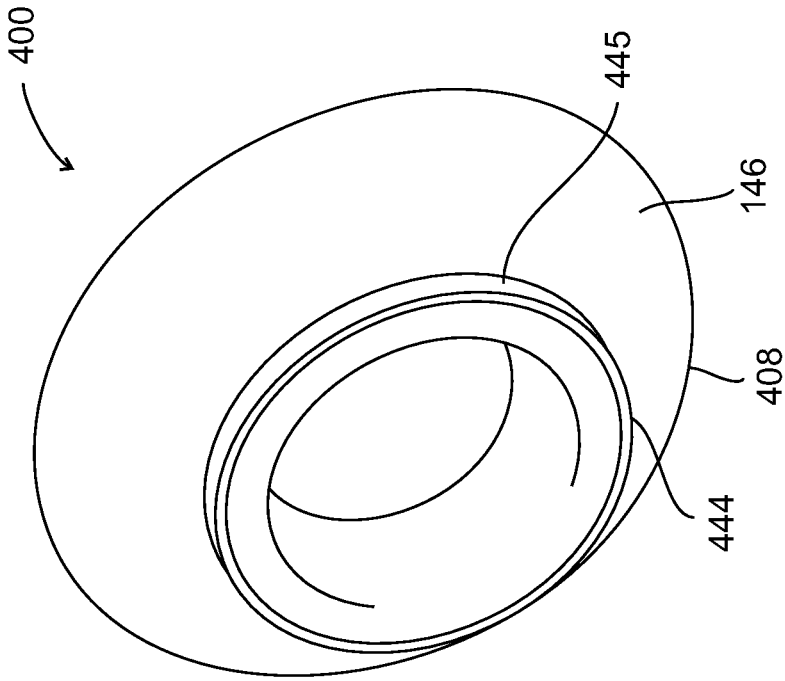
FIG. 7A schematically illustrates a perspective view of an adaptor having a flexible fixation ring for gas release in a ostomy appliance, in accordance with some exemplary embodiments of the invention.

Reference is now made to FIG. 7A which schematically illustrates a perspective view of an adaptor 408 having a flexible fixation ring 444 for gas release in an ostomy appliance 400, and to FIG. 7B which shows a front view of the adaptor with the flexible fixation ring in a gas release mode, according to some exemplary embodiments of the invention. In some embodiments, a gas release mechanism described in the aforementioned WO 2011/138727 by the applicant is used with flexible fixation ring 444. Flexible fixation ring 444 is configured for allowing a gas flow path 448 for gas release from within adaptor 408 when the fixation element is pressed, for example, as shown by the arrows marked "PRESS". In some embodiments, flexible fixation ring 444 is a separate component and attached to adaptor body 146. Alternatively, fixation ring 444 is an integral component of adaptor body 146.

Another Exemplary Ostomy Appliance with Gas Release

Figure 8:
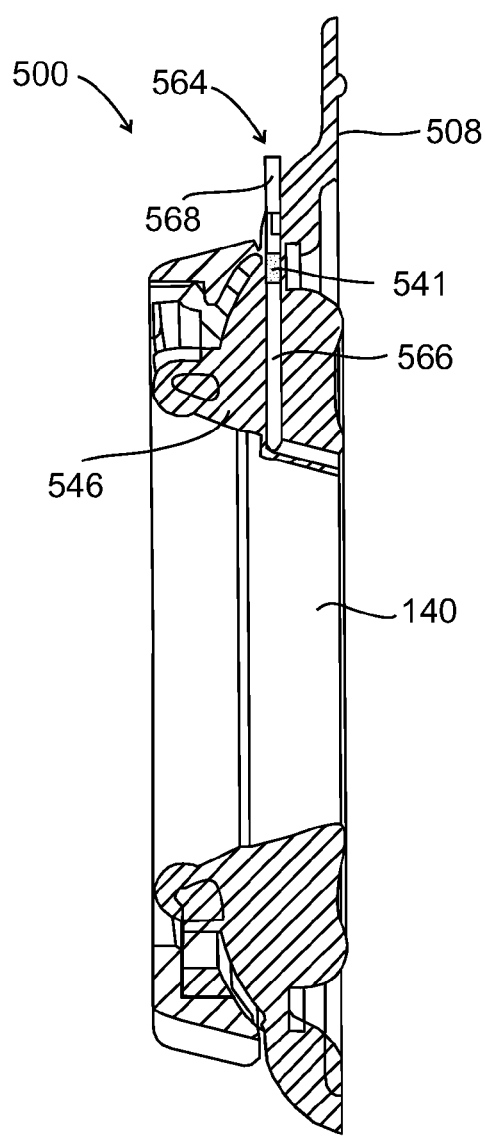
FIG. 8 schematically illustrates a sectional view of an adaptor having an external ventilation port for gas release in an ostomy appliance in accordance with some exemplary embodiments of the present invention.

Reference is now made to FIG. 8 which schematically illustrates a sectional view of an adaptor 508 in an ostomy appliance 500 having ventilation port 564 for gas release, according to some exemplary embodiments of the present invention.

In some exemplary embodiments, a ventilation lumen 566 extends from ventilation port 564 through adaptor body 546 to cavity 140. Ventilation lumen 566 is configured for conducting gases from cavity 140 to ventilation port 566 where they are expelled from adaptor 508. Optionally, ventilation lumen 566 extends along an inner wall of adaptor body 546 bordering cavity 140 and leads to stoma 104. Optionally or alternatively, ventilation lumen 566 includes a plurality of openings for reducing the possibility of lumen blockage due to accumulation of waste matter in the lumen's opening.

In some exemplary embodiments, ventilation lumen 566 includes a filter 541 for filtering gases flowing through the ventilation lumen in a direction of ventilation port 564. Additionally or alternatively, ventilation port 564 is fitted with a valve 568 for allowing a user to control gas release. In some embodiments, a gas release mechanism described in FIG. 7 in the WO 2011/138727 by the applicant, is used with valve 568 and filter 561.

Another Exemplary Ostomy Appliance with Gas Release

Figure 9:
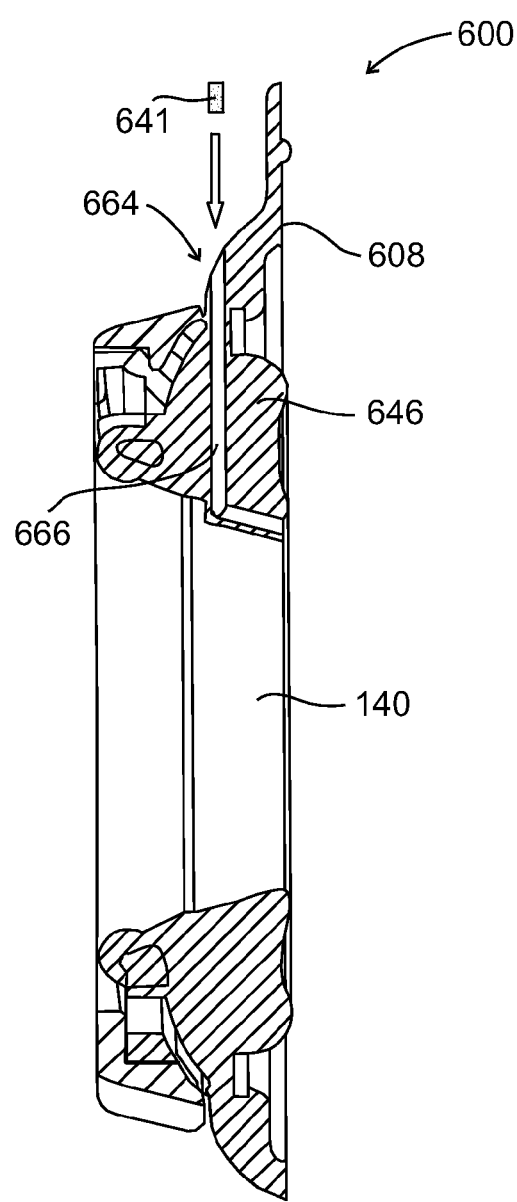
FIG. 9 schematically illustrates a sectional view of an adaptor having an external ventilation port for gas release in an ostomy appliance, in accordance with some exemplary embodiments of the present invention.

Reference is now made to FIG. 9 which schematically illustrates a sectional view of an adaptor 608 having an external ventilation port 664 for gas release in an ostomy appliance 600, according to some exemplary embodiments of the present invention. Adaptor 608 includes a ventilation lumen 666 optionally mechanically and functionally similar to ventilation lumen 566 in adaptor 508 shown in FIG. 8. Optionally, ventilation port 664 is configured for receiving a replaceable filter 641 for filtering gases flowing through ventilation lumen 666 in a direction towards ventilation port 664. In some embodiments, the gas release mechanism described in FIG. 9 in WO 2011/138727 by the applicant, is used with filter 641.

Exemplary Sealing Elements

Inflatable Sealing Element

Figure 10A:
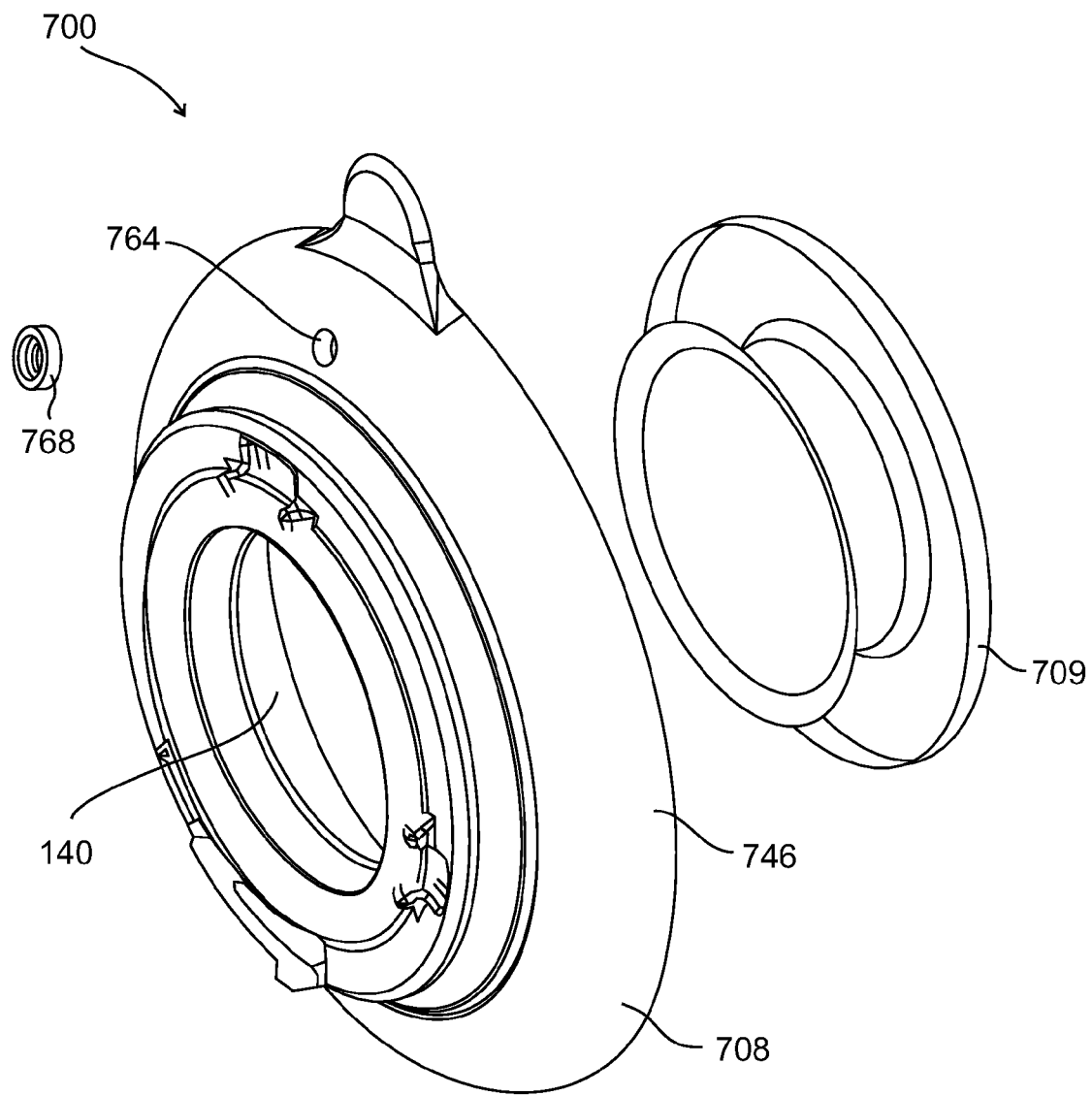
FIG. 10A schematically illustrates a perspective view of an adaptor and an inflatable sealing element in an ostomy appliance, in accordance with some exemplary embodiments of the present invention.
Figure 10D:
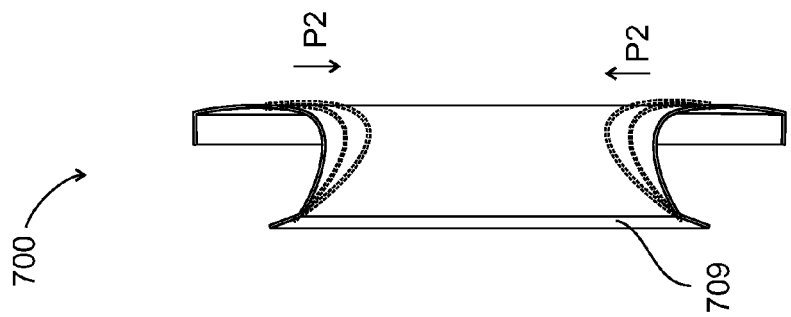
FIGS. 10C and 10D schematically show side views of inflatable sealing element applying pressure in different directions, in accordance with some exemplary embodiments of the invention.
Figure 10C:
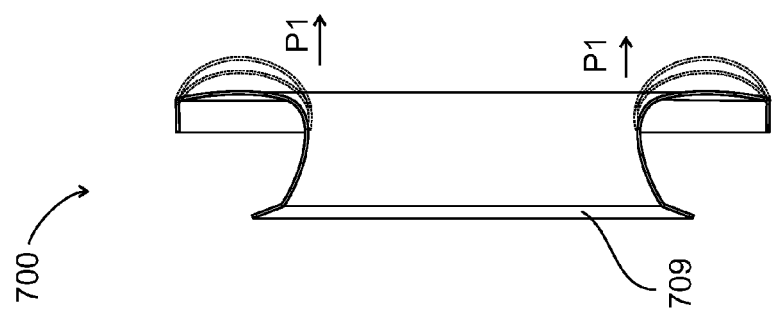
Figure 10B:
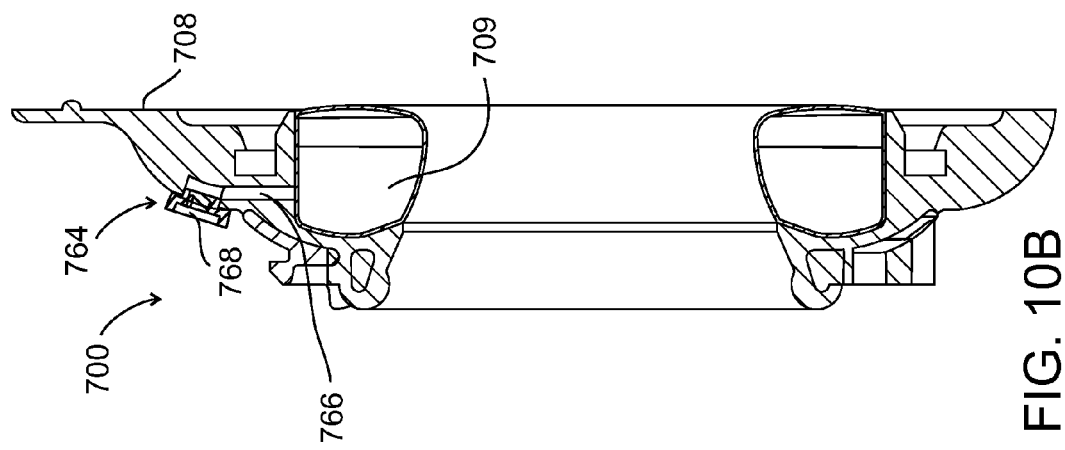
FIG. 10B schematically illustrates a sectional view of the adaptor with the inflatable sealing element inside a cavity, in accordance with some exemplary embodiments of the present invention.

Reference is now made to FIG. 10A which schematically illustrates an exploded perspective view of an adaptor 708 and an inflatable sealing element 709 in an ostomy appliance 700, and to FIG. 10B which schematically illustrates a sectional view of the adaptor with the inflatable sealing element inside cavity 140, according to some exemplary embodiments of the present invention. Optionally, inflatable sealing element 709 is a balloon, comprised of wall material capable of stretching under the pressure of inflation, such as a silicone elastomer. In some embodiments sealing element 709 is a secondary sealing-directed element with a potential role in primary sealing.

In some exemplary embodiments, balloon 709 may be configured for being inflated for applying pressure to stoma 104 (not shown in the figure) for increasing the sealing at wafer/stoma interface 105 (not shown in the figure). Additionally or alternatively, balloon 709 may be configured for applying pressure to wafer 102 (not shown in the figure) for increasing the sealing at wafer/stoma interface 105.

Increasing sealing at wafer/stoma interface 105 reduces possible leakage from adaptor 708 of waste content or of flushing liquid during flushing. Optionally, increased sealing at wafer/stoma interface provides a double sealing arrangement reducing and/or eliminating a pressure of waste content and/or flushing fluid at adaptor/wafer interface 103 (not shown in figure).

Optionally, a direction in which the pressure is applied by balloon 709 is predetermined during manufacture of the balloon and may involve adjusting balloon wall thickness, for example, by reducing thickness in portions of the wall, and/or by reinforcing portions of the wall. Additionally or alternatively, the direction of applied pressure may be predetermined by adjusting the material properties of the wall, such as the elasticity; for example by lamination of some portions with a less elastic reinforcing material. Materials which may be used to reinforce portions of the balloon wall may include fabric or polymeric mesh.

A potential advantage of controlling a direction of pressure application allows for enhancing ostomy appliance 700 sealing against wafer 102 and against stoma 104. An additional potential advantage of said direction controlling is that a single device can potentially accommodate stomas of various diameters by controlling the extent to which balloon 709 extends in a direction towards stoma 104 during inflation.

Reference is now also made to FIGS. 10C and 10D which schematically show side views of balloon 709 applying pressure in different directions, according to some exemplary embodiments of the invention. In FIG. 10C, balloon 709 is shown applying a pressure P1 in an axial direction pressing against wafer 102 increasing the sealing at wafer/stoma interface 105. In FIG. 10D, balloon 709 is shown applying a pressure P2 in a negative radial direction into cavity 140 pressing against stoma 104 increasing the sealing at wafer/stoma interface 105. Optionally, the pressure P1 and/or P2 may range from 5-40 mmHg, for example, 6 mmHg, 10 mmHg, 15 mmHg, 25 mmHg, 32 mmHg. In some embodiments, adaptor 708 with balloon 709 configured for pressing in the negative radial direction is usable with wafers 102 having wafer ports 118 and/or pouch attachment elements 132 (wafer, wafer port, and pouch attachment element, not shown in the figure) of varying sizes.

Adaptor 708 includes an inflation port 764 in adaptor body 746 and an inflation valve 768 adapted to be accommodated in the inflation port. An inflation lumen 766 extends from inflation port 764 through adaptor body 746 in a direction to cavity 140 and connects with balloon 709. Inflation and deflation of balloon 709 is through inflation valve 768 which regulates a direction of air flow through inflation lumen 766.

In some exemplary embodiments, balloon 709 may be an integral component of adaptor 708 and is formed (manufactured) together with the adaptor. Alternatively, balloon 709 is a separate component formed independently of adaptor 708 and assembled into cavity 140 at a later stage of production.

Exemplary Compressible Sealing Element

Figure 11:
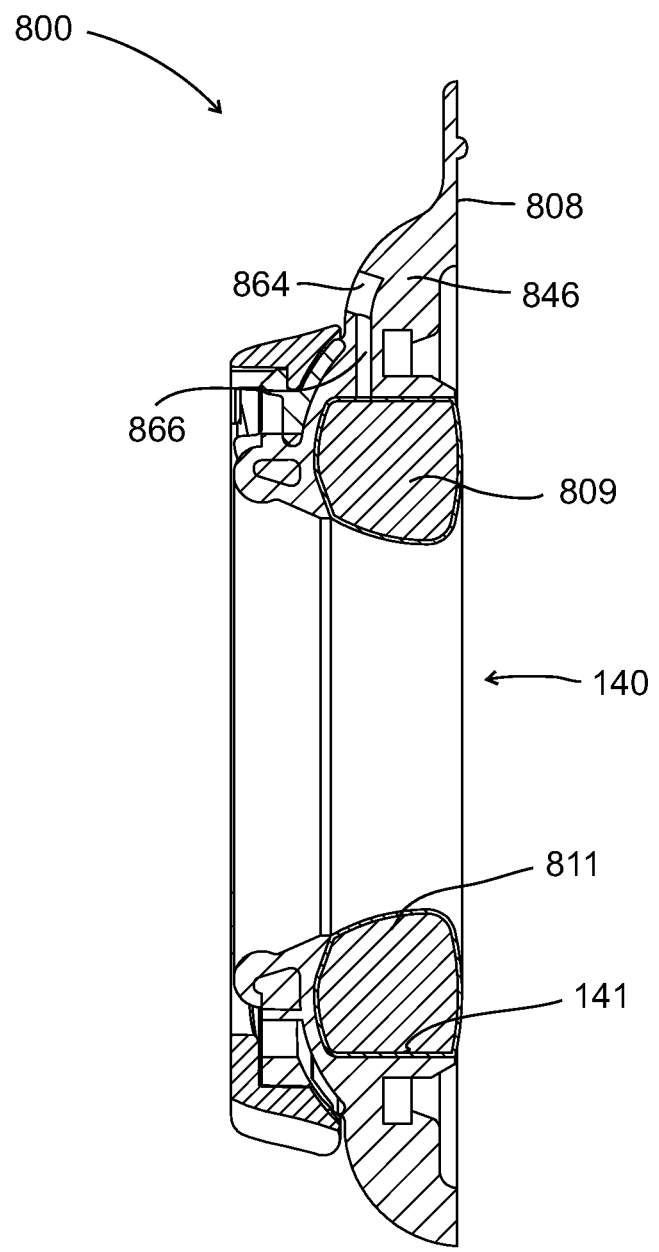
FIG. 11 schematically illustrates a sectional view of an adaptor with a compressible sealing element in an ostomy appliance, in accordance with some exemplary embodiments of the present invention.

Reference is now made to FIG. 11 which schematically illustrates a sectional view of an adaptor 808 with a compressible sealing element 809 in an ostomy appliance 800, according to some exemplary embodiments of the present invention.

In some exemplary embodiments, sealing element 809 is configured for pressing against a proximal surface of wafer 102 (not shown in the figure) when adaptor 808 is attached to wafer 102, preventing leakage of waste matter and/or flushing fluid through wafer/stoma interface 105 (not shown in the figure). Optionally, sealing element 809 acts as a redundant sealing mechanism to that at wafer/adaptor interface 103 (not shown in figure). Optionally, sealing element 809 is compressibly accommodated inside cavity 140 and is configured for pressing against a peripheral inner wall 141 in the cavity. A potential advantage of the compressive fit inside cavity 140 is preventing waste content from coming in contact with inner wall 141 for facilitating cleaning of adaptor 808. Optionally or alternatively, sealing element 809 is permanently attached to inner wall 141 for example by means of bonding or welding. Optionally, sealing element 809 is further configured for pressing against wafer 102 (not shown in the figure) for enhancing sealing around stoma 104 at wafer/stoma interface 105 (not shown in the figure). In some embodiments, sealing element 809 pressing against wafer 102 allows for sealing to be maintained at wafer/stoma interface 105 during natural flexing of the wafer.

In some exemplary embodiments, sealing element 809 includes a foam material, optionally permeable or semi-permeable to gases. Optionally, sealing element 809 is enclosed in a casing 811 which may also be permeable to gases. Optionally, sealing element 809 may include materials, for example charcoal, which may allow the sealing element to be used as a gas filter for filtering flatus passing from stoma 104, optionally through wafer port 118, into adaptor 808 (stoma and wafer port are not shown in the figure). In some embodiments, sealing element 809 absorbs odors from flatus, and/or includes a deodorizing agent for deodorizing the flatus. In some embodiments, adaptor 808 includes one or more external ventilation ports 864 and one or more ventilation lumens 866 extending from the ventilation port through adaptor body 846 towards cavity 140. Gas passing through sealing element 809 may flow through ventilation lumen 866 and out ventilation port 864. In some embodiments, the foam material in sealing element 809 is configured for absorbing liquid waste content. In some embodiments, an amount of liquid waste content absorbable by sealing element 809 is up to 100 ml, for example, 1 ml, 5 ml, 10 ml, 20 ml, 35 ml, 45 ml, 50 ml, 60 ml, 75 ml, 85 ml, 90 ml, 95 ml. Optionally, sealing element 809 may absorb amounts of liquid waste content in excess of 100 ml, for example, 120 ml, 150 ml, 180 ml, 200 ml, or more.

Exemplary Disposable Plug Sealing Element

Figure 12:
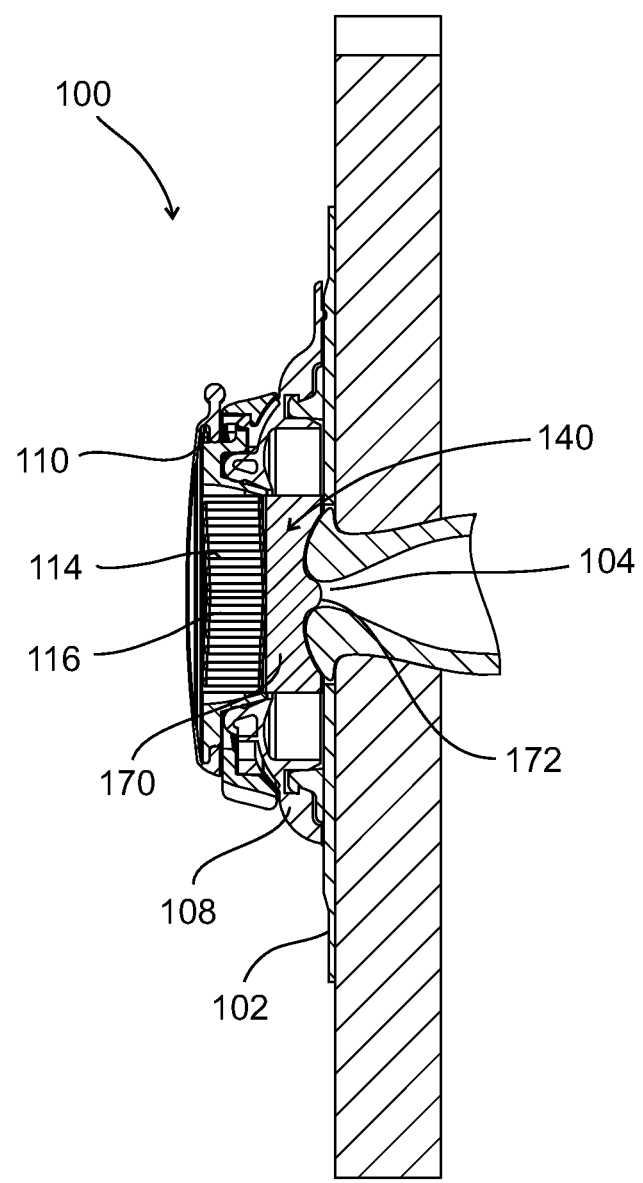
FIG. 12 schematically illustrates a sectional view of the ostomy appliance attached to the wafer covering the stoma and having the adaptor with a plug, in accordance with some embodiments of the present invention.

Reference is now made to FIG. 12 which schematically illustrates a sectional view of ostomy appliance 100 attached to wafer 102 covering stoma 104 and having adaptor 108 with a plug 170, according to some embodiments of the present invention. Plug 170 is sized and shaped to be fittingly accommodated within cavity 140, and is adapted to seal stoma 104. Optionally, plug 170 includes a distal end 172 shaped to conform to the shape of stoma 104. Optionally, plug 170 or distal end 172 is made of a pliable material adapted to self-conform to the shape of stoma 104. In some embodiments, plug 170 and/or distal end 172 is partially or wholly containable inside stoma 104.

In some exemplary embodiments, plug 170 may be a disposable plug which is disposed of together with pouch 114. For example, plug 170 may be pushed into pouch 114 by the pressure of the waste content flowing into the pouch. Additionally or alternatively, plug 170 may be attached to cap 110 so that removal of the cap or of lid 116 pulls the plug away from stoma 104 for allowing waste content flow into the pouch. Optionally, plug 170 is extracted from ostomy appliance 100 by removal of cap 110 or lid 116. In some embodiments, plugs 170 is attached to pouch 114 so that deployment of the pouch removes the plug from stoma 104 and extracts the plug from ostomy device 100. In some embodiments, plug 170 is attached to cap 110, lid 116, or pouch 114 by a string, cable, or other attachment element suitable for pulling on the plug.

In some exemplary embodiments, plug 170 may include a non-fluid absorbing solid elastomeric material such as, for example, silicone rubber. Alternatively, plug 170 may include a foam material which is non-fluid absorbing, or alternatively, fluid absorbing for absorbing liquid waste content flowing from stoma. 104. Optionally, plug 170 may be adapted to distend when liquid waste content is absorbed. In some embodiments, an amount of liquid waste content absorbable by plug 170 is up to 100 ml, for example, 1 ml, 5 ml, 10 ml, 20 ml, 35 ml, 45 ml, 50 ml, 60 ml, 75 ml, 85 ml, 90 ml, 95 ml. Optionally, plug 170 may absorb amounts of liquid waste content in excess of 100 ml, for example, 120 ml, 150 ml, 180 ml, 200 ml, or more.

Exemplary Absorbing Pad Sealing Element

Figure 13:
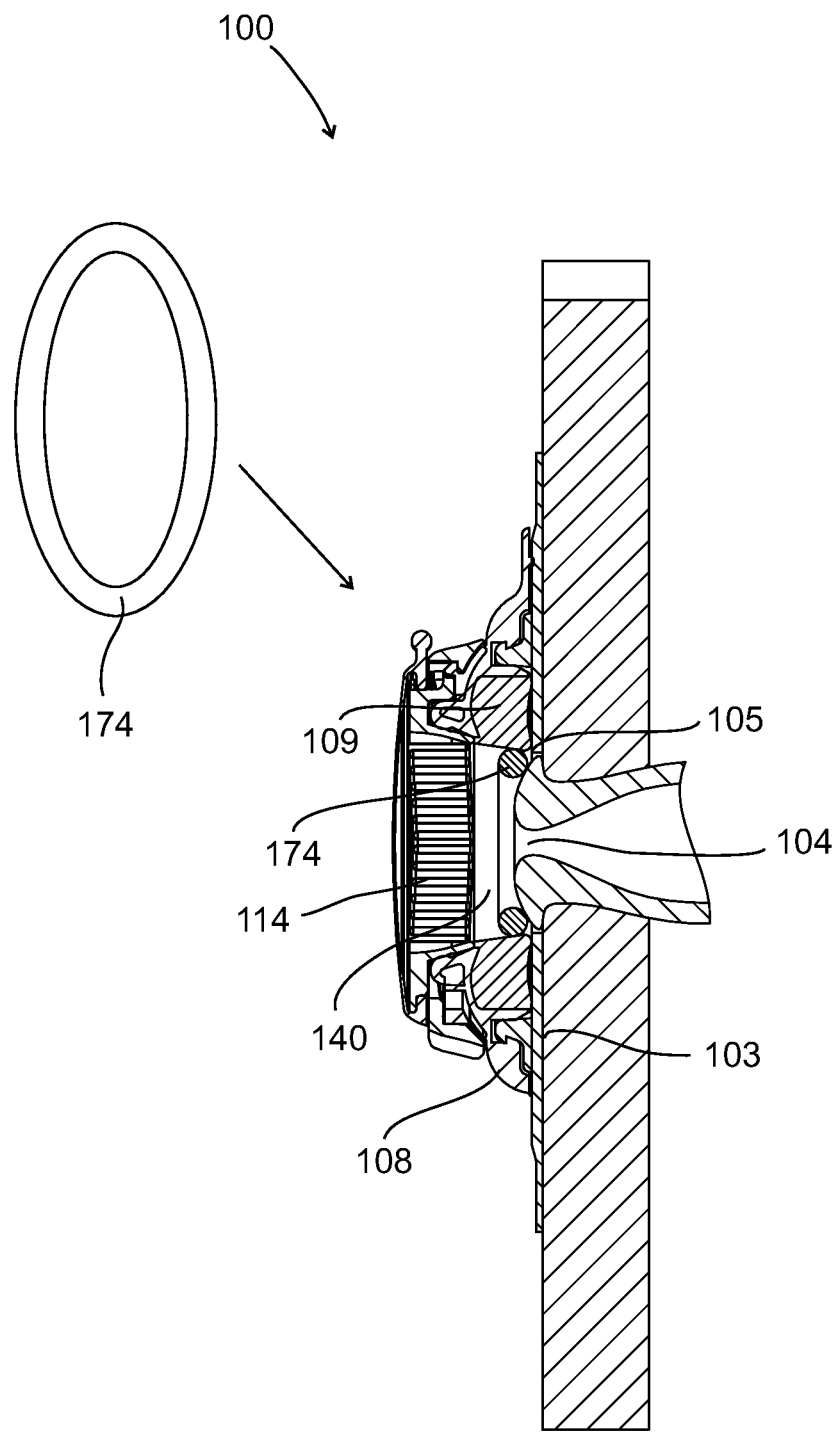
FIG. 13 schematically illustrates a sectional view of the ostomy appliance attached to the wafer covering the stoma and having the adaptor with an absorbing pad, in accordance with some embodiments of the present invention.

Reference is now made to FIG. 13 which schematically illustrates a sectional view of ostomy appliance 100 attached to wafer 102 covering stoma 104 and having adaptor 108 with an absorbing pad 174, according to some embodiments of the present invention. In some embodiments, pad 174 is a secondary sealing-directed element with a potential role in primary sealing. Absorbing pad 174 may be fitted inside cavity 140 between stoma 104 and pouch 114, and is adapted to absorb liquid waste content thereby reducing possible leakage of liquid waste content from adaptor 108. Optionally, absorbing pad 174 peripherally surrounds stoma 104. In some embodiments, an amount of liquid waste content absorbable by absorbing pad 174 is up to 100 ml, for example, 1 ml, 5 ml, 10 ml, 20 ml, 35 ml, 45 ml, 50 ml, 60 ml, 75 ml, 85 ml, 90 ml, 95 ml. Optionally, absorbing pad 174 may absorb amounts of liquid waste content in excess of 100 ml, for example, 120 ml, 150 ml, 180 ml, 200 ml, or more. Liquid waste content absorption by absorbing pad 174 potentially reduces the sealing requirements of sealing element 109 and/or at wafer/adaptor interface 103. Additionally or alternatively, absorbing pad 174 may serve to reduce an amount of liquid waste content required to be handled at wafer/stoma interface 105 and/or wafer/adaptor interface 103. In some embodiments, liquid waste absorption by absorbing pad 174 potentially facilitates cleaning of adaptor 108.

In some exemplary embodiments, absorbing pad 174 may be a disposable pad which is disposed of together with pouch 114. For example, absorbing pad 174 may be pushed into pouch 114 by the pressure of the waste content flowing into the pouch. Additionally or alternatively, absorbing pad 174 may be attached to cap 110 so that removal of the cap or of lid 116 pulls the pad away from stoma 104. Optionally, absorbing pad 174 is extracted from ostomy appliance 100 by removal of cap 110 or lid 116. In some embodiments, absorbing pad 174 is attached to pouch 114 so that deployment of the pouch removes the pad from stoma 104 and extracts the pad from ostomy device 100. In some embodiments, absorbing pad 174 is attached to cap 110, lid 116, or pouch 114 by a string, cable, or other attachment element suitable for pulling on the pad.

In some exemplary embodiments, absorbing pad 174 is made of a relatively highly liquid absorbing material such as, for example, cotton, cellulose, or other material from the group of materials known as super-absorbent polymers, or any combination thereof.

Figure 14:
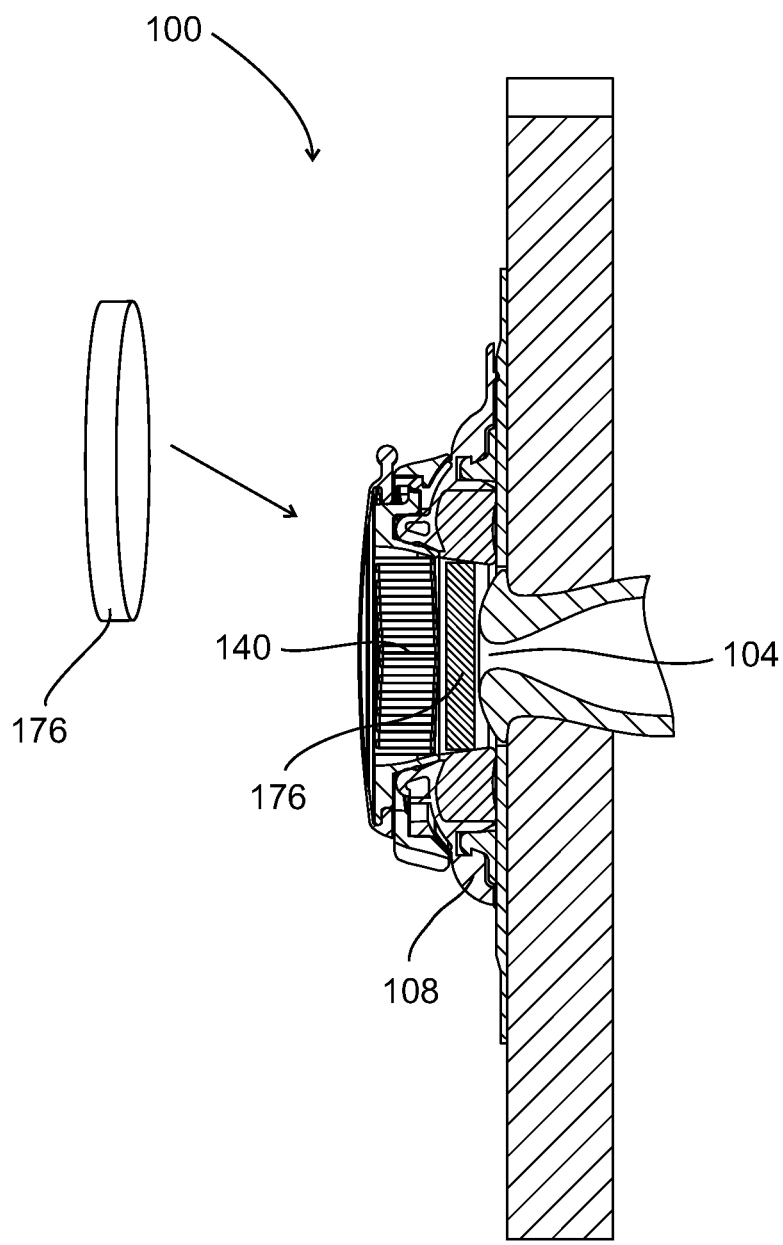
FIG. 14 schematically illustrates a sectional view of the ostomy appliance attached to the wafer covering the stoma and having the adaptor with a disc-shaped absorbing pad, in accordance with some embodiments of the present invention.
Figure 15:
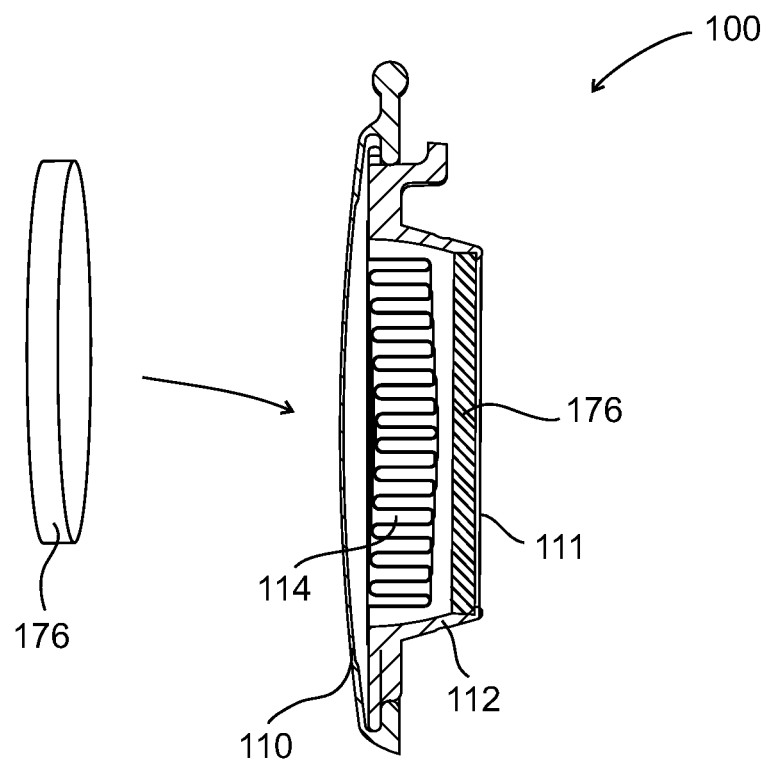
FIG. 15 schematically illustrates a sectional view of the cap with a disc-shaped absorbing pad, in accordance with some embodiments of the present invention.

In some exemplary embodiments, absorbing pad 174 is annular in shape, and has a round cross-section, for example as in an O-ring, for peripherally surrounding a circular stoma at wafer/stoma interface 105. Optionally, the cross-sectional shape of absorbing pad 174 conforms to the shape of sealing element 109 at wafer/stoma interface 105. Additionally or alternatively, absorbing pad conforms to the shape of cavity 140. In some embodiments, absorbing pad 170 has a non-circular cross-sectional shape conforming to the shape of sealing element 109 at wafer/stoma interface 105, to the shape of stoma 104, and/or to the shape of cavity 140. In some embodiments, adaptor 108 is fitted with a differently shaped absorbing pad, for example, a disc shape absorbing pad 176 as shown in FIG. 14. In some embodiments, the absorbing pad is accommodated in cap 110 inside housing 112, for example as shown by absorbing pad 176 in FIG. 15 positioned between pouch 114 and a distal opening 111 in the cap. Alternatively, other absorbing pads may be used inside housing 112, for example absorbing pad 174.

EXEMPLARY FLUSHING MECHANISM

Flushing-Type Sealing Element with Internal Fluid Distribution

Figure 16B:
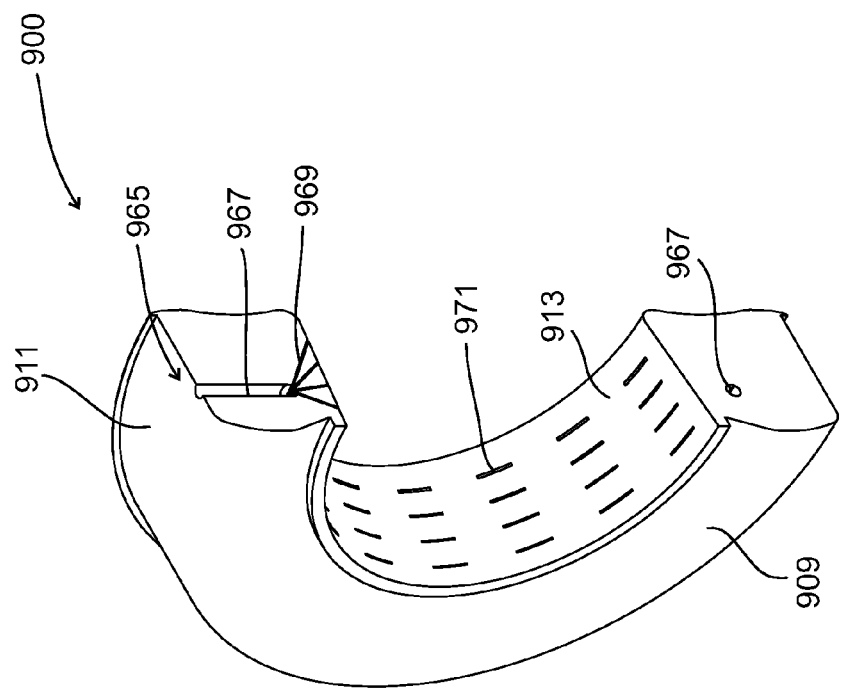
FIGS. 16A and 16B schematically illustrate perspective views of, respectively, an adaptor having a flushing-type sealing element in an ostomy appliance, and a cross-section of the sealing element, in accordance with some exemplary embodiments of the present invention.
Figure 16A:
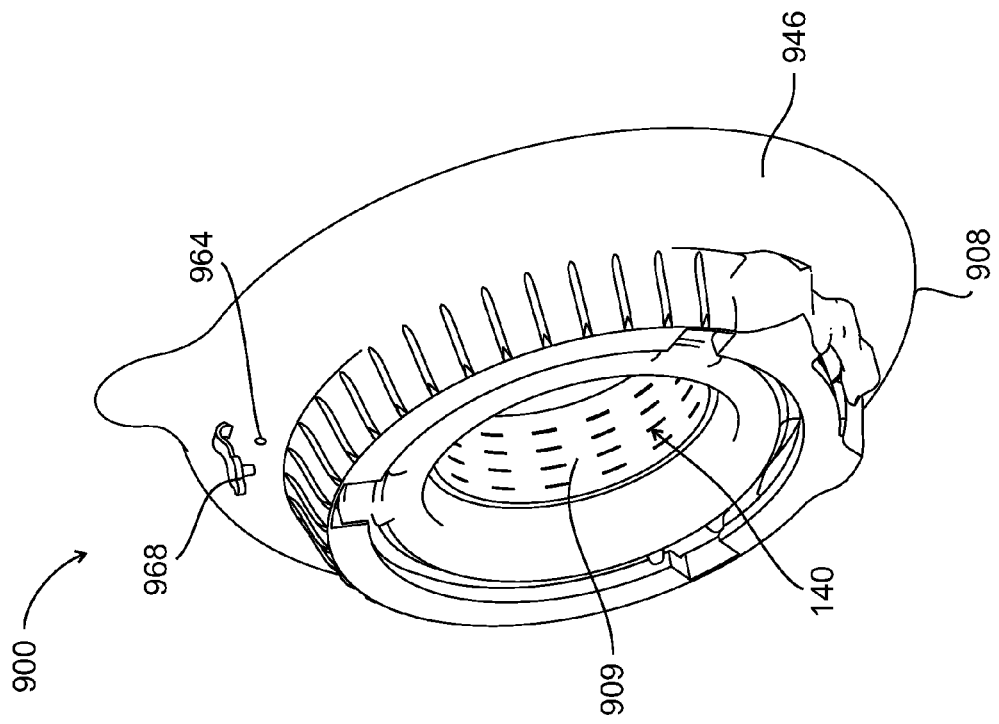
Figure 16C:
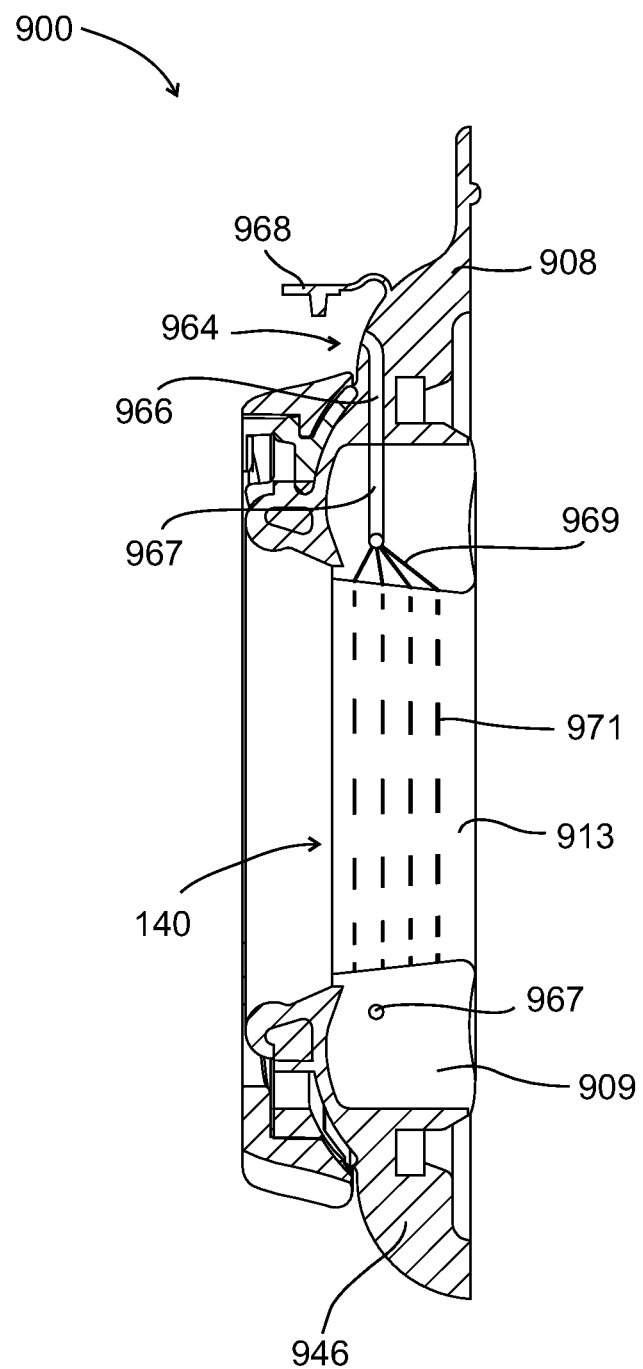
FIG. 16C schematically illustrates a sectional view of the adaptor with the sealing element, in accordance with some exemplary embodiments of the present invention.

Reference is now made to FIGS. 16A and 16B which schematically illustrate perspective views of an adaptor 908 having a flushing-type sealing element 909 in an ostomy appliance 900, and to FIG. 16C which schematically illustrates a sectional view of the adaptor with the sealing element, according to some exemplary embodiments of the present invention. In some embodiments sealing element 909 is a secondary sealing-directed element with a potential role in primary sealing. Adaptor 908 including sealing element 909 are configured for introducing a fluid into an internal portion of adaptor 908. Optionally, said fluid can be introduced into stoma 104 (not shown in the figures), for example for intestinal irrigation. In some embodiments, the flushing fluid is used for easing flow of waste matter through adaptor 908 into the pouch, for washing the stoma, for washing the peristomal skin, for washing the interior of the adaptor, for irrigating an interior of the intestine, or any combination thereof. In some embodiments, flushing is performed without sealing element 909 by introducing the flushing fluid into cavity 140 and therefrom to the stoma and other areas.

In some exemplary embodiments, adaptor body 946 includes a flushing port 964 through which the flushing fluid may be injected, or otherwise administered, into adaptor 908. A flushing lumen 966 extends from flushing port 964 through adaptor body 946 in a direction towards cavity 140, connecting to a feeder port 965 in an outer wall 911 of sealing element 909. A feeder lumen 967 inside sealing element 909 extends from feeder port 965 to one or more distribution lumens 969, for example four distribution lumens, peripherally extending along at least a portion of the sealing element. One or more flushing openings 971, for example, 64 openings, are spaced along an inner wall 913 of sealing element 909 and are fluidly connected to distribution lumens 969. Optionally, a number of distribution lumens 969 and/or a number of flushing openings 971 included in sealing element 909 varies with a particular flushing application. Optionally, a design including location, size, and/or shape of distribution lumens 969 and/or flushing openings 971 in sealing element 909 vary with the application. For example, a sealing element used only for irrigation of the stoma may be different than a sealing element also used for washing the interior of the adaptor and/or washing the stoma and/or the peristomal skin.

An exemplary method of performing flushing, according to some embodiments, includes the user introducing the flushing fluid through flushing port 964 into flushing lumen 966. Optionally, a volume of the flushing fluid may range from 20 ml-1000 ml, or more, for example, 50 ml, 80 ml, 150 ml, 250 ml, 350 ml, 500 ml, 700 ml, 850 ml, 950 ml, 1100 ml, 1200 ml, 1500 ml. Fluid flow through flushing lumen 966 enters through feeder port 965 into feeder lumen 967, and therefrom into distribution lumens 969. The flushing fluid flowing through distribution lumens 969 exits through flushing openings 971 and flows therefrom into cavity 140 and other areas to be flushed.

In some exemplary embodiments, sealing element 909 may include a slot peripherally extending along outer wall 911 and positioned such that, regardless how the sealing element is positioned inside cavity 140, the slot is always aligned with flushing lumen 966 so that the flushing fluid flowing through the flushing lumen enters into the slot. Extending from the slot may be one or more feeder lumens 967, for example 2, 4, 7, 10, or more feeder lumens which are fluidly connect with one or more distribution lumens 969 and into which the flushing fluid from the slot flows.

In some exemplary embodiments, distribution lumens 969 and flushing openings 971 are sized and positioned in sealing element 909 for obtaining fluid flow in a predetermined location and/or direction. In some embodiments, flushing openings 971 are made of a relatively small size for allowing fluid flow out the openings and substantially preventing fluid flow back into the openings. In this manner, flushing openings 971 act as one-way valves, or flutter valves, and prevent possible outflow of waste content through the flushing system. Optionally, fluid flow out of flushing openings 971 may be at a pressure of up to 300 mm/Hg, for example 100 mm/Hg, 150 mm/Hg, 200 mm/Hg, 250 mm/Hg. In some exemplary embodiments, flushing port 964 may be closed by a flushing plug 968. Flushing plug 968 may serve to prevent outflow of flushing fluid administered into adaptor 908. Optionally, flushing plug 968 prevents outflow of gases or waste matter from within adaptor 908 through the flushing system.

In some embodiments, a one-way valve (not shown) is included in flushing lumen 966.

Exemplary Flushing-Type Sealing Element with External Fluid Distribution

Reference is now made to FIG. 17A which schematically illustrates a perspective view of a flushing-type sealing element 909', and to FIG. 17B which schematically illustrates a sectional view of adaptor 908 with the sealing element inside cavity 140, according to some exemplary embodiments of the present invention.

In some exemplary embodiments, sealing element 909 includes a feeder channel 967' circumferentially extending along outer wall 911' and connecting to one or more inlet slots 969'. Inlet slots 969' extend from feeder channel 967' along a proximal side 915' of sealing element 909' in a direction towards an inner wall 913' and terminate at flushing openings 971' proximal to inner wall 913'. In some embodiments, flushing openings 971' include reduced-size slots which allow fluid flow in a direction into cavity 140 while preventing backflow up into inlet slots 969' (functionally similar to a flutter valve).

An exemplary method of performing flushing, according to some embodiments, includes the user introducing the flushing fluid through flushing port 964 into flushing lumen 966. Fluid flow through flushing lumen 966 enters into feeder slot 967' and therefrom into inlet slot 969'. The flushing fluid flowing through inlet slots 969' exit through flushing openings 971' and flow therefrom into cavity 140 and other areas to be flushed.

In some exemplary embodiments, openings 971' are located on inner wall 913'. Alternatively, gaps 972' are left between openings 971' and inner wall 913', such that inlet slots 969' are normally not in fluid communication with cavity 140. In the later configuration, backflow of gases or waste matter from cavity 140 into slots 969' is eliminated while inflow of flushing fluid from slots 969' into cavity 140 is possible, through a check-valve mechanism known in the art as a "flutter valve" or a "duckbill valve" When a pressurized fluid is present in inlet slots 969', its pressure acts on gaps 972' and forces them to shift in the distal direction thus enabling the fluid to flow into cavity 140. When a pressurized fluid is present in cavity 140, its pressure acts on inner wall 913'. As a result gaps 972' are tightened onto the adaptor' s body, thus flow of fluid from cavity 140 into inlet slots 969' is eliminated.

Exemplary Flushing-type Sealing Element with Flushing Tube

Figure 18:
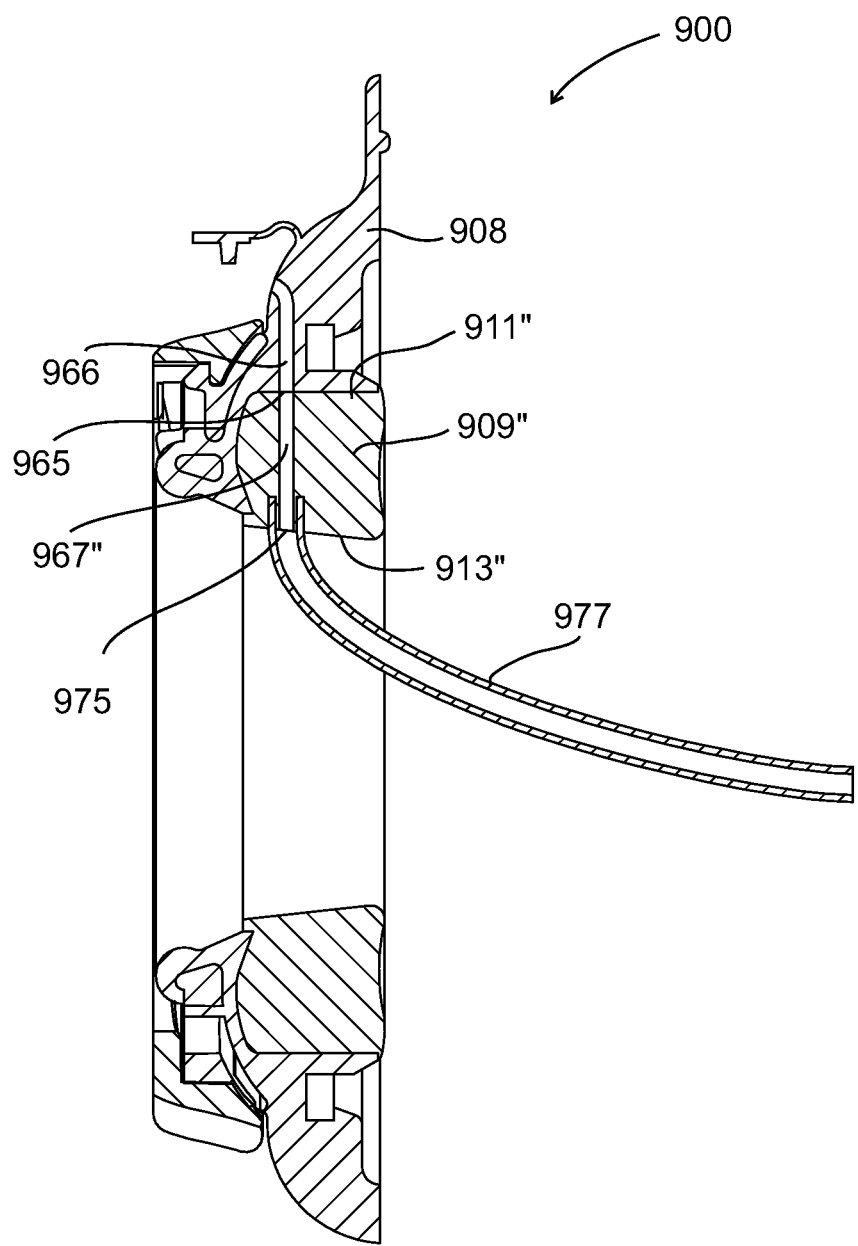
FIG. 18 schematically illustrates a section of an adaptor including a flushing-type sealing element in an ostomy appliance, in accordance with some exemplary embodiments of the present invention.

Reference is now made to FIG. 18 which schematically illustrates a section of adaptor 908 including a flushing-type sealing element 909" in ostomy appliance 900, according to some exemplary embodiments of the present invention. Sealing element 909" includes a feeder lumen 967" extending from an outer wall 911" to an inner wall 913" in the sealing element, having a feeder port 965 on the outer wall, and an outlet port 975 on the inner wall. Outlet port 975 is configured for attaching a flushing tube 977 which may be inserted into stoma 104 (not shown in the figure) for intestinal flushing or irrigation.

Exemplary Integrated-Component Ostomy Appliances

Exemplary Integrated-component Cap/Adaptor

Figure 19:
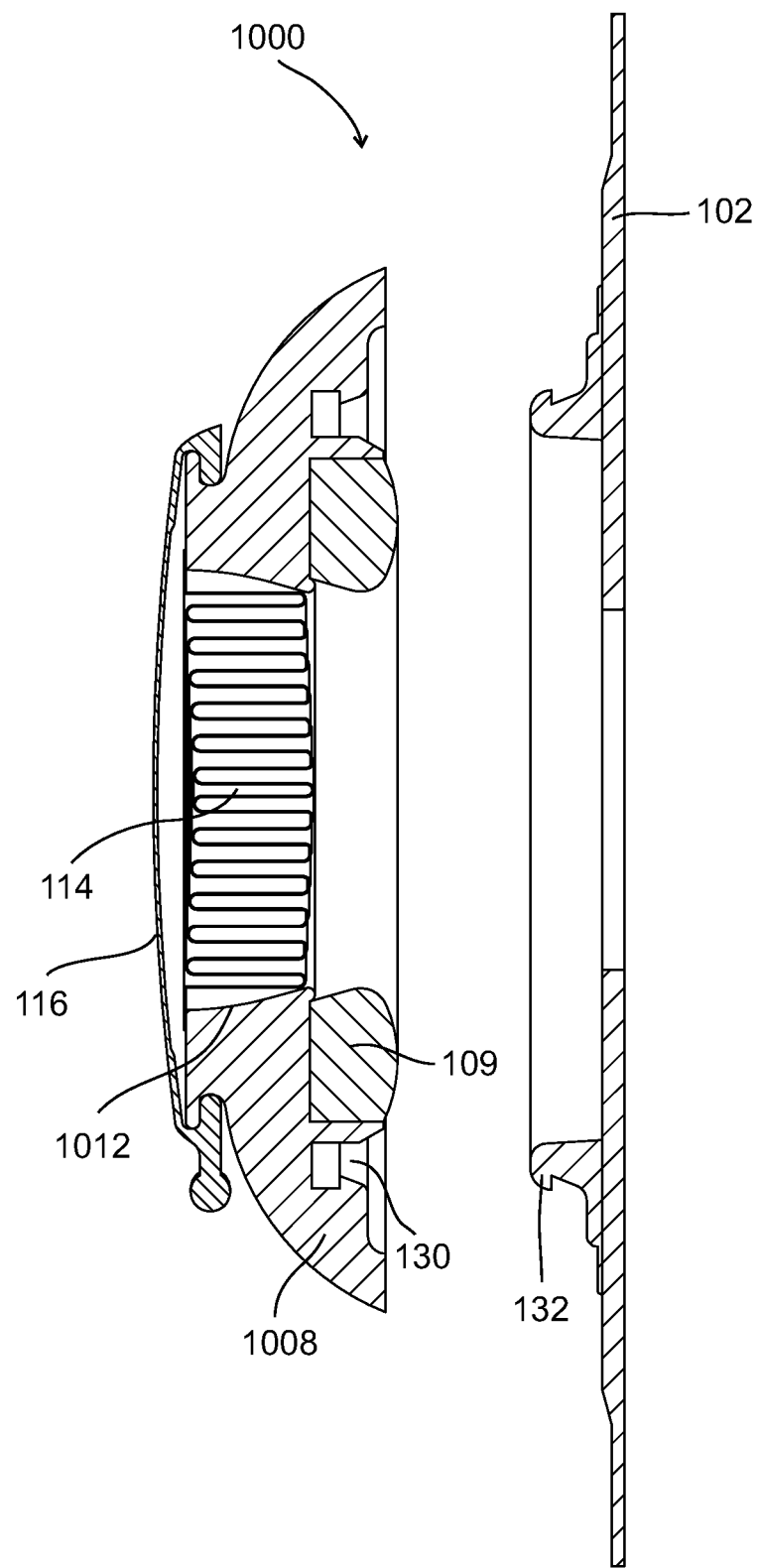
FIG. 19 schematically illustrates a sectional view of an integral ostomy appliance for attaching to a wafer, in accordance with some exemplary embodiments of the present invention.

Reference is now made to FIG. 19 which schematically illustrates a sectional view of an integral ostomy appliance 1000 for attaching to wafer 102, according to some exemplary embodiments of the present invention. FIG. 19 illustrates an embodiment where a cap and an adaptor are integrally formed.

In some exemplary embodiments, integral ostomy appliance 1000 includes an adaptor 1008 having a housing 1012 accommodating collapsed pouch 114, and removable lid 116. In some embodiments, lid 116 removal and pouch 114 deployment use mechanisms earlier described for ostomy appliance 100. Optionally, integral ostomy appliance 1000 includes sealing element 109. Integral ostomy appliance 1000 includes attachment mechanism 130 which mates with pouch attachment element 132 for attaching the ostomy appliance to wafer 102. In some embodiments, integral ostomy appliance 1000 includes any one feature, or combination of features, previously disclosed herein in some exemplary embodiments of the ostomy appliance. In some embodiments, integral ostomy appliance 1000 is disposed of following deployment of pouch 114. Alternatively, housing 1012 including deployed pouch 114 is replaced by a new housing 1012 with a collapsed pouch 114.

Exemplary Integral-Component Adaptor/Wafer

Figure 20:
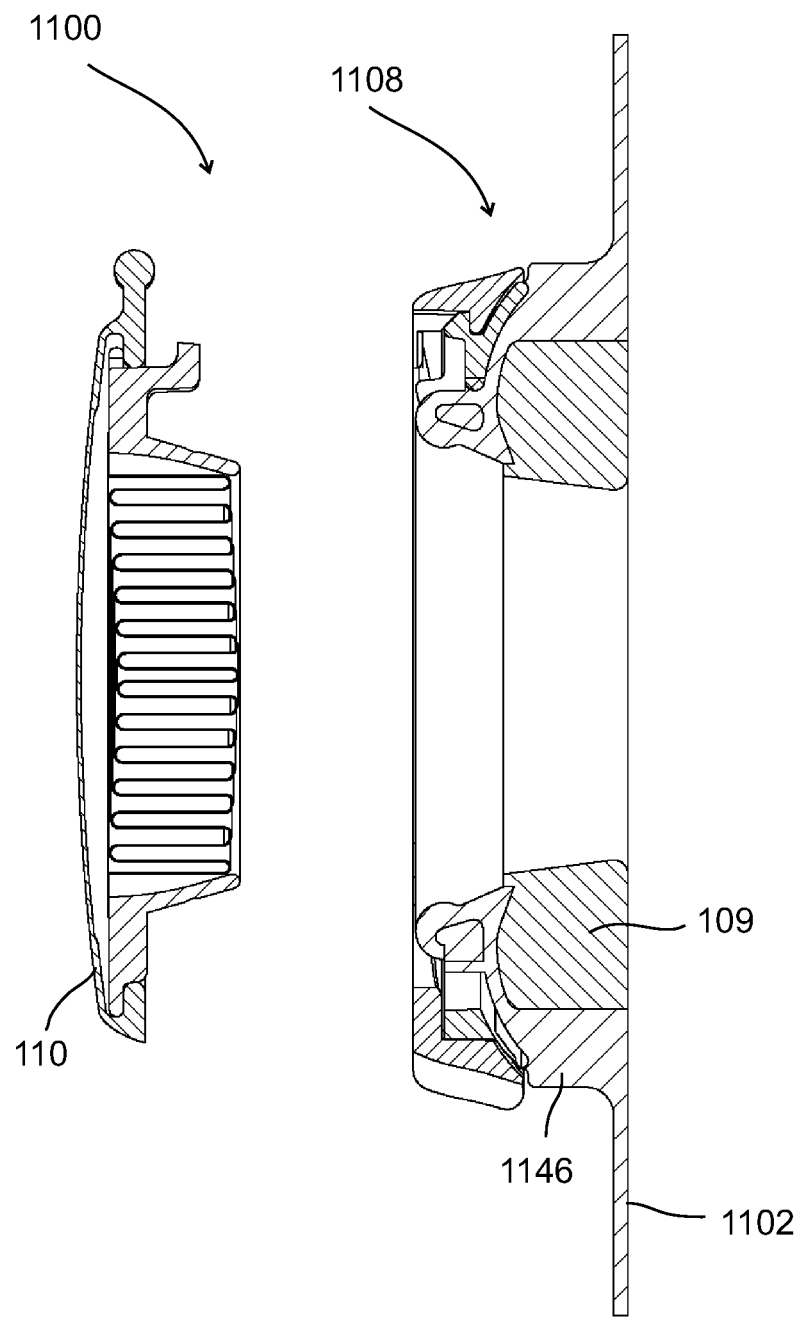
FIG. 20 schematically illustrates a sectional view of an ostomy appliance including an integral adaptor/wafer, in accordance with some exemplary embodiments of the present invention.

Reference is now made to FIG. 20 which schematically illustrates a sectional view of an ostomy appliance 1100 including an integral adaptor/wafer 1108, according to some exemplary embodiments of the present invention. FIG. 20 illustrates an embodiment where a wafer and an adaptor are integrally formed.

Adaptor/wafer 1108 includes an adaptor body 1146 and wafer 1102 integrally manufactured as a single component. Alternatively, adaptor body 1146 and wafer 1102 are separately manufactured as two components and are joined together through methods known in the art which may include, for example, bonding or welding.

In some exemplary embodiments, adaptor/wafer 1108 is adapted to accommodate cap 110. Alternatively, adaptor/wafer 1108 is adapted to accommodate cap 210. In some embodiments, adaptor/wafer 1108 includes sealing element 109. In some embodiments, sealing element 109 is separately attachable to the adaptor/wafer. Alternatively, sealing element 109 may be formed integrally with adaptor/wafer 1108. In some embodiments, ostomy appliance 1100 includes any one feature, or combination of features, previously disclosed herein in some exemplary embodiments of the ostomy appliance. In some embodiments, adaptor/wafer 1108 is disposed of following a predetermined period of time, or a predetermined number of pouch deployments, or as required by the user.

Exemplary Integral-Component Cap/Wafer/Adaptor

Figure 21:
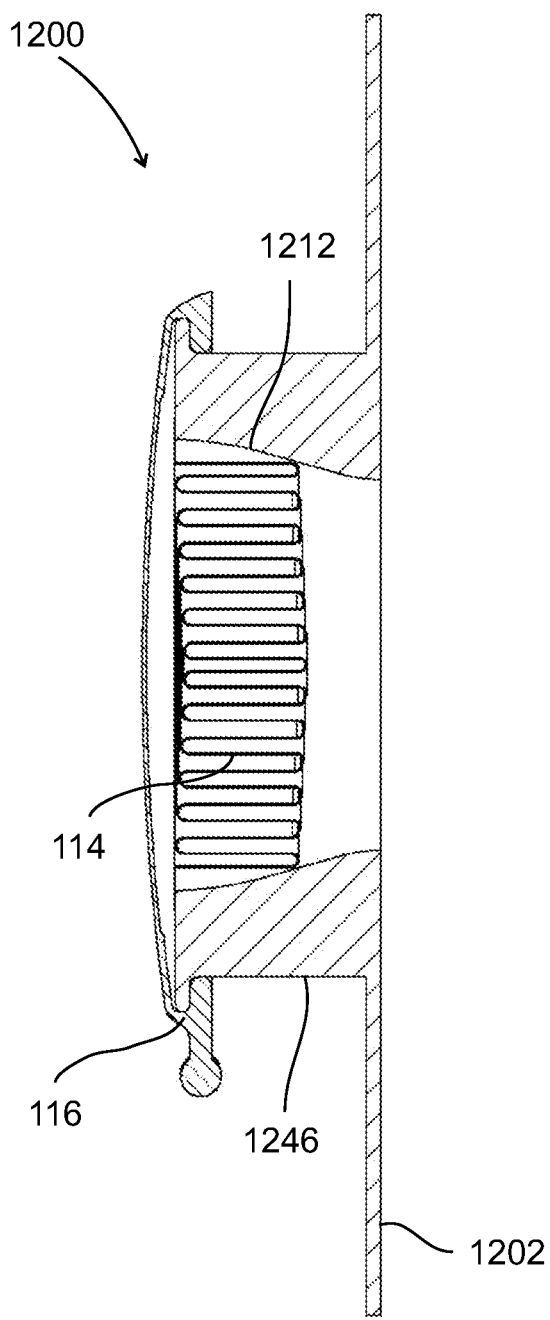
FIG. 21 schematically illustrates a sectional view of an integral ostomy appliance including a collapsed pouch, a wafer, and a lid, in accordance with some exemplary embodiments of the present invention.

Reference is now made to FIG. 21 which schematically illustrates a sectional view of an integral ostomy appliance 1200 including a collapsed pouch 114, a wafer 1202, and a lid 116, according to some exemplary embodiments of the present invention. Ostomy appliance 1200 includes an adaptor body 1246 having a housing 1212 and a wafer 1202 integrally manufactured as a single component. Alternatively, adaptor body 1246 including housing 1212 and wafer 1202 are separately manufactured as two or more components and are joined together, for example, through methods known in the art which may include, for example, bonding (chemical or adhesive) or welding. Lid 116 and collapsed pouch 114 are separately included in ostomy appliance 1200. In some embodiments, ostomy appliance 1200 includes any one feature, or combination of features, previously disclosed herein in some exemplary embodiments of the ostomy appliance.

In some embodiments, ostomy appliance 1200 is disposed of following a predetermined period of time, or a predetermined number of pouch deployments, or as required by the user. Optionally, housing 1212 including deployed pouch 114 is replaced by a new housing 1212 with a collapsed pouch 114. A potential advantage in replacing only housing 1212 with pouch 114 includes minimum handling by the user of the ostomy appliance and reduced storage space required in handbags and briefcases as only the housing is required.

Exemplary Integrated Lid/Adaptor

Reference is now made to FIG. 22A which schematically illustrates a perspective view of adaptor 208 shown in FIGS. 5A and 5B including an integrated lid 210', and to FIG. 22B which schematically illustrates a sectional view of the adaptor and the integrated lid, according to some exemplary embodiments of the present invention. Integrated lid 210' is fastened to adaptor 208, for example by means of a hinge, which may be a flexible tab or a hinged pin arrangement or a cable or other suitable attachment means, and is adapted to cover proximal opening 122.

In some embodiments, lid 210' serves as a pressure sensing cap for indicating to the user a need to evacuate. Optionally, lid 210' is adapted for use with some embodiments of cap 210 not configured with a pressure warning mechanism. In this configuration, cap 210 is inserted into the proximal opening and attached to adaptor 208, and lid 210' is closed over cap 210 and secured against adaptor body 244.

In some exemplary embodiments, integrated lid 210' may be used for preventing undesired deployment of collapsed bag 114. In some embodiments, integral lid 210' seals proximal opening 122 for preventing waste content from flowing or leaking out the proximal opening when closed over the proximal opening.

In some exemplary embodiments, adaptor 208 includes a fastening mechanism including a first mating element 264 on adaptor body 244 and a second mating element 266 on lid 210' for securing the cap against the adaptor body. Optionally, first mating element 264 and/or second mating element 266 are pressure activated by the user for securing lid 210' against adaptor body 244 and/or for releasing the cap from the body.

Exemplary Integral-Component Cap/Wafer Assembly

Figure 22C:
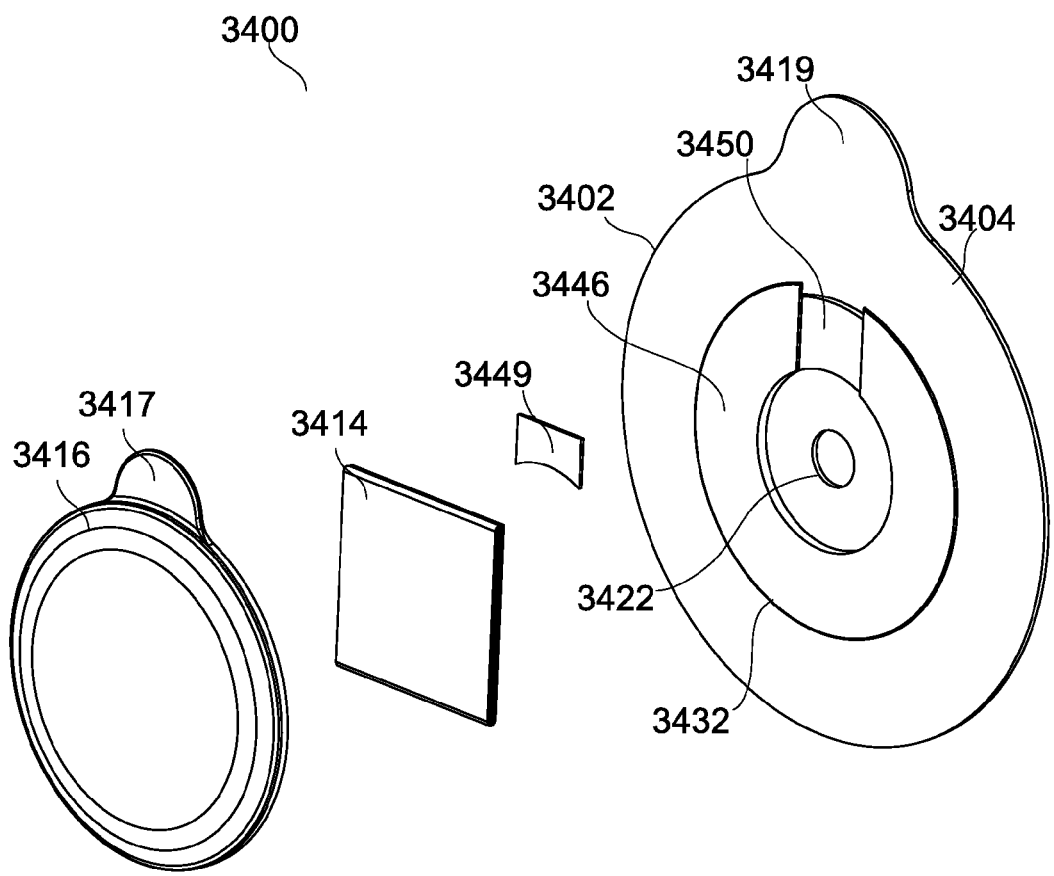
FIG. 22C schematically illustrates an exploded perspective view of an integral ostomy appliance including a collapsed pouch, a wafer, a filter, and a lid, in accordance with exemplary embodiments of the present invention.
Figure 22D:
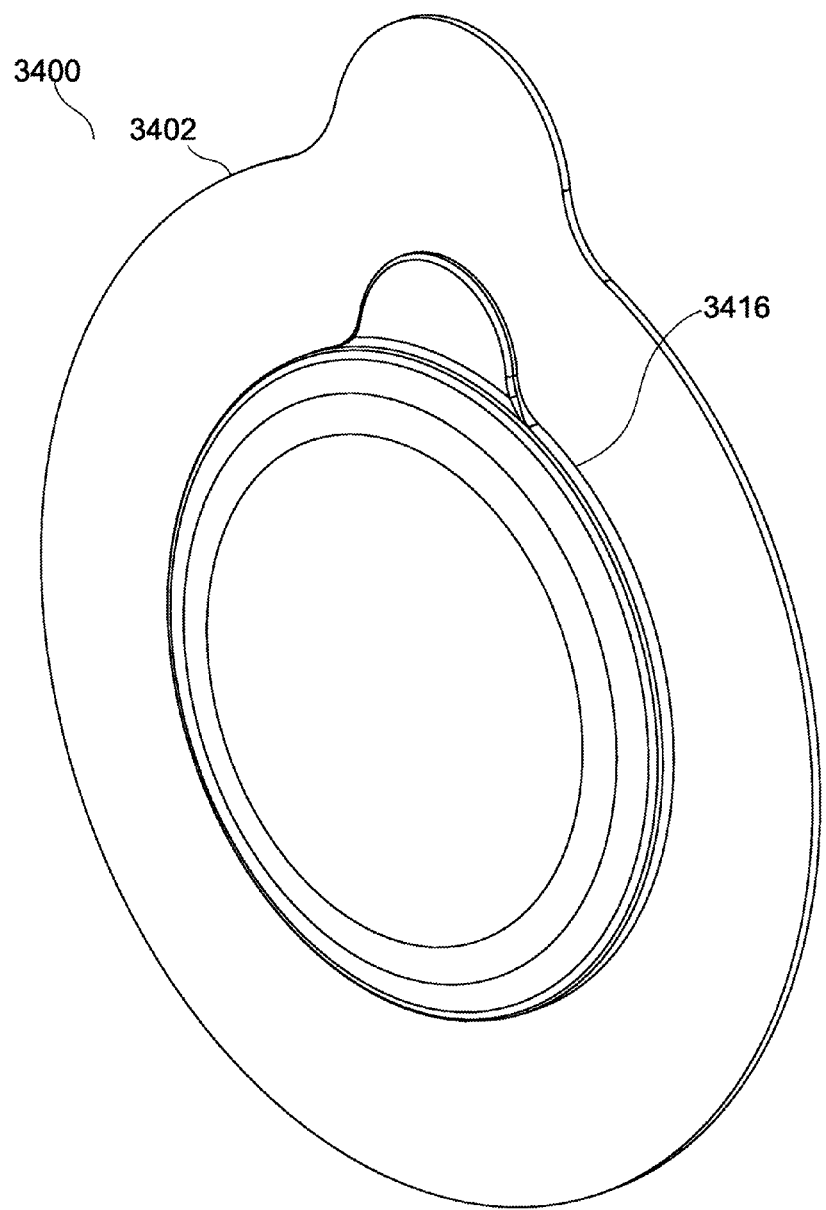
FIG. 22D schematically illustrates a perspective view of the assembled ostomy appliance of FIG. 22C, in accordance with exemplary embodiments of the present invention.

Reference is now made to FIGS. 22C and 22D which schematically illustrate perspective views of, respectively, an exploded and an assembled integral ostomy stack 3400 including a wafer 3402, an adaptor 3446, a collapsed pouch 3414, and a lid 3416, according to some exemplary embodiments of the present invention. The exemplary ostomy stack 3400 encompasses the functions of wafer, adaptor and cap in a single integrated component, and illustrates how such a stack may include a lidded, flat-folded pouch and an aperture-held filter to add waste release control functionality while maintaining a minimal stack height.

In some embodiments the ostomy component stack 3400 is especially designed for brief and/or active use. By making the stack as low as possible, a fuller advantage can be taken of flexible materials, providing a more conforming ostomy appliance. As long as a short period of wearing is intended, even some pressing of the stoma may be tolerated, in exchange for a lowered profile. In embodiments where the wearing period is brief, the pouch is provided primarily as a backup in case deployment becomes suddenly necessary. In such embodiments, the adhesive may be weaker, since it does not need to support the full weight of a filled waste collection pouch.

The ostomy wafer 3402 is integrally attached to ostomy adaptor 3446. Ostomy adaptor 3446 includes an attachment element 3432 which is optionally a flange.

Optionally, the diameter of ostomy wafer port 3422 may be chosen to suit the diameter of the stoma. Optionally, the portion of the pad 3404 of the ostomy wafer peripherally enclosed within the lumen of the adaptor 3446 may be constructed so that a suitably-sized wafer port may be cut from it before use.

A waste-receiving aperture of the collapsed pouch 3414 is attached, for example by chemical bonding or welding, so that it is in fluid communication with the lumen of adaptor 3446. In some embodiments, the pouch 3414 is folded into a flattened package which is contained by lid 3416 when it is attached to attachment element 3432.

In some embodiments, a pull-tab 3417 is provided on lid 3416, which protrudes from the lid. Optionally, the pull-tab protrudes laterally. Optionally, the pull-tab is large enough to be comfortably gripped with the fingers. Optionally, the pull-tab is of a material sufficiently flexible that a gripping appendage, for example a finger, can be inserted behind it. The pull-tab 3416 may be advantageous in removing lid 3417, which allows the expansion of waste pouch 3414, due, for example, to filling by waste.

In some embodiments, a pull-tab 3419 is provided on ostomy wafer 3402, which protrudes from the wafer, and is optionally constructed as a protrusion of pad 3404. Optionally, the pull-tab is not adhered to the underlying skin. Optionally, the pull-tab protrudes laterally. Optionally, the pull-tab is large enough to be comfortably gripped with the fingers. Optionally, the pull-tab is of a material sufficiently flexible that a gripping appendage can be inserted behind it. The pull-tab 3419 is advantageously used to remove ostomy wafer 3402, in order, for example, to exchange an old wafer with a replacement.

In some embodiments, a filter 3449 is provided, disposed within the ostomy appliance so as to permit gasses to escape through it from within the ostomy appliance. Optionally, adaptor 3446 is provided with an aperture 3450 which contains the filter 3449.

Optionally, ostomy wafer 3402, ostomy adaptor 3446 and lid 3416 are formed from a flexible and/or elastic material, for example silicone rubber or TPE, or a semi-rigid material such as, for example, polyethylene. Forming of said components from a flexible and/or elastic or semi-rigid material may provide an advantage by enabling the ostomy stack to conform to body movements and/or skin folds while occluding effluents emanating from the stoma.

Exemplary Methods of Using an Ostomy Appliance

Exemplary Method of Covering a Stoma Using Ostomy Appliance

Figure 23:
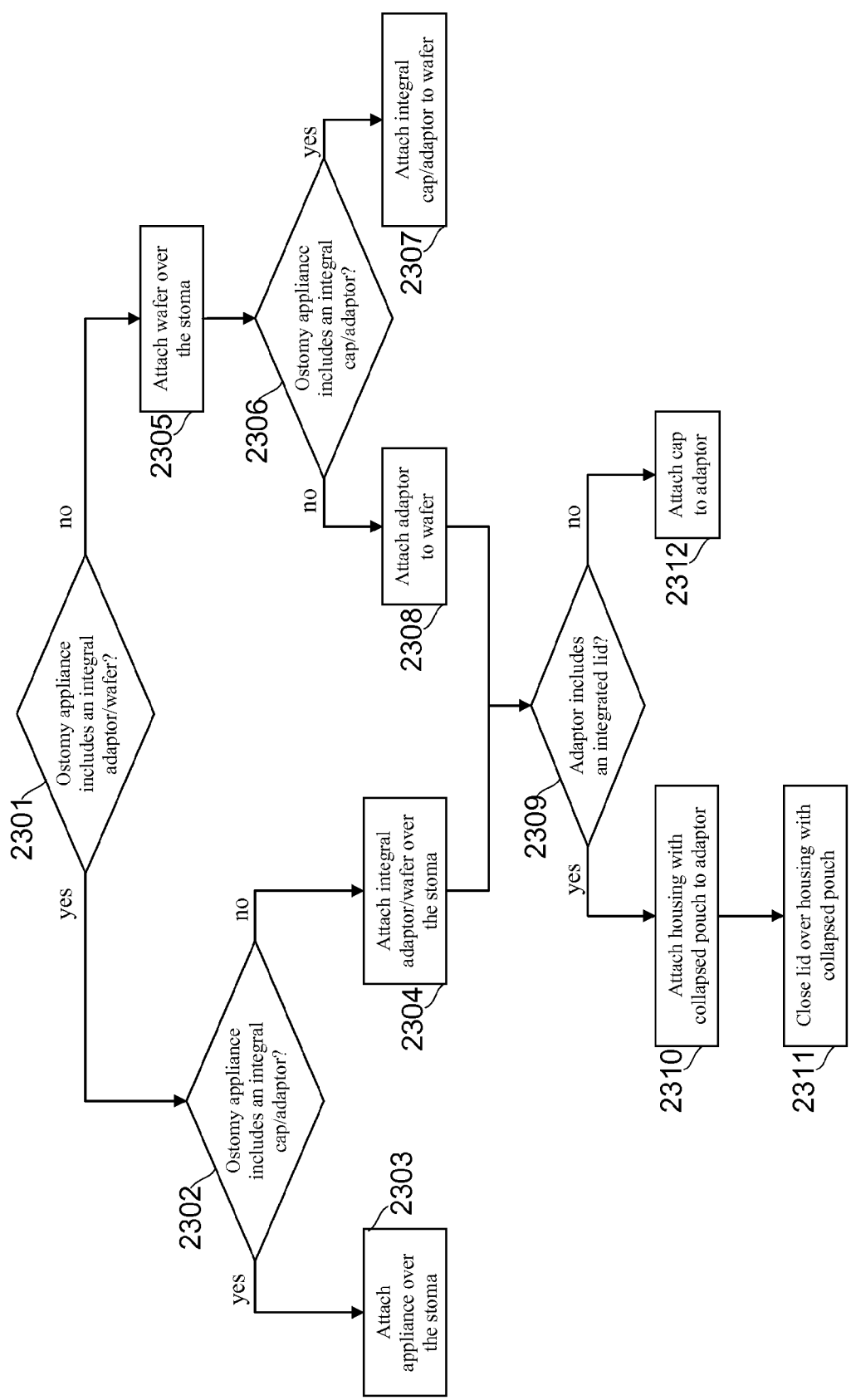
FIG. 23 is a flow chart of a method of covering a stoma with an ostomy appliance, in accordance with an exemplary embodiment of the present invention.

Reference is now made to FIG. 23 which is a flow chart of a method of covering a stoma with an ostomy appliance, according to an exemplary embodiment of the present invention. In describing the method drawing references are made to the various combinations of separate and integrated ostomy components and appliances described herein.

At 2301, the user determines whether the ostomy appliance to be used includes an integral adaptor/wafer.

If so, the user further determines at 2302 whether or not the ostomy appliance includes an integral cap/adaptor, and if so attaches the integrated appliance (corresponding, for example, to 3400) over the stoma 2303, finishing the task. If not, the user proceeds with attaching the integral adaptor/wafer 1102, 1108 over the stoma 2304, and continues with 2309 as described below.

From a negative determination at 2301, the user proceeds to attach the wafer (for example, 102) over stoma 2305. The user then determines if the ostomy appliance includes an integrated cap/adaptor 2306. If so, the user attaches an integral cap/adaptor 1008 to the wafer 2307, and the task is finished. If not, the user attaches an adaptor 108 to the wafer 2308, and continues with 2309.

At 2309, the user determines if the adaptor includes an integrated lid 116. If it does, the user attaches a housing 112 with a collapsed pouch 114 to the adaptor 2310, and closes the lid 116 over the housing 2311. If not, the user attaches a cap 110 to the adaptor 2312. In either case, the task is finished.

Method of Using the Ostomy Appliance

Figure 24:
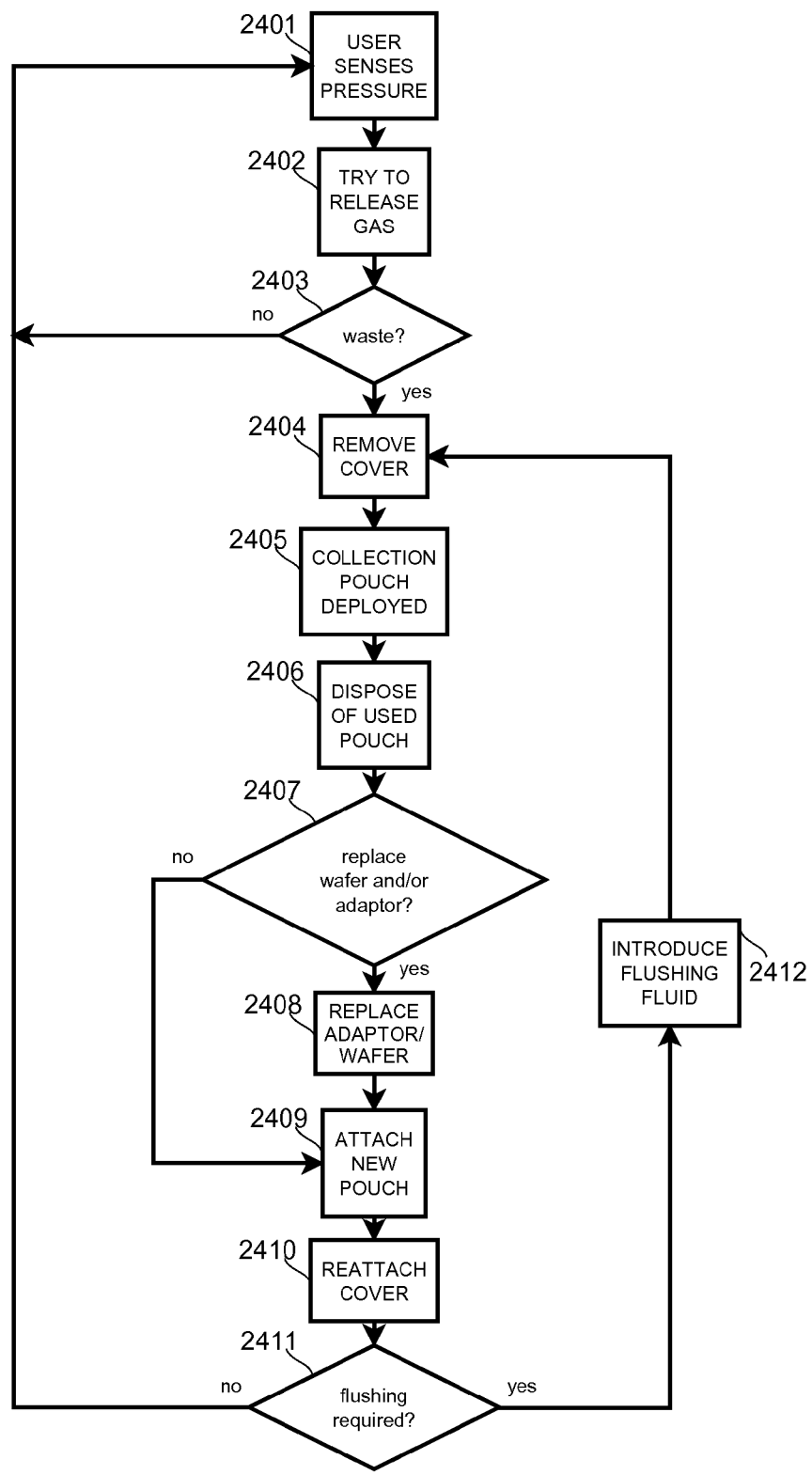
FIG. 24 is a flow chart of a method of using a smart cap with an ostomy appliance, in accordance with an embodiment of the present invention.

Reference is now made to FIG. 24 which is a flow chart of a method of using a smart cap with an ostomy appliance, according to an exemplary embodiment of the present invention. In describing the method, reference is made herein to one or more of the exemplary embodiments of the ostomy appliance previously described.

At 2401, the user, during the course of the day, senses pressure from waste content which requires evacuation. Optionally, the pressure is sensed through a sensing lid 116 on cap 110 protruding in a proximal direction and/or through other pressure sensing features which may be available in the smart cap.

At 2402, optionally, in response to the sensed pressure the user slightly releases cap 110 from adaptor 108 opening a gas flow path 148 between proximal end 120 in the adaptor and the cap. Alternatively, the user activates other gas releasing mechanisms in adaptor 108, for example, by pressing a gas release valve 568 in an adaptor 508, or by pressing on a flexible fixation ring 444 on adaptor 408. In some embodiments, gas filter and/or deodorizing is performed, for example, by gas filter 349 in adaptor 308, or gas filter 541 in adaptor 508, or by sealing element 809 used with adaptor 808.

At 2403, the user determines if there is waste content to release. If no, the method returns to stage 2401. If yes, the method continues to stage 2404.

At 2404, the user removes lid 116. Manually removing the lid may be done at a time and place chosen by the user, for example in the privacy of a sanitary facility. Alternatively, lid is automatically ejected by safety release mechanism or other pressure-activated release mechanism.

At 2405 the ostomy bag is automatically deployed by the axial pressure from the waste content pushing on collapsed pouch 114, allowing the waste content to flow into the pouch. Alternatively, the user deploys collapsed pouch 114 using a strap or cord attached to the pouch, or any other method suitable for deployment of the bag.

At 2406, the user, having finished evacuation disposes of the deployed ostomy pouch 114 and waste content. Optionally, the user releases cap 110 including deployed pouch 114 from adaptor 108 for disposing the pouch.

At 2407, the user optionally determines if either ostomy wafer 102 or adaptor 508 requires replacement. If no, the method continues to stage 2409. If yes, the method continues to stage 2408.

At 2408, the user optionally detaches adaptor 108 from wafer 102 for disposing of the adaptor. Optionally the user removes the wafer for disposing of the wafer. Optionally, a new wafer 102 is placed over stoma 104 and adaptor 108 reattached to the new wafer. Alternatively a new adaptor 108 is attached to the wafer. Alternatively, adaptor 108 is attached to new wafer 102 before being placed over stoma 104. In some embodiments, the user removes wafer 102 together with adaptor 108 and then detaches the adaptor. In some embodiments, wafer 1102 and adaptor 1108 are integrally attached and removed together. Optionally, wafer 1102 and adaptor 1108 are replaced by a new adaptor, wafer, and/or integral wafer and adaptor. Wafer and/or adaptor are then reattached.

At 2409, the user reattaches a new cap 110 having a new collapsed pouch 114 to proximal end 120 of adaptor 108. Alternatively, the user reattaches removed cap 110 following accommodating a new collapsed pouch 114 in the cap. In some embodiments, stage 2409 is included in stage 2408 with new cap 110 coupled to adaptor 108 prior to coupling to wafer 102 or to placing over stoma 104.

At 2410, the user attaches lid 116 to cap 110. Optionally, sensing lid 116 is that previously used. Alternatively, new cap in 2409 includes a new lid 116.

At 2411, the user, during the course of the day, may require flushing of adaptor 108. Optionally, flushing may include washing the interior of adaptor 108, the stoma, the peristomal skin, intestinal irrigation, or any combination thereof. If flushing is required continue to stage 2412. If flushing is not required, go to stage 2401.

At 2412, the user connects a flushing fluid source to the adaptor, for example, through a flushing port 964 in adaptor 908. Optionally, the user first opens a plug 968 on flushing port 964 prior to connecting the flushing fluid source, which may be, for example, a bag or syringe of saline solution, to the flushing port. In some embodiments, the flushing fluid flows into the interior of adaptor 108 through flushing lumen 966 in the adaptor which is in fluid communication with the sealing element, for example, sealing element 909 or 909'. Optionally, the flushing fluid flows out from sealing element 909 or 909' into the interior of adaptor 908, washing the adaptor's interior, the stoma, the peristomal skin, or irrigating the intestine, or any combination thereof. Additionally or alternatively, a flushing tube 977 leading into the intestine may be connected to the sealing element, for example, sealing element 909", for irrigating the intestine.

In some embodiments, the flushing fluid source is connected, for example, by pressure fitting or threading, to a dedicated inlet in the cap. Optionally, the user first detaches the regular cap from the adaptor, then attaches a new cap adapted for connecting a flushing fluid source. Optionally, said adapted cap includes a high-capacity pouch adapted to receive waste and flushing fluid.

In some embodiments, during the flushing the user removes lid 116 for deploying pouch 114 for allowing the flushing fluid to flow into the pouch together with waste residue (stages 2404 and 2405). Optionally, the user deploys pouch 114 prior to applying the flushing fluid. Alternatively, the user deploys pouch 114 after applying the flushing fluid. Optionally, the user allows the fluid to remain inside the bowel for some time, and only then remove lid 116 and deploy pouch 114 to allow bowel content flush out.

The Ostomy Appliance In Situ

Figure 25:
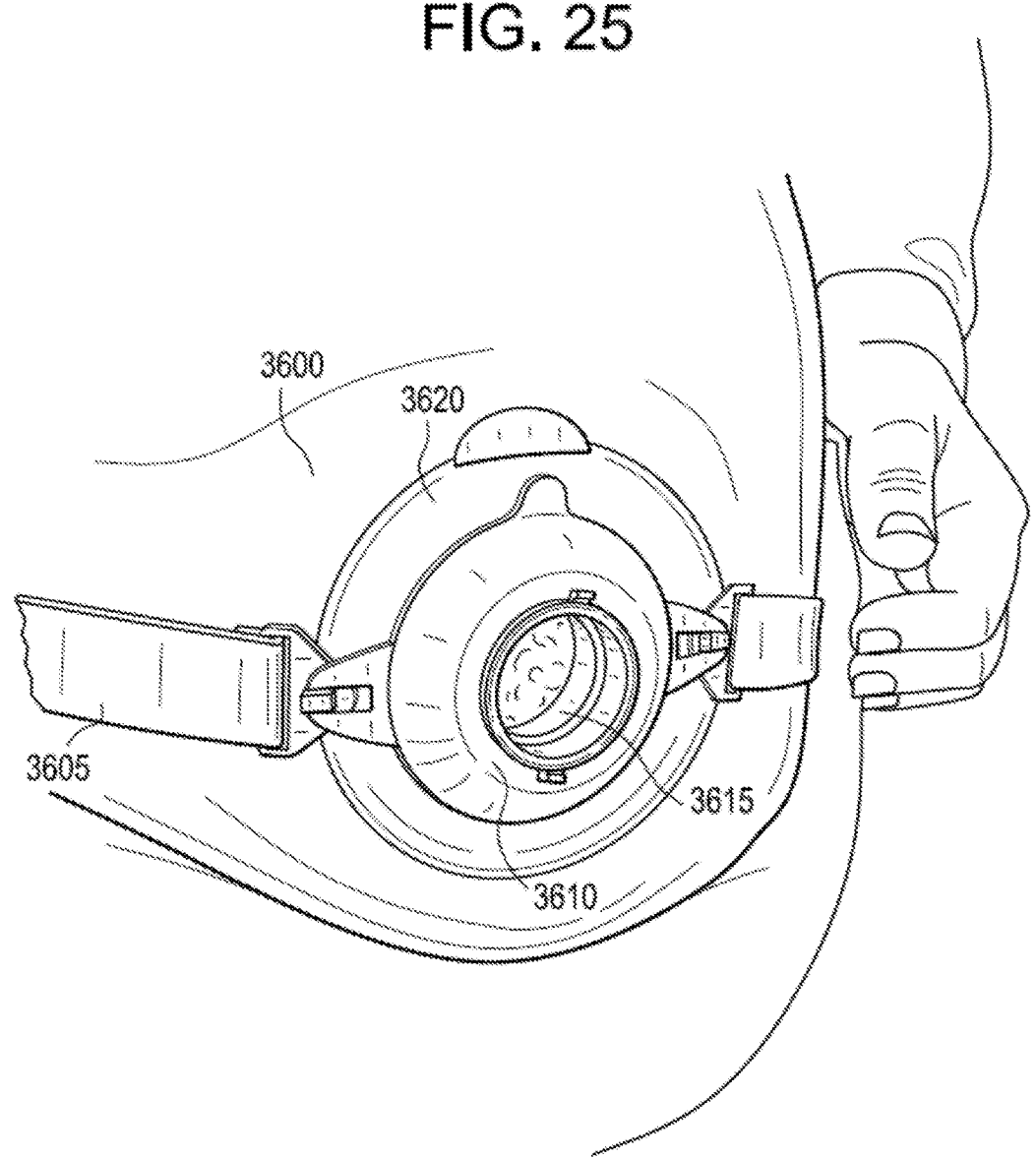
FIG. 25 is a picture illustrating an ostomy appliance worn on the body without a cap, in accordance with an exemplary embodiment of the present invention.
Figure 26:
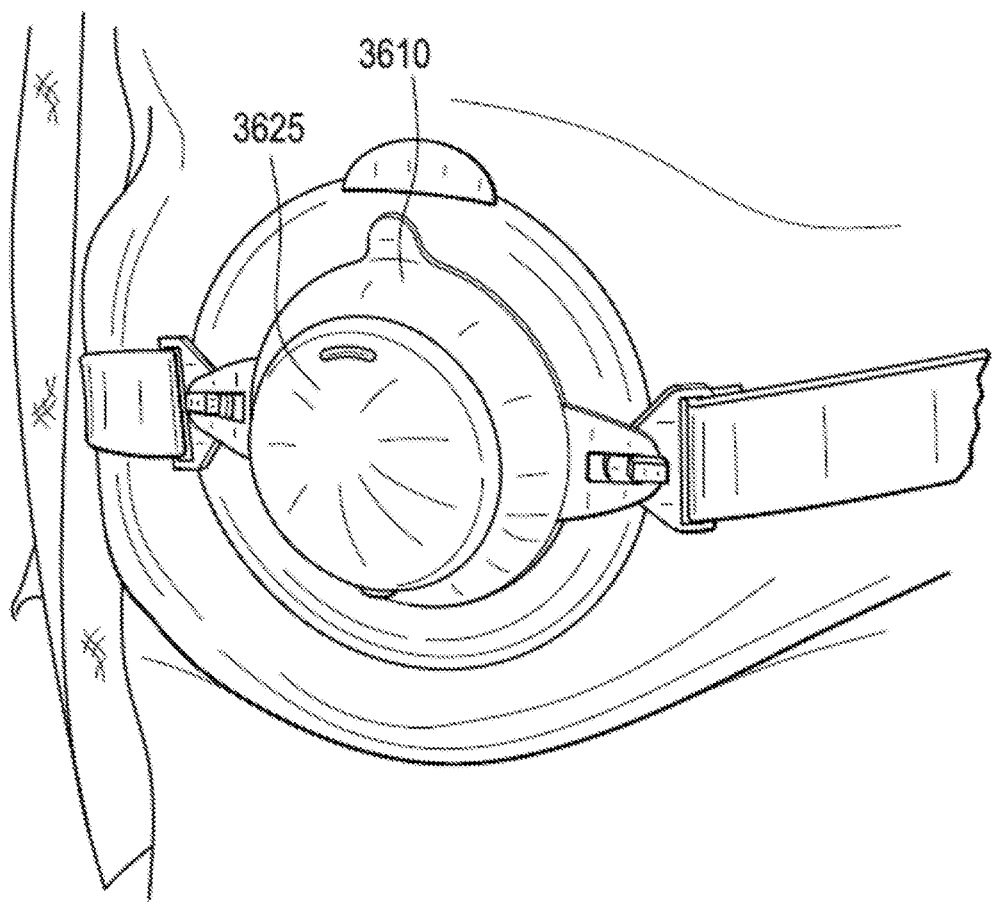
FIG. 26 is a picture illustrating an ostomy appliance worn on the body with a cap, in accordance with an exemplary embodiment of the present invention.
Figure 27:
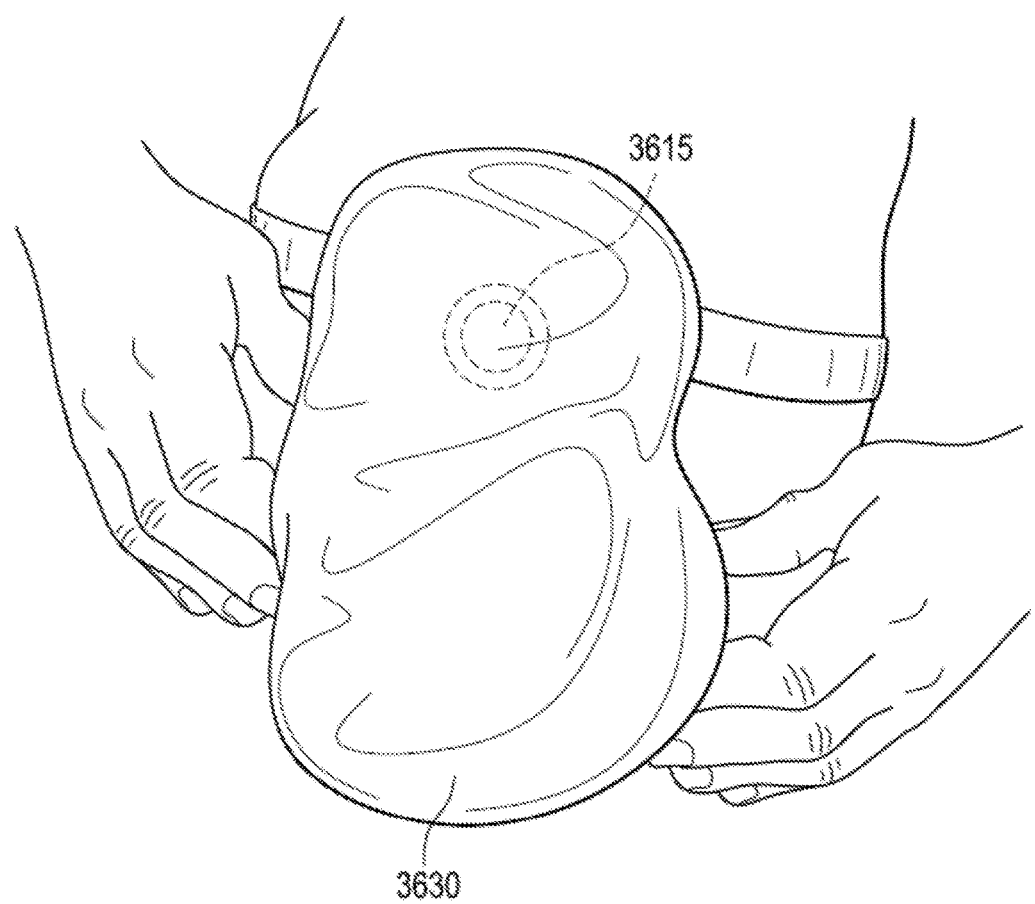
FIG. 27 is a picture illustrating an ostomy appliance worn on the body with a cap, the lid being removed and the waste pouch deployed, in accordance with an exemplary embodiment of the present invention.

Reference is now made to FIGS. 25, 26, and 27, which are pictures of an exemplary ostomy appliance as it is worn on the body during use.

In FIG. 25, the abdomen of a user 3600 is shown with a partially assembled ostomy stack in place. An ostomy wafer 3620 (adherent surface of the ostomy wafer is indicated) is further secured into place by an ostomy belt 3605. An adaptor 3610 is attached over the wafer. The lumen of the adaptor 3615 is in fluid communication with the open stoma underneath.

In FIG. 26, a cap 3625 comprised of a housing, pouch, and lid has been attached over the adaptor 3610.

In FIG. 27, the lid has been removed from the cap 3625, allowing the pouch 3630 to unfold from its stored position. The lumen 3615 leading to the stoma is discernible through the translucent material of the deployed pouch.

Block Diagram of an Ostomy Appliance

Figure 28:
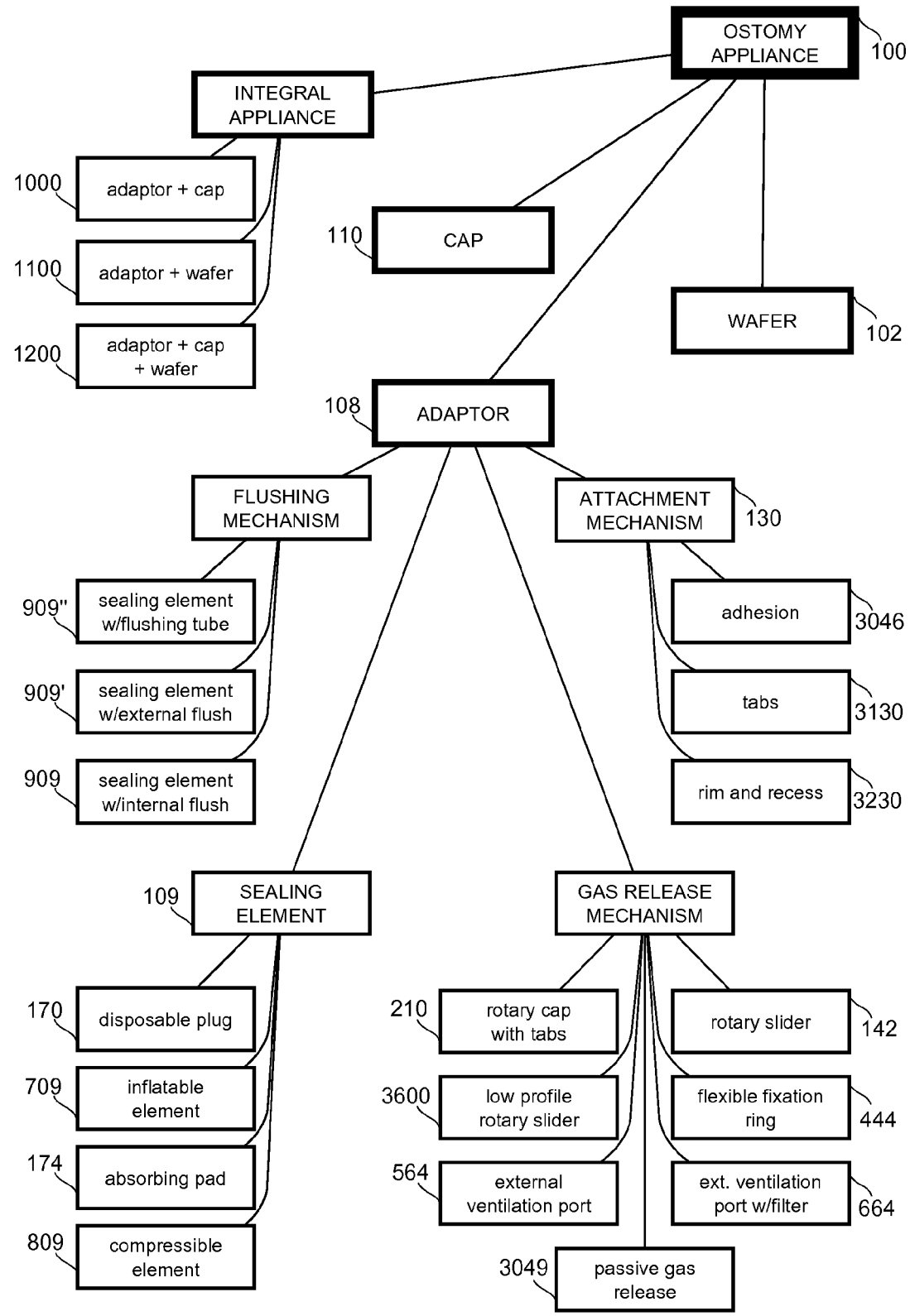
FIG. 28 is a block diagram of an ostomy appliance and its components, in accordance with some exemplary embodiments of the present invention.

Reference is now made to FIG. 28 which is a block diagram of ostomy appliance 100 and some of its components, according to some exemplary embodiments of the present invention. In some embodiments, ostomy appliance 100 includes any one component, or combination of components, disclosed herein for the ostomy appliance.

Additionally or alternatively, ostomy appliance 100 includes any one component or combination of components disclosed herein in other exemplary embodiments of the ostomy appliance. In some embodiments, ostomy appliance 100 includes integrally formed components.

The terms "comprises", "comprising", "includes", "including", "having" and their conjugates mean "including but not limited to".

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An ostomy appliance comprising an ostomy cap configured for coupling to an ostomy wafer surrounding a stoma of a user, the ostomy cap comprising:
   a cap housing having a proximal end and a distal end with a cavity therein, said distal end configured for coupling via an attachment mechanism integrally formed with the cap housing to an attachment element of said ostomy wafer, said distal end comprising a first opening in fluid communication with a second opening in said proximal end;
   a sealing element surrounding the stoma, when said ostomy appliance is coupled to said ostomy wafer, and configured for sealing interior to said attachment mechanism of said cap housing and said attachment element of said ostomy wafer between said cap housing and said ostomy wafer, said sealing element accommodated within said cavity of said cap housing;
   a lid removably attached to said proximal end of said cap housing; and
   a collapsed pouch in fluid communication with said second opening in said proximal end, wherein said collapsed pouch is restrained by said lid of said cap housing, and wherein said collapsed pouch is deployable into a waste collection mode through the removal of said lid, said removal actuatable manually and automatically by the pressure buildup inside said ostomy appliance.

2. The ostomy appliance of claim 1, wherein said sealing element comprises compressible material.

3. The ostomy appliance of claim 1, wherein said sealing element is a compressible foam element.

4. The ostomy appliance of claim 1, wherein said sealing element comprises a waste absorbing material.

5. The ostomy appliance of claim 4, wherein said sealing element is capable of absorbing up to 30 mL of liquid waste.

6. The ostomy appliance of claim 1, wherein said sealing element has an annular shape.

7. The ostomy appliance of claim 1, wherein said sealing element is made of a distending material capable of absorbing liquid waste and expanding within said cavity.

8. The ostomy appliance of claim 1, wherein said distal end comprises a snap-fit attachment mechanism for attachment to said wafer.

9. The ostomy appliance of claim 1 comprising a gas flow path having a filter for filtering gases flowing from the stoma.

10. The ostomy appliance of claim 9, wherein said filter comprises a deodorizing gas filter.

11. The ostomy appliance of claim 1, wherein said sealing element is permeable to gas.

12. The ostomy appliance of claim 1, wherein said housing comprises an opening for releasing gas flowing from a stoma without deploying said pouch.

13. The ostomy appliance of claim 12, wherein said opening for releasing gas is fitted with a valve.

14. The ostomy appliance of claim 13, wherein said valve is selectively openable by a user.

15. The ostomy appliance of claim 1, wherein said lid is configured to bulge outwards or stiffen in response to a pressure from waste content or flatus gas inside said housing, wherein the bulging outwards or stiffening of said lid is sensible by a user and indicates the need for deployment of said collapsed pouch to release waste content or gas.

16. The ostomy appliance of claim 1, wherein removal of said lid is automatically actuatable at colonic pressure of greater than or equal to 50 mmHg.

17. The ostomy appliance of claim 1, wherein said pouch is disposed externally to said housing.

18. The ostomy appliance of claim 1 adapted to be physically isolated from the stoma to prevent tissue damage.

19. A method of using an ostomy appliance attached to an ostomy wafer surrounding a stoma of a user, wherein said ostomy appliance comprises an ostomy cap configured for coupling to an ostomy wafer, the ostomy cap comprising:
   a cap housing having a proximal end and a distal end with a cavity therein, said distal end configured for coupling via an attachment mechanism integrally formed with the cap housing to an attachment element of said ostomy wafer, and said distal end comprising a first opening in fluid communication with a second opening in said proximal end;
   a sealing element having an annular shape and configured for sealing interior to the attachment mechanism of said cap housing and said attachment element of said ostomy wafer between said cap housing and said ostomy wafer, said sealing element accommodated within said cavity of said cap housing;
   a lid removably attached to said proximal end of said cap housing; and a collapsed pouch in fluid communication with said second opening in said proximal end, wherein said collapsed pouch is restrained by said lid of said cap housing, wherein said collapsed pouch is deployable into a waste collection mode through the removal of said lid, said removal actuatable manually and automatically by the pressure buildup inside said ostomy appliance, said method comprising manually removing said lid to deploy said pouch into said waste collection mode to eliminate waste through said stoma.

20. The method of claim 19, further comprising removing the ostomy appliance after elimination of waste and replacing it with an unused ostomy appliance.

21. The method of claim 19, wherein said lid is configured to bulge outwards or stiffen in response to a pressure from waste content or flatus gas inside said housing, and said method further comprises sensing said bulging or stiffening prior to said removing.

22. The method of claim 19, further comprising opening a valve to release gas without deploying said collapsed pouch, wherein said ostomy appliance further comprises an opening for releasing gas flowing from a stoma without deploying said pouch, and said opening is fitted with said valve, which is selectively openable by said user.

23. The method of claim 19, wherein removal of said lid is automatically actuatable at colonic pressure of greater than or equal to 50 mmHg.

24. An ostomy appliance comprising an ostomy cap configured for coupling to an ostomy wafer, the ostomy cap comprising:
   a cap housing having a proximal end and a distal end with a cavity therein, said distal end configured for coupling via an attachment mechanism integrally formed with the cap housing to an attachment element of said ostomy wafer through a snap-fit arrangement, said distal end comprising a first opening being in fluid communication with a second opening in said proximal end;
   an annular compressible foam sealing element accommodated within said cavity of said cap housing, wherein said sealing element is configured to surround a stoma and to seal an interface between said cap housing and said ostomy wafer, when said ostomy cap is coupled to said ostomy wafer, and wherein said sealing element is permeable to gas;
   a lid removably attached to said proximal end of said cap housing, said lid configured to bulge outwards or stiffen in response to a pressure from waste content or flatus gas inside said cap housing;
   a collapsed pouch in fluid communication with said second opening in said proximal end, wherein said collapsed pouch is restrained by said lid of said cap housing and disposed externally to said housing, wherein said collapsed pouch is deployable into a waste collection mode through the removal of said lid, wherein said removal is actuatable manually and automatically by the pressure buildup inside said ostomy appliance; and
   a gas flow path for releasing gases flowing from the stoma, wherein said cap housing comprises an opening fitted with a valve selectively openable by a user for releasing gas flowing from a stoma, and wherein said gas flow path passes through said opening fitted with said valve.

25. The ostomy appliance of claim 24, further comprising a gas flow path having a deodorizing filter for filtering gases flowing from the stoma.

26. The ostomy appliance of claim 24, wherein said sealing element is made of a distending material capable of absorbing liquid waste and expanding within said cavity.

* * * * *